United States Patent
Alderborn et al.

(10) Patent No.: US 10,561,617 B2
(45) Date of Patent: Feb. 18, 2020

(54) MODIFIED RELEASE COMPOSITION OF ORLISTAT AND ACARBOSE FOR THE TREATMENT OF OBESITY AND RELATED METABOLIC DISORDERS

(71) Applicant: EMPROS PHARMA AB, Solna (SE)

(72) Inventors: Göran Alderborn, Uppsala (SE); Anders Forslund, Uppsala (SE); Ulf Holmbäck, Uppsala (SE); Hans Lennernäs, Uppsala (SE); Jan Stefan Persson Gruden, Uppsala (SE)

(73) Assignee: EMPROS PHARMA AB, Solna (SE)

( * ) Notice: Subject to any disclaimer, the term of this patent is extended or adjusted under 35 U.S.C. 154(b) by 0 days.

(21) Appl. No.: 15/536,334

(22) PCT Filed: Dec. 17, 2015

(86) PCT No.: PCT/EP2015/080265
§ 371 (c)(1),
(2) Date: Jun. 15, 2017

(87) PCT Pub. No.: WO2016/097170
PCT Pub. Date: Jun. 23, 2016

(65) Prior Publication Data
US 2017/0360715 A1 Dec. 21, 2017

(30) Foreign Application Priority Data

Dec. 17, 2014 (EP) ..................................... 14198468

(51) Int. Cl.
| | |
|---|---|
| *A61K 9/20* | (2006.01) |
| *A61K 9/24* | (2006.01) |
| *A61K 9/28* | (2006.01) |
| *A61K 31/365* | (2006.01) |
| *A61K 31/702* | (2006.01) |
| *A61K 9/00* | (2006.01) |

(52) U.S. Cl.
CPC .......... *A61K 9/2081* (2013.01); *A61K 9/0053* (2013.01); *A61K 9/209* (2013.01); *A61K 9/2013* (2013.01); *A61K 9/2018* (2013.01); *A61K 9/2027* (2013.01); *A61K 9/2054* (2013.01); *A61K 9/284* (2013.01); *A61K 9/2846* (2013.01); *A61K 31/365* (2013.01); *A61K 31/702* (2013.01)

(58) Field of Classification Search
None
See application file for complete search history.

(56) References Cited

U.S. PATENT DOCUMENTS

| | | | |
|---|---|---|---|
| 6,419,954 B1 * | 7/2002 | Chu | A61K 9/2031 424/441 |
| 2009/0220611 A1 * | 9/2009 | Dargelas | A61K 9/2077 424/495 |

FOREIGN PATENT DOCUMENTS

| | | |
|---|---|---|
| CN | 102 872 062 A | 1/2013 |
| EP | 0 638 317 A1 | 2/1995 |
| WO | WO 99/37308 A1 | 7/1999 |
| WO | WO-02/083153 A1 | 10/2002 |
| WO | WO 2008/000420 A1 | 1/2008 |
| WO | WO-2009/039157 | 3/2009 |
| WO | WO 2010/065491 A2 | 6/2010 |
| WO | WO 2011/134962 A2 | 11/2011 |

OTHER PUBLICATIONS

International Search Report dated Feb. 24, 2016 in application No. PCT/EP2015/080265.

* cited by examiner

*Primary Examiner* — John Pak
*Assistant Examiner* — Daniel L Branson
(74) *Attorney, Agent, or Firm* — Foley & Lardner LLP

(57) ABSTRACT

The present invention relates to a modified-release composition comprising orlistat and acarbose, comprising individually distinct parts with different release patterns: a) a first part, G1, comprising from about 5 to about 70% w/w of the total dose of acarbose, b) a second part, G2A, comprising from about 30 to about 95% w/w of the total dose of acarbose, c) a third part, G2B, comprising from about 10 to about 90% w/w of the total dose of orlistat, and d) a fourth part, G3, comprising from about 10 to about 80% w/w of the total dose of orlistat, and the total concentration of acarbose and orlistat, respectively, in the composition is 100% w/w.

27 Claims, 29 Drawing Sheets

1A

Figure 1:
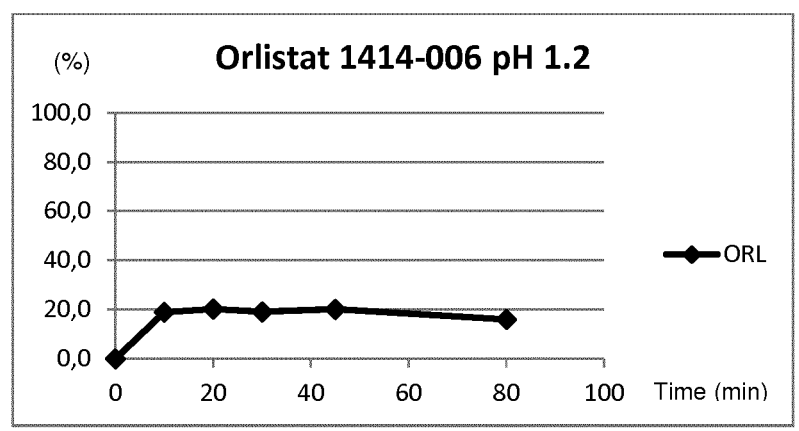
Figure 1:
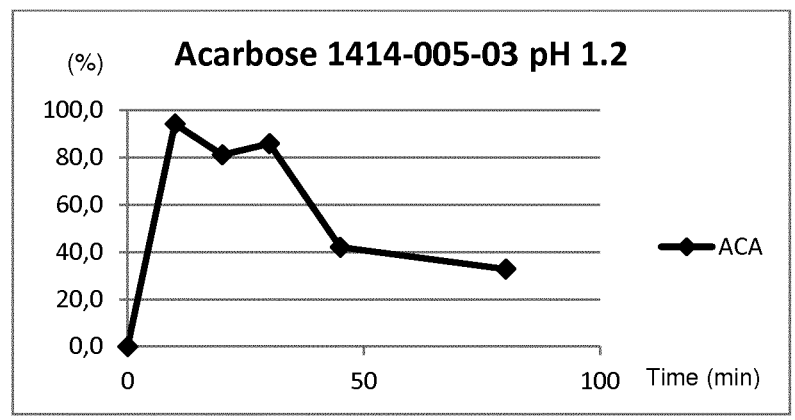

1B 1 fit to G1 Acr 2 fit to G2 Orl 3 fit to G2 Acr 4 fit to G3 Orl 5 sim Acr G1G2G3

6 sim Orl G1G2G3

MODIFIED RELEASE COMPOSITION OF ORLISTAT AND ACARBOSE FOR THE TREATMENT OF OBESITY AND RELATED METABOLIC DISORDERS

FIELD OF THE INVENTION

The present invention relates to an oral modified release pharmaceutical composition comprising the drug substances orlistat and acarbose. The composition is administered by the oral route and is designed to deliver the individual drug substance to specific regions of the gastrointestinal (GI) tract where their pharmacological activities are located. The composition is suitable for use in the treatment of various metabolic diseases such as obesity, overweight and type 2-diabetes. In separate aspects, the invention also relates to i) an oral modified release pharmaceutical composition comprising acarbose, and ii) an oral modified release pharmaceutical composition comprising orlistat.

In a further aspect the invention relates to the use of the above-mentioned compositions in cosmetics, notably for reducing weight.

BACKGROUND OF THE INVENTION

The worldwide prevalence is estimated to be 1.5 billion overweight and 500 million obese individuals[1]. Overall, more than one out of ten of the world's adult population is obese. In 2010, more than 40 million children under five were overweight[2]. Once considered a high-income country problem, overweight and obesity are now on the rise in low- and middle-income countries, particularly in urban settings[3]. Overweight and obesity are the fifth leading risks for global deaths[1]. At least 2.8 million adults die each year globally as a result of being overweight or obese. In addition, 44% of the diabetes burden, 23% of the ischemic heart disease burden and between 7% and 41% of certain cancer burdens are attributable to overweight and obesity[2,4]. In June 2013, the American Medical Association officially recognized obesity as a disease[5].

There is a great concern globally of this serious health issue, but different strategies have not been successful to reverse the obesity trends among the global population. Neither has the awareness for healthier diet and increased physical activity proved particularly effective. There exist several potential explanations such as: the absence of access to healthy, affordable foods or safe places for physical activity, particularly in lower-income neighbourhoods and communities; the inferiority of freshly prepared foods vs. fast foods or pre-packaged foods in terms of preservation, portability, and palatability; the marketing of mostly unhealthy products by the food and beverage industry; and modern cultural habits that increase sedentary behaviours, degrade eating cadences and locations, and incur excess stress levels and sleep debt[1,3]. Life-style intervention affecting dietary intake and energy expenditure are important, however, often not enough. It is obvious that obesity should be considered as a chronic, incurable disease, which needs better drug products for a successful treatment[6]. Therefore, there is a need for a novel safe and efficient medical treatment.

Type 2-diabetes is growing epidemically and this rise is closely associated with obesity. Type 2-diabetes has multiple manifestations and sub-optimal treatment is associated with progressive beta-cell failure. Although lifestyle measures, including eating habits and physical activity, should be first-line treatment, success is difficult to achieve, and pharmaceutical intervention is almost always required[7]. Before manifest type 2-diabetes is diagnosed, the patients usually have a period of impaired glucose tolerance. If this impaired glucose tolerance, which may precede or follow weight gain, is correctly treated, the progression towards diabetes might be halted or averted[8]. Current treatment options are limited to lifestyle changes, or secondly metformin. Hence, there is a need for a novel safe and efficient medical treatment.

Yet another indication for this invention would be treatment of overweight/obesity in association with Polycystic Ovary Syndrome (PCOS). Polycystic ovary syndrome (PCOS) is one of the most common endocrine disorders among females and produces symptoms in 5% women of reproductive age (conservative figure[9]). One of the most common immediate symptoms is insulin resistance. This insulin resistance is often associated with obesity, type 2 diabetes, and high cholesterol levels[9]. Current recommended pharmacological treatment (in addition to contraceptives) of the obese and/or glucose impaired PCOS patients is limited to metformin[10]; although current guidelines state that the evidence base is not strong[10]. Other insulin sensitizers, for example thiazolidinediones, have unwanted risk/benefit ratio and are not recommended[10]. For the PCOS patients, there is a clinical need for a drug that safely both decreases weight and improves glucose tolerance.

Nonalcoholic steatohepatitis (NASH) is liver inflammation and damage caused by a buildup of fat in the liver. NASH affects 2 to 5 percent of Americans. An additional 10 to 20 percent of Americans have fat in their liver, but no inflammation or liver damage, a condition called "fatty liver." or NAFLD[11]. Both NASH and NAFLD are becoming more common, possibly because of the greater number of Americans with obesity[11]. Currently, no specific therapies for NASH exist, except for lifestyle interventions, so there exists an unmet clinical need.

According to the new International Diabetes Federation (IDF) definition, for a person to be defined as having the metabolic syndrome the person must have: Central obesity plus any two of the following four factors:

- raised triglyceride (TG) level or specific treatment for this lipid abnormality
- reduced high-density lipoprotein (HDL) cholesterol or specific treatment for this lipid abnormality
- raised blood pressure or treatment of previously diagnosed hypertension
- raised fasting plasma glucose or previously diagnosed type 2-diabetes The present inventors postulate that the proposed product will directly or indirectly affect most of the components of the metabolic syndrome, mainly decreasing weight, improving glucose control, which in turn will lead to improved hepatic fat metabolism with decreased triglycerides concentration. The product is expected to also have direct effect on triglyceride concentration.

Current Treatment Options for Obesity and Overweight

Several pharmacological principles have been considered for treatment of obesity or overweight including increasing energy expenditure (stimulants), suppressing caloric intake (anorectic agents), limit nutrient absorption and modulating insulin production and/or action[7,10,12]. Four centrally-acting noradrenergic agents (phentermine, diethylpropion, phendimetrazine, benzphetamine) are FDA-approved for usually less than 12 weeks management of obesity. All were approved before the necessity of long-term treatment for obesity was established. In addition, none were required to meet the current efficacy benchmarks for weight loss relative to placebo (mean weight loss ≥5% more than that of the placebo group or proportion of drug-treated subjects who lose ≥5% of initial weight is ≥35% and approximately double the proportion who lose ≥5% in the placebo group)[13]. Drugs for weight management that are approved for long-term usually result in, on average, an additional weight loss relative to placebo ranging from ~3% for orlistat and lorcaserin to 9% for phentermine/topiramate-ER at one year[14]. Already in 2005, the stimulants, including dinitrophenol, amphetamine and ephedra, were abandoned. Among anorectic agents sibutramine was on the market for a few years before adverse effects led to its removal, together with the short lived appetite suppressor Rimonabant. Lorcaserin is a selective serotonin 2C (5HT2c) receptor agonist that was anticipated to recapitulate the weight loss effects of fenfluramine without its adverse cardiac effects[15]. Lorcaserin decreased body weight modestly, by about 3.2 kg (~3.2% of initial body weight) more than placebo[16]. Among patients with diabetes, lorcaserin treatment led to lower body weight and improved glycated hemoglobin concentrations[17]. Liraglutide (Saxenda®; liraglutide injection) was approved (both by EMA and FDA) as a treatment option for chronic weight management in addition to a reduced-calorie diet and physical activity. The drug is approved for use in adults with a body mass index (BMI) of 30 or greater (obesity) or adults with a BMI of 27 or greater (overweight) who have at least one weight-related condition such as hypertension, type 2 diabetes, or high cholesterol (dyslipidemia). GLP-1 analogues (such as liraglutide and exenatide) have initially been used as diabetes type-2 medication, but successful weight loss trials have been performed where patients lost 8 kg more after one year on the highest dose of liraglutide; compared to the placebo group which lost 2 kg[18]. A recently completed phase 3 trial evaluating liraglutide 3.0 mg/day vs. placebo for weight maintenance in 422 non-diabetic overweight and obese patients (72% retention)[19]. The patients successfully lost ≥5% initial weight during a 4-12 week dietary run-in, and also observed an additional weight reduction of 6.2% in the active treatment group over the ensuing 56 weeks, which ends up in a placebo subtracted-difference of −6.1%[19]. However, safety concerns exist regarding these drugs, chiefly regarding suggested increased risk of developing pancreatic cancer[20]. The FDA still approves the use of liraglutide but encourages both prescribers and patients to report possible side effects[20].

The tale of liraglutide mimics that of many previous anti-obesity drugs. During the last 20 years, about 10 different drugs have been put out on the market, only to be withdrawn within a few years[21]. The current alternatives include attempts to limit nutrient (lipids) absorption (orlistat), and perhaps to use compounds affecting insulin (see below). In conclusion: the available pharmaceutical products based on a single unit that possesses a positive benefit-risk ratio for this patient group are very limited.

It has been suggested that a combination of drugs would be successful. For instance, FDA recently approved the first obesity combination with phentermine and topiramate[6]. Topiramate, an antiepileptic, produces moderate weight loss, but the FDA approval as a single drug for obesity treatment was not pursued by the manufacturer[14]. When topiramate was combined with phentermine and extensively clinically tested, the safety profile of the combination was confirmed and thus gained FDA approval for marketing. Weight loss averages approximately 13% over 2 years[6]. Another combination, bupropion and naltrexone)(Mysimba®, produces approximately 6% weight loss in clinical trials[14] and has been approved in certain countries. Other single agents and combinations are in clinical trials, but all seem to produce results similar to those discussed above[6].

Currently, orlistat (Xenical®) is the only available anti-obesity drug worldwide. It is available both in prescription (120 mg) and over-the-counter (60 mg) strength and is given by the oral route. Orlistat is a semi-reversible and local inhibitor of gastric and pancreatic lipases in the GI tract and acts as an antiobesity drug by preventing intestinal absorption of dietary fats (i.e. reducing energy intake). The fraction of the dose absorbed of the highly lipophilic orlistat (log P 8.5) is low (<3%) and accordingly the plasma exposure is low (<5 ng/ml)[22]. Today, orlistat is available in a conventional relative rapid release oral dosage form. However, orlistat, although safe, is associated with some side-effects that severely hamper compliance. In clinical trials, about 25% or more of the patients complain about GI side-effects including diarrhea, oily spottings and fecal urgency[22]. This, in conjunction with the rather modest effect on weight (Best case scenario: 10% relative weight loss versus placebo 6% relative weight loss[23], makes orlistat in this conventional and relative rapid release dosage form unattractive for the vast majority of obese patients. However, in a recent report FDA clearly stated that orlistat is safe and has clinical benefit[24].

Acarbose (Glucobay®) is a competitive α-glucosidase and pancreatic α-amylase inhibitor, which inhibits the hydrolysis of oligosaccharides during GI luminal digestion of a meal[25]. Acarbose has hydrophilic properties (log P −8.1) and consequently low intestinal permeability, low fraction dose absorbed (<5%), low bioavailability and systemic exposure of acarbose. Acarbose, available in conventional immediate release dosage form, is currently used as a diabetic drug, mainly in Asia, but only scarcely in Western countries. It has not been approved for treatment of obesity.

As with orlistat, a large part of the patients using acarbose reports GI tolerability problems (mainly flatulence, diarrhea as well as GI and abdominal pains)[25], which limits its current clinical use in western countries.

There are currently two other α-glucosidase inhibitors on the market, miglitol and voglibose. Miglitol is FDA approved and available in several countries, whereas voglibose is approved only in Japan[26]. Acarbose, miglitol and voglibose lowers HbA1c to more or less the same extent, with slightly different side effect[26]. Miglitol is absorbed to 100% and is excreted though the kidneys; whereas voglibose is, in similarity to acarbose, only negligibly absorbed. Voglibose, most probably due to its low dose (0.2 mg voglibose/meal is a common dose) shows lower frequency of GI side effects compared to acarbose; but does not decrease rate of gastric emptying[27]. So far available studies indicate that all three α-glucosidase inhibitors are safe with no systemic effects[26,27]. There are also a plethora (>1200 compounds) of identified plant compounds that show varying α-glucosidase inhibitory effects[28]. Acarbose stands out as it is by far the most clinically used and investigated compound, is approved worldwide and its patent has expired.

There is currently no other lipase inhibitor approved for treatment of obesity, with the possible exception of cetilistat. Cetilistat has been shown to have led to similar weight reduction as orlistat, but with much lower frequency of side effects[29]. Cetilistat is currently only approved in Japan and FDA approval is pending. There are also some lipase inhibitors from plants[30], where a few can be bought as OTC-drugs. Thus, the list of potential lipase inhibitors is very short.

As it appears from the discussion above, there is a need for developing an oral pharmaceutical composition for treatment of obesity or overweight that is more effective, but also has reduced side effects and improved tolerability compared with the products on the market today, especially compared with Xenical® tablets. Such an oral product is expected to have an improve benefit: safety ratio and have a favorable health economic profile.

The present inventors have developed a composition comprising acarbose and orlistat, in a modified release dosage form, which has been designed to release acarbose and/or orlistat in specific parts of the GI tract and at specific amounts and release rates to optimize the digestion enzyme inhibition and nutrient inducing satiety feed-back mechanism. By this design of the dosage form it is possible to expose receptors in the intestine to ligands derived from the ingested diet, such as free fatty acids and hexoses, and then to target an appetite regulating system in this patent application named the gastro-intestinal brake (GI brake, described in more detail below) to obtain improved effect of the treatment and, at the same time, reduce the side-effects. Thus, it is possible to obtain a synergistic effect of the two drug substances with an oral modified-release dosage form. Moreover, it is expected that a suitable effect can be obtained with a reduced amount of orlistat and acarbose compared to the dose used in Xenical® (start dose 120 mg) and Glucobay® (start dose 50 mg), respectively.

There is also a need for providing compositions comprising either orlistat or acarbose, which compositions have suitable properties with respect to release of the drug substance so that the drug substance is released in the relevant parts of the gastrointestinal tract and which compositions lead to reduced side-effects compared to known compositions.

A combination of orlistat and acarbose in an oral pharmaceutical product has been suggested in CN 2011 1195582 (Luan Pharm Group Corp). The combination is provided in the form of tablets. The formulations are designed as traditional tablets without any modification of the release rate for any of the compounds (i.e. acarbose and orlistat) to be able to target the GI brake mechanism(s). As seen from the Examples herein a comparison has been made between a composition of CN 2011 1195582 and the present invention and a markedly different dissolution profile is obtained (eg compare FIGS. 11 and 12 with FIG. 22).

A combination of orlistat and acarbose has also been suggested in EP 0 638 317 (Hoffmann-La Roche). As seen from the Examples herein a comparison has been made between a composition of EP 0 638 317 and the present invention and a markedly different dissolution profile is obtained (eg compare FIGS. 11 and 12 with FIG. 21).

DETAILED DESCRIPTION OF THE INVENTION

The present invention provides a pharmaceutical or cosmetic modified-release (MR) composition for oral use for the treatment of obesity, overweight and/or obesity. The composition comprises orlistat and acarbose as active pharmaceutical ingredients (APIs) and is designed to release each of the active substances in different parts of the GI tract and in different amounts with various release rates (amount/time). The composition is designed to optimize the balance between effective enzyme inhibitions and nutrient induced gastro-intestinal brake on the one hand and side-effects on the other to obtain an improved benefit/safety ratio compared with that obtained if orlistat or acarbose was used alone in a conventional composition, or compared with that obtained if a combination of orlistat and acarbose was used in a conventional formulation with one relative rapid release rate. The individual APIs (acarbose and orlistat) will also by themselves have an effect on the GI brake, but to a lesser degree than the combination. The present inventors have surprisingly found that acarbose has a pH dependent degradation. A similar tendency was seen for orlistat, see FIG. 1A-B. This has been considered in the design of this MR dosage form by using enteric coating principles.

In the following is given a description focused on a combination product of orlistat and acarbose. However, it is to be understood that the description is also valid for compositions i) where the orlistat component is excluded and thus, where the invention only relates to an acarbose composition, or ii) where the acarbose component is excluded and, thus, where the invention only relates to an orlistat composition. Such compositions may be used in monotherapy for treatments as mentioned herein, or they may be combined in dual therapy for treatments as mentioned herein. The release of acarbose from a composition only containing acarbose as a drug substance will follow the release pattern given herein, and the release of orlistat from a composition only containing orlistat as a drug substance will follow the release pattern for orlistat given herein.

The release rates of the APIs are designed so that acarbose is released both in the stomach and some parts of the small intestine via defined different formulation principles, whereas orlistat is released throughout the small intestines, but at different rates, until the end of jejunum. By releasing the unchanged APIs at different rates, sufficient inhibition of digestive enzymes is achieved; enabling relevant amounts of undigested carbohydrates and lipids to reach the distal regions of the small intestine. The digested metabolites (fatty acids, monoacylglycerols and hexose) that is formed locally through local digestion will then act as ligands and stimulate the so-called gastro-intestinal brake effect.

In the present context the terms RR denotes rapid release, DR denotes delayed release and PR denotes prolonged release. The delayed release means that the release has been delayed, but when the release starts it may be rapid or prolonged. The subscripts DC denoted delayed coating, GASTRIC denotes that the release starts in the stomach, but there may still be release of the drug substance after passage into and through the small intestine until the end of jejunum, EC denotes an enteric coating, i.e. a coating with certain polymers that has a pH-cut off of about 4, i.e. they do not dissolve at acid pH and gradually begins to dissolve at about pH 4. As seen from the examples herein polymers are employed having a $pK_a$ value of about 5.5, i.e. they begin to dissolve at about pH 5.5. Accordingly, as the drug substances are not released at pH below 4, PROX-SI denotes that the release should start and mainly take place in the proximal small intestine, and INTESTINAL denotes that the release should take place in the first part of small intestine until the end of jejunum.

This invention provides an oral pharmaceutical modified-release (MR) composition that is designed to i) release a part of the total dose of acarbose in the stomach, but in a delayed manner in order to ensure that particles with acarbose will be well mixed with the food components and chyme in the postprandial stomach, ii) release a part of the total dose of acarbose and a part of the total dose of orlistat in duodenum and jejunum; this release should be relatively fast, as both acarbose and orlistat should be available to exert their effect in duodenum and jejunum, and iii) release of a part of the total dose of orlistat in duodenum and jejunum.

For monotherapy, the present invention provides an oral pharmaceutical modified-release composition comprising acarbose that is designed to
  i) release a part of acarbose in the stomach, but in a delayed manner in order to ensure that the particles with acarbose will be well mixed with the food components and chyme in the postprandial stomach,
  ii) release a part of acarbose relatively fast to make acarbose available in duodenum and jejunum.

For monotheray, the present invention provides an oral pharmaceutical modified-release composition comprising orlistat that is designed to
  i) release a part of orlistat relatively fast to make orlistat available in duodenum and jejunum,
  ii) release of part of orlistat in duodenum and jejunum.

A composition as described above can be formulated as an oral dosage form in many different ways as will be described herein later. One of the challenges is to ensure that the individual drug substances in sufficient doses reach the identified part of the GI tract.

The inventors have found that the following is important to arrive at a suitable pharmaceutical composition:

Acarbose:
i) 5-70% w/w of the total dose of acarbose should be released in a prolonged manner, but starting already in the stomach after a delay of about 30-60 min and continuing in duodenum and jejunum, and
ii) 30-95% w/w of the total dose of acarbose should be released in the proximal part of the small intestine and the release should be relatively rapid to obtain the effect already in the duodenum, and
iii) 0-20% w/w of the total dose of acarbose may be released in a prolonged release manner, in other parts of the GI tract, preferably 0-10% w/w such as 0-5% w/w.

Orlistat:
iv) 0-10% w/w of the total dose of orlistat may be released in the stomach, preferably 0-2% w/w or 0% w/w. If some orlistat is released in the stomach, then there should be a delay in the release of about 0-60 min or 30-60 min,
v) 10-90% w/w of the total dose of orlistat should be released in duodenum and proximal jejunum and the release should be relatively rapid to obtain the effect already in the duodenum and proximal jejunum, and
vi) 10-80% w/w of the total dose of orlistat should be released in duodenum and jejunum in a prolonged release manner, and
vii) 0-5% w/w of the total dose of orlistat may be released in other parts of the GI tract.

A suitable composition may comprise individual parts designed to fulfil i), ii), v) and vi). As the physiological conditions in the GI tract are complex and highly dynamic as described herein, such a composition may also release drug substances as described in iii), iv) and/or vii).

Thus, a composition of this invention may be an oral modified-release (MR) composition comprising acarbose and orlistat, wherein the composition contains individually distinct parts. The composition may contain three or four different parts:
a) a first part, G1, comprising from about 5 to about 70% w/w of the total dose of acarbose,
b) a second part, G2A, comprising from about 30 to about 95% w/w of the total dose of acarbose,
c) a third part, G2B, comprising from about 10 to about 90% w/w of the total dose of orlistat, and
d) a fourth part, G3, comprising from about 10 to about 80% w/w of the total dose of orlistat, and the total concentration of acarbose and orlistat, respectively, is 100% w/w; if the composition only contains three parts, part b) and c) is combined. The combined part is called G2. The release patterns of the distinct parts are different as the individual parts are designed to release acarbose and orlistat in the different parts of the gastrointestinal tract.

The modified release part may comprise the following three or four different parts:
a) a first part, G1, comprising from about 5 to about 60% w/w of the total dose of acarbose,
b) a second part, G2A, comprising from about 40 to about 95% w/w of the total dose of acarbose,
c) a third part, G2B, comprising from about 30 to about 85% w/w of the total dose of orlistat, and
d) a fourth part, G3, comprising from about 15 to about 70% w/w of the total dose of orlistat, and the total concentration of acarbose and orlistat, respectively, is 100% w/w, if the composition only contains three parts, part b) and c) is combined as part G2, or it may contain the following three or four different parts:
a) a first part, G1, comprising from about 5 to about 50% w/w of the total dose of acarbose,
b) a second part, G2A, comprising from about 50 to about 95% w/w of the total dose of acarbose,
c) a third part, G2B, comprising from about 30 to about 80% w/w of the total dose of orlistat, and
d) a fourth part, G3, comprising from about 20 to about 70% w/w of the total dose of orlistat, and the total concentration of acarbose and orlistat, respectively, is 100% w/w, if the composition only contains three parts, part b) and c) is combined as part G2, or the composition may contain the following three or four different parts:
a) a first part, G1, comprising from about 5 to about 40% w/w of the total dose of acarbose,
b) a second part, G2A, comprising from about 60 to about 95% w/w of the total dose of acarbose,
c) a third part, G2B, comprising from about 30 to about 75% w/w of the total dose of orlistat, and
d) a fourth part, G3, comprising from about 25 to about 70% w/w of the total dose of orlistat, and the total concentration of acarbose and orlistat, respectively, is 100% w/w, if the composition only contains three parts, part a) and c) is combined as part G2.

As mentioned above, the release in duodenum and proximal part of jejunum of both acarbose and orlistat should be rapid and, accordingly, the formulation of part b) and c) above may be combined into only one part. In such a case a composition according to this invention may also be a composition comprising acarbose and orlistat, wherein the composition contains three different parts:
a) a first part, G1, comprising from about 5 to about 70% w/w of the total dose of acarbose,
b) a second part, G2, comprising from about 30 to about 95% w/w of the total dose of acarbose, and from about 10 to about 90% w/w of the total dose of orlistat, and
c) a third part, G3, comprising from about 10 to about 80% w/w of the total dose of orlistat, and the total concentration of acarbose and orlistat, respectively, is 100% w/w.

The composition may contain the following three different parts:
a) a first part, G1, comprising from about 5 to about 60% w/w of the total dose of acarbose,
b) a second part, G2, comprising from about 40 to about 95% w/w of the total dose of acarbose, and from about 30 to about 85% w/w of the total dose of orlistat, and c) a third part, G3, comprising from about 15 to about 70% w/w of the total dose of orlistat, and the total concentration of acarbose and orlistat, respectively, is 100% w/w.

The composition may contain the following three different parts:
a) a first part, G1, comprising from about 5 to about 50% w/w of the total dose of acarbose,
b) a second part, G2, comprising from about 50 to about 95% w/w of the total dose of acarbose, and from about 30 to about 70% w/w of the total dose of orlistat, and
c) a third part, G3, comprising from about 30 to about 70% w/w of the total dose of orlistat, and the total concentration of acarbose and orlistat, respectively, is 100% w/w.

The composition may contain the following three different parts:
a) a first part, G1, comprising from about 5 to about 40% w/w of the total dose of acarbose,
b) a second part, G2, comprising from about 60 to about 95% w/w of the total dose of acarbose, and from about 30 to about 75% w/w of the total dose of orlistat, and
c) a third part, G3, comprising from about 25 to about 70% w/w of the total dose of orlistat, and the total concentration of acarbose and orlistat, respectively, is 100% w/w.

Thus, this invention provides an oral pharmaceutical MR composition comprising orlistat and acarbose, wherein the composition contains components with different release characteristics for release at different parts along the GI tract:

i) a $DR_{DC}$-$PR_{GASTRIC}$ acarbose part, G1, that is designed to release acarbose in a delayed, but prolonged manner starting in the stomach. This will lead to a delay in release of about 20-40 min, whereafter the release of the API will continue after emptying of the formulation into the small intestine. Such a part of the composition may be eg in the form of granules, pellets, minitablets etc. This part typically contains from about 5 to about 70% w/w of the total dose of acarbose. The delayed release is typically obtained by providing the granules, pellets, minitablets etc. with a delayed coating.

ii) a $DR_{EC}$-$RR_{PROX\ SI}$ part, G2 or G2A and G2B, that is designed to initiate a release acarbose and orlistat in the proximal small intestine. Such a part of the composition may be eg in the form of granules, pellets, minitablets etc. It contains from about 30 to about 95% w/w of the total amount of acarbose (G2 and G2A9 and from 10 to 90% w/w of the total amount of orlistat (G2 and G2B). The release is delayed due to an enteric coating form around the granules, pellets, minitablets etc., i.e. the dissolution of the coating is pH dependent and the enteric coating polymers are chosen so that the coating will not dissolve at pH 4 or less. The granules, pellets and/or minitablets are designed to have an average diameter size of approximately less than 2 mm, such as preferably less than 1.5 mm, at the timepoint when it is supposed to enter duodenum. Once the release starts it is rapid, i.e. without any delay as acarbose and orlistat shall exert their effect in duodenum and jejunum. In this segment of the GI tract a prolonged release of acarbose and orlistat will also take place, but derived from the release of $DR_{DC}$-$PR_{GASTRIC}$ acarbose part described under i) above and $DR_{DC}$-$PR_{GASTRIC}$ or $DR_{EC}$-$PR_{INTESTINAL}$ orlistat part described under iii) below.

iii) a $DR_{DC}$-$PR_{GASTRIC}$ or a $DR_{EC}$-$PR_{INTESTINAL}$ orlistat part, G3, that is designed to release orlistat predominantly in the proximal part of the small intestine until the end of jejunum. Although it is desired that no release take of orlistat takes place in the stomach, it is acceptable that a small amount (0-10% w/w, notably 0-5% w/w) of orlistat may released already in the stomach. Such a part of the composition may be e.g. in the form of granules, pellets, minitablets etc. It contains from about 10 to about 80% w/w of the total amount of orlistat. In this segment of the GI tract a release of acarbose will also take place, but derived from the release of $DR_{DC}$-$PR_{GASTRIC}$ acarbose part described under i) above.

The total amount of orlistat and acarbose, respectively, in the composition is 100% w/w.

The desired release pattern may be obtained in alternative ways, e.g. by use of four different parts as described herein or by use of other formulation principles, e.g. by use of matrix compositions with prolonged release of the drug substance (alternatives to the $DR_{DC}$-$PR_{GASTRIC}$ or $DR_{EC}$-$PR_{INTESTINAL}$ parts). A person skilled in the art will know how to find alternative solutions.

The majority of the dose (>40% of acarbose and >85% of orlistat) is released during neutral condition in the proximal and mid parts of small intestine (mid of jejunum) to avoid pH-dependent degradation in certain regions of the fed stomach. It is important to recognize that the fed stomach only has certain regions that are really acidic (i.e. pH below 3). Otherwise, the pH in the fed stomach will vary between pH 2-6.

Content of Acarbose and Orlistat in the Individual Parts G1, G2 and G3 of a Composition of the Invention:

G1—acarbose content: The content of acarbose in the G1 part of the composition corresponds to from about 5% to about 75% w/w of the total content of acarbose in the composition. In particular, the content of acarbose in G1 corresponds to from about 10 to about 70% w/w of the total content of acarbose in the composition. As appears from the examples herein, G1 may contain from about 15% to about 70% w/w of the total amount of acarbose in the composition, or it may contain from about 30% to about 70% w/w of acarbose in the composition. From the examples herein, it is seen, that many of the G1 parts contain from about 55% to about 70% w/w of the total amount of acarbose in the composition.

G1—orlistat content: The content of orlistat in the G1 part of the composition corresponds to from 0% to about 10% w/w of the total content of orlistat in the composition. Preferably, the content of orlistat in G1 is 0% w/w of the total content of orlistat in the composition.

G2—acarbose content: The content of acarbose in the G2 part of the composition corresponds to from about 30% to about 95% w/w of the total content of acarbose in the composition. In particular, the content of acarbose in G2 corresponds to from about 25% to about 85% w/w of the total content of acarbose in the composition. As it appears from the examples herein, G2 may contain from about 25% to about 70% w/w of the total amount of acarbose in the composition, or it may contain from about 30% to about 60% w/w of acarbose in the composition. From the examples herein, it is seen that many of the G2 parts contain from about 30% to about 45% w/w of the total amount of acarbose in the composition.

G2—orlistat content: The content of orlistat in the G2 part of the composition corresponds to from 10% to about 95% w/w of the total content of orlistat in the composition. Preferably, the content of orlistat in G2 is from about 40% to about 85% w/w of the total content of orlistat in the composition. As appears from the examples herein, G2 may contain from about 60% to about 85% w/w of the total amount of orlistat in the composition, or it may contain from about 70% to about 80% w/w of orlistat in the composition.

As mentioned herein before, G2 may be divided into two separate parts, one containing the acarbose component and the other containing the orlistat component.

G3—acarbose content: The content of acarbose in the G3 part of the composition corresponds to from 0% to about 10% w/w of the total content of acarbose in the composition. Preferably, the content of acarbose in G3 is 0% w/w of the total content of acarbose in the composition. However, as seen from the examples herein, there may be situations where the content of acarbose in G3 is higher such as up to about 40% w/w of the total amount of acarbose in the composition (see Example 3).

G3—orlistat content: The content of orlistat in the G3 part of the composition corresponds to from 10% to about 80% w/w of the total content of orlistat in the composition. Preferably, the content of orlistat in G3 is from about 15 to about 50% w/w of the total content of orlistat in the composition. As appears from the examples herein, G3 may contain from about 15% to about 40% w/w of the total amount of orlistat in the composition, or it may contain from about 15% to about 30% w/w of orlistat in the composition.

The total content of acarbose in the composition is 100% w/w and the total content of orlistat in the composition is 100% w/w.

In the following table is given more details:

|  | G1 - A | G1-O | G2 - A | G2 - O | G3 - A | G3 - O |
|---|---|---|---|---|---|---|
| Comp. 1 | 5-75 | 0-10 | 30-95 | 10-95 | 0-10 | 10-80 |
| Comp. 2 | 10-70 | 0-5 | 25-85 | 40-85 | 0-5 | 15-50 |
| Comp. 3 | 15-70 | 0 | 25-70 | 60-85 | 0 | 15-40 |
| Comp. 4 | 30-70 | 0 | 30-60 | 70-80 | 0 | 15-30 |
| Comp. 5 | 55-75 | 0 | 30-60 | 70-80 | 0 | 15-30 |

A: acarbose
O: orlistat
The figures are % w/w of the total content

Gastrointestinal Brake

The gist of the present invention is based on optimizing the function of the gastro-intestinal brake (GI-brake). The GI brake (as defined in this application) is the sum of various intraluminal nutrient-triggered feed-back systems located throughout the GI tract. GI-break is the primary inhibitory feedback mechanism to control transit of a meal through the gastrointestinal tract in order to optimize nutrient digestion and absorption. The onset of the GI-break also leads, through a sequence of neurohormonal processes, to an increased feeling of satiety and will contribute to reduced ingestion of food. The GI-brake is defined as being comprised of four distinct cell types (located throughout the GI tract), which are the main targets for this invention. Below is a short description of the involved cell types and their hormones (see herein for more details).

1. X/A like cells are found in the fundus area of the stomach. Upon stimulation the secretion of ghrelin is decreased. Ghrelin differs from the other hormones in such that food decreases its secretion, and high ghrelin levels increases appetite. The proposed product is aimed to decrease the activity of the X/A-cell, in other words decrease the secretion of ghrelin.
2. I-cells are located in duodenum and jejunum. Upon stimulation cholecystokinin (CCK) is released. CCK inhibits gastric emptying, gastric acid secretion and stimulates the pancreas to release digestive enzymes. CCK also increases satiety. The proposed product is aimed to increase the activity of the I-cell.
3. K-cells are located primarily in the duodenum but also in jejunum. Upon stimulation GIP is released, which augments insulin secretion and stimulates lipoprotein lipase activity in adipocytes. The proposed product is aimed to decrease the activity of the K-cell.
4. L-cells are located primarily in the distal part of the small intestine, as well as in the proximal colon. Upon stimulation GLP-1, PYY and oxyntomodulin are released. Among others GLP-1 improves glucose homeostasis; GLP-1 and PYY decreases GI motility and inhibits the secretion of digestive enzymes into the lumen; and GLP-1, PYY and oxyntomodulin reduce food intake. L-cells form the more well-known ileal brake. The proposed product is aimed to increase the activity of the L-cell. The L-cell is the proposed product's most important target.

As the L-cells, or the ileal brake, is the most important part of the GI brake, it will be discussed slightly more in-depth. The ileal brake system leads as stated above to decreased appetite and slower GI motility and transit time of chyme[33]. The effect is primarily induced locally in the small intestine by fatty acids, monoacylglycerols and hexoses. These energy-containing nutrients bind to receptors and affect mechanisms on (within) intestinal cells called L-cell (see FIG. 2 for a schematic overview). From these L-cells, signals are generated which enhance fullness, suppress hunger and put a brake on food intake. GLP-1, peptide YY (PYY) and oxyntomodulin are the major hormonal mediators of the ileal brake[31,32, 34]. These three gut hormones are often called incretins, and are gut peptides that affect insulin secretion postprandially. The secretion and the concentration of these hormones, particularly GLP-1 and PYY, increase after GI bypass surgery (GBP) in response to local nutrient stimulation. Another important incretin is glucose-dependent insulinotropic polypeptide (GIP—formerly known as gastric inhibitory polypeptide). The local incretin mediated effect has been estimated to account for 50-70% of total postprandial insulin secretion, and although primarily considered as a response to oral glucose, it may also play a physiological role following lipid ingestion (See below for more on the cell types and hormones involved in the gastro-intestinal brake).

Figure 2:
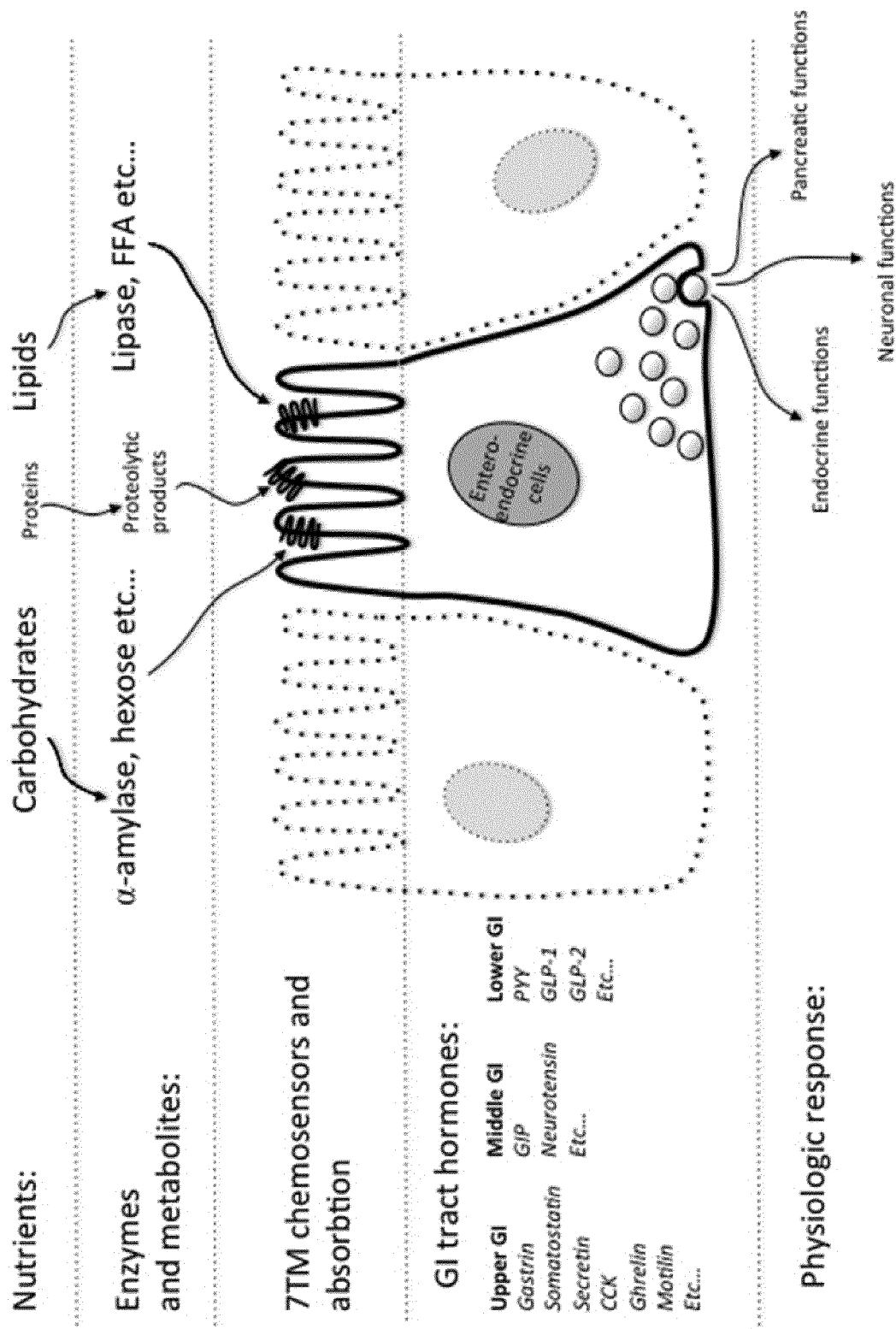

In FIG. 2 it is schematically displayed how the major food components fat, carbohydrate and protein during digestion affect chemosensors on the most important gastrointestinal (GI) brake cells, i.e. the L-cells, in the GI tract. The food components bind to the chemosensors, and certain gut hormones are released. Different hormones are released depending on where in the GI tract the digested food components bind to the chemoreceptors[35].

There are currently several drugs that mimic the GLP-1 increase caused by the ileal brake, such as the injectable drugs liraglutide and exenatide. Exenatide is in late phase clinical trials as antiobesity treatments (Novo Nordisk, National Institute of Diabetes and Digestive and Kidney Diseases), and Saxenda® has recently been approved (see below). These drugs have initially been used as diabetes type-2 medication, but successful weight loss trials have been performed where patients lost more than 8 kg after one year on the highest dose of liraglutide; compared to the placebo group which lost 2 kg[18]. In a recently completed phase III trial evaluating liraglutide 3.0 mg/day vs. placebo for weight maintenance in 422 non-diabetic overweight and obese patients (72% retention), the patients successfully lost ≥5% initial weight during a 4-12 week dietary run-in, and also observed an additional weight reduction of 6.2% in the active treatment group over the ensuing 56 weeks, which ends up in a placebo subtracted-difference of −6.1%[19].

Liraglutide (Saxenda®) was approved, in late 2014 (FDA) and early 2015 (EMEA), for use in adults with a body mass index (BMI) of 30 or greater (obesity) or adults with a BMI of 27 or greater (overweight) who have at least one weight-related condition such as hypertension, type 2 diabetes, or high cholesterol (dyslipidemia).

Orlistat (Tetrahydrolipstatin)

Chemical structure of orlistat ((S)-((S)-1-((2S,3S)-3-Hexyl-4-oxooxetan-2-yl)tridecan-2-yl) 2-formamido-4-methylpentanoate):

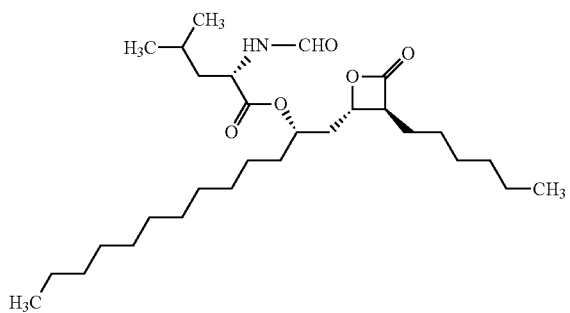 [SMILES: CCCCCCCCCCC[C@@H](C[C@@H]1OC(=O)[C@H]1CCCCCC)OC(=O)[C@H](CC(C)C)NC=O]

Orlistat may be prepared from biological material (*Streptomyces toxytricin*) or it may be prepared synthetically or semi-synthetically.

According to the literature, orlistat appears in two different crystal forms, Form I and Form II. The melting point of Form I and Form II is 44° C. and 43° C. respectively. The product marketed by Roche under the name Xenical® capsules in Sweden contains Form II. No salt forms of orlistat seem to exist. It is practically insoluble in water.

In the present context the term "orlistat" covers the above-mentioned chemical structure as well as any optical isomer thereof as well as any crystal form, any polymorph, any hydrate, any pharmaceutically acceptable or any prodrug thereof.

Orlistat is a local inhibitor of gastric and pancreatic lipases in the GI tract and acts by preventing intestinal absorption of dietary fats through inhibition of luminal digestion. The physicochemical condition in the stomach and along the small intestine is very dynamic and this activity and the inhibition kinetics of orlistat will differ significantly. These dynamic GI conditions are considered in the designs of this fixed oral MR dosage form.

The fraction of the oral orlistat dose absorbed from a conventional dosage form (Xenical®) is low (<3%) and accordingly the plasma exposure is low (<5 ng/ml)[35b]. However, orlistat, although safe, is associated with side-effects that severely hamper compliance. In clinical trials, about 25% or more of the patients complain about GI side-effects including diarrhoea, oily spottings and faecal urgency[35c]. This, in conjunction with the rather modest effect on weight (best case scenario: 10% relative weight loss versus placebo 6% relative weight loss)[23], makes Xenical® less attractive for the vast majority of obese patients. However, in a recent report FDA clearly stated that Xenical® is safe and has clinical benefit[24]. Clinical use of orlistat in an oral modified-release (MR) dosage form does not only decreases fat GI absorption by preventing triglycerides from being broken down to free fatty acids and monoacylglycerols; orlistat also changes GI transit time and affects satiety through many of the cell types mentioned above and below[36].

In the stomach, the reduced lipid digestion caused by orlistat increases gastric emptying (food is delivered faster to the duodenum)[37]. If the meal is high in fat, diarrhoea might occur within 30 min from meal initiation. This diarrhoea is most probably due to the fact that food in the stomach normally triggers emptying of the colon. This signal, in combination with supra-normal amounts of fat in the faeces from previous meals (which leads to less water absorbed during colon transit), may cause the diarrhoea. Possibly, high fat meals will further augment the stomach-to-colon signal, thereby aggravating the situation. As fatty acids, and not intact triglycerides, are the ligands for the receptors in the GI tract, many of the above mentioned hormones will be secreted at a lower level when the digestion of lipids normally occurring in the stomach is inhibited. Of note:

1) In the duodenum, the fatty acid signal to CCK will be weaker, and less bile will be secreted[36], which further decreases fat digestion.
2) The normal meal induced decrease of appetite stimulating hormone ghrelin will be attenuated[36,38].
3) The L-cells (which secretes the incretins) will also secrete less GLP-1, leading to a smaller ileal brake[36].

The undigested triglycerides will enter the colon, and, as mentioned above, fat only enters colon in small amounts. Larger amounts of fat will lead to faster propulsion through the colon and less water will be absorbed. In summary, the current way of delivering orlistat in conventional dosage form (that includes drug release in the stomach) to the GI tract on the one hand removes calories in the form of intact undigested triglycerides, but on the other hand causes a lot of side effects and bypasses many of the appetite adjusting systems in the GI tract and also increases gastric emptying rate which in fact reduces the feeling of fullness and increases appetite[36].

Acarbose

Chemical structure of acarbose (O-4,6-Dideoxy-4-[[(1S,4R,5S,6S)-4,5,6-trihydroxy-3-(hydroxymethyl)cyclohex-2-enyl]amino]-α-D-glucopyranosyl-(1→4)-O-α-D-glucopyranosyl-(1→4)-D-glucopyranose:

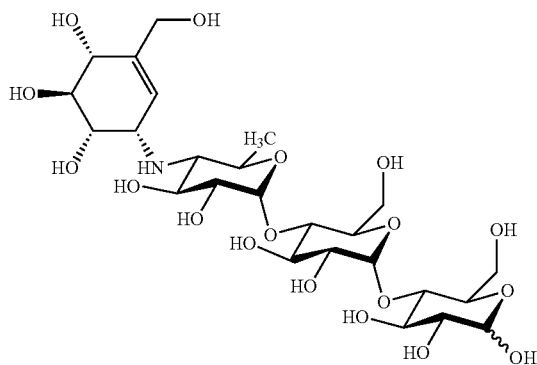

Acarbose may be prepared from biological material (Actinoplanes) or it may be prepared synthetically or semi-synthetically.

No information about the crystal form of acarbose could be found in the literature. However some sources indicate that acarbose may be amorphous and no salt forms of acarbose seems to exist. According to Ph. Eur. it is very soluble in water.

In the present context the term "acarbose" covers the above-mentioned structure as well as any optical isomer thereof as well as any crystal form, any polymorph, any hydrate, any pharmaceutically acceptable or any prodrug thereof.

Acarbose (Glucobay®) is a competitive α-glucosidase and pancreatic α-amylase inhibitor, which inhibits the hydrolysis of oligosaccharides during GI luminal digestion of a meal[25]. Acarbose is currently used as a diabetic drug, mainly in Asia, but only scarcely in Western countries. By inhibiting the luminal digestion and subsequent absorption of carbohydrates, the concentrations of glucose in blood sugar increases slower postprandially, and the patient's insulin need is reduced[40]. The low intestinal permeability of acarbose (due to its hydrophilic properties) leads to less than 5% of the drug being absorbed after oral administration[41]. The low GI absorption and bioavailability results in very low plasma exposure, which makes acarbose considered as a safe drug without systemic side-effects[25]. As with orlistat, a large part of the patients using acarbose reports GI tolerability problems (mainly flatulence, diarrhea as well as GI and abdominal pains)[25], which limits its current clinical use in Western countries. The magnitude of GI side effects is directly associated with the strength of the oral dose, in a stepwise manner[42]. Furthermore, the acarbose side effects seem also to be "diet driven". The higher consumption of carbohydrates, and perhaps slightly more "resistant" carbohydrates (with a slightly slower digestion), in Asian countries seems to reduce the side-effect rate[43,44]. Moreover, patients are recommended to slowly introduce acarbose by using 50 mg per day during 1-3 week time and then slowly increase the oral dose up to 100 mg per meal[45]. As more undigested carbohydrates reach further down in the GI tract, more enzymes are being produced locally in the distal small intestine to deal with the undigested carbohydrates[46]. Although acarbose also removes ligands from various cell types throughout the GI tract, some noteworthy differences are observed. Acarbose will reduce gastric emptying rate, possibly by delivering less ligands to GIP secreting K-cells in the proximal small intestine, and more ligands to distal GLP-1 secreting L-cells. Acarbose will also cause more undigested polysaccharides to enter the proximal colon, where bacteria will ferment the polysaccharides, and the resulting short chain fatty acids can bind to L-cells and augment the ileal brake.

Orlistat and Acarbose—Current Effects on GI Brake

Despite that especially Xenical® but also Glucobay® to some degree remove ligands for the various appetite adjusting systems in the GI tract, both have been shown to increase the incretin response after meals[46]. Noteworthy is that the results are more consistent with Glucobay®[37,47]. One plausible reason for this is that orlistat at high dose inhibits the gastric and pancreatic lipases semi-reversibly[48], which leads to intact triglycerides passing through the ileum. As these undigested triglycerides are poor ligands for the receptors (FFA1-3) on the L-cells, there will be a poor or non-existent ileal brake response[49]. The irreversibility of orlistat is affected by the composition and size of the fat droplets, which in turn is greatly influence by the endogenous secreted bile salts.

Acarbose on the other hand binds and inhibits the enzymes to a lesser degree, enabling carbohydrates to be digested and glucose to be formed throughout the GI tract[50]. The side-effects originate from bacterial fermentation of the undigested carbohydrates in the colon, although this fermentation also gives rise to short-chain fatty acids (SCFA)[50]. This formation has multiple positive nutritional values such that SCFAs act as ligands for L-cells in the colon (see above).

Clinical studies also show a small weight loss, about 1% relative weight loss, after 12 months treatment of 600 mg acarbose per day[51] after use of acarbose, primarily in Asian populations[43,44].

How to Optimize the GI Brake by Using Orlistat and Acarbose

The main idea regarding an oral modified-release (MR) pharmaceutical composition of the invention is to reduce pH-dependent degradation of both APIs, slow down GI transit time, increase satiety and reduce weight. To achieve that, orlistat and acarbose have to be released with regard to the acidic luminal pH, the digestive enzyme activity and the epithelial cell types in the GI tract. The overall medical objective is to have clinical meaningful amount of hexoses (especially glucose) and free fatty acids/monoacylglycerols formed at specific points in the GI tract and absorbed in the distal ileum. Starting in the stomach, where the overall orlistat release should be very low or absent, as orlistat increases gastric emptying (mechanism described above). Acarbose, on the other hand will have one part of the total dose designed to be released rapidly in the intestines, but only slowly in the stomach in order to ensure that the gastric mixing with gastric content should be as thoroughly as possible. This is expected to provide an increased effect and reduced side effects[52]. It is expected that the formulation components, with both orlistat and acarbose, should be mixed as properly as possible with food irrespectively where the drug is released as it would optimize the effect and reduce the side-effects. The pH-dependent degradation has been one of the major reasons for the design as enteric coated pellets of both APIs. The majority of the dosage form (>60% of acarbose and >90% of orlistat) is released during neutral condition in the proximal and mid parts of small intestine (end of jejunum) to avoid pH-dependent degradation in certain regions of the fed stomach. It is important to recognize that the fed stomach only has certain regions that are really acidic (i.e. pH below 3). Otherwise the pH in the fed stomach will vary between pH 2-6.

As the food (chyme) with this oral MR formulation properly mixed enters the duodenum, a large part of the total dose orlistat is designed to be released, to counter the vast secretion and activity of pancreatic lipase. Also acarbose is designed to be released in sufficient quantities to minimize the amount of glucose reaching the K-cell (see below), thereby minimizing GIP release. Then, as the food (chyme) passes through jejunum, lower release rates of orlistat as well as acarbose are designed in the novel oral MR formulation. At the distal jejunum and proximal ileum, the concentration of L-cells becomes denser and the concentration of K-cells becomes sparser. From now on, digestion of triglycerides and polysaccharides is optimal and there is no further orlistat or acarbose released in this intestinal region. The highest concentration of L-cells is in the distal ileum and proximal colon, which is the conceptual target for the main mechanisms of this anti-obesity product. The objective is to have 1-20% or 5-20% of the orally ingested fat and carbohydrates available for digestion in ileum and consequently enough ligands for a clinically meaningful ileal brake.

As seen from the above, it may be advantageous to combine orlistat and acarbose in an oral MR product to ensure triggering of the GI brake, but to be successful many factors have to be taken into account inter alia the physicochemical properties of the two APIs, the presence of the relevant enzymes in different parts of the GI tract, the inhibition mechanisms and kinetics in the various parts, the influence of the two APIs on the emptying rate of the stomach chyme in postprandial condition, the influence of the two APIs on the presence of the substances that trigger the GI brake etc. Although the effect on the GI brake is hypothesized to be stronger with the combination of acarbose and orlistat, the modified release of acarbose and orlistat should have an effect by themselves but to lesser degree on the GI brake.

The enteroendocrine system plays a fundamental role in orchestrating post-prandial physiology, and is central to the regulation of glucose homeostasis and satiety. The success of current GLP-1-based therapies and the dramatic effects of bariatric surgery on insulin secretion and appetite greatly support the future development of therapeutic strategies that exploit targets upstream of enteroendocrine secretion as novel treatments for type 2-diabetes and obesity. Despite the notable progress made to date in dissecting the mechanisms of stimulation-coupled enteroendocrine secretion, there are currently no drugs clinically approved that directly target endogenous enteroendocrine cells. The unexpected success of bariatric surgery in treating type 2-diabetes, however, highlights the benefits that could be achieved through a gut-based therapeutic approach.

In the following section a brief description is given of the normal digestion of fat and carbohydrates and of the cell types involved.

Human GI (GI) Digestion

The human GI digestion of ingested food is characterized by a large overcapacity for absorption and built-in redundancy. Several different GI-located systems coexist to make sure that adequate energy is ingested and digested. This section will briefly describe the normal digestion of fat and carbohydrates (CHO).

Fat Digestion

Already in the mouth some limited lipid digestion starts but is considered as minor contribution of the overall lipid digestion. Triglycerides are hydrolysed into fatty acids and diacylglycerols by lingual lipase(s). As the food is swallowed, lingual lipase continues to, now assisted by gastric lipase, to digest triglycerides into fatty acids and diacylglycerols. Up to 15-30% of the ingested triglycerides may be partially digested by these two enzymes before emptied into the proximal small intestine. Big fat droplets start being broken down into smaller droplets by the churning of the stomach. The first fatty acids that are emptied from the stomach into to duodenum bind to receptors on special enterocyte cells called I-cells. These I-cells then release a specialized local GI hormone named cholecystine kinase (CCK, see below). CCK in turn stimulates bile secretion from the gall bladder in the liver at the same time as it releases pancreatic enzymes. Bile acids break big fat droplets into smaller droplets, and keep the small droplets from coalesce (emulsification). Pancreatic lipase, released from pancreas in vast quantities, will rapidly digest the triglycerides that are emptied from stomach. Triglycerides from the small fat droplets continue to break down. Bile acids form small micelles, containing free fatty acids and monoacylglycerol. These small micelles can then bind to the enterocytes and the fatty acids and monoacylglycerols are absorbed as monomers. In the duodenum and the proximal jejunum, almost all fatty acids are released and absorbed as monomers. Some fatty acids bind to K- and M-cells along the intestine, which leads to hormonal response (see cell types above and below). As the food enters the ileum, most fatty acids have been absorbed and very little (~5%) undigested fat enters proximal colon. Any unabsorbed fatty acids can bind to receptors on L-cells and give potent hormonal response—the ileal brake (see above). Any undigested triglycerides will pass through colon unaltered, normally only around 3-5% of ingested fat.

Carbohydrate (CHO) Digestion

A limited digestion of carbohydrates starts in the mouth (about 5% of ingested starch) as α-amylase hydrolyses polysaccharides into oligosaccharides. This digestion of polysaccharides continues after the food has been swallowed until α-amylase is blocked by low gastric pH. About 30% of ingested starches may be digested during this period. When chyme enters the duodenum pancreatic α-amylase is released; and almost all polysaccharides are hydrolysed to oligosaccharides (maltose is the dominating oligosaccharide). If CHO content of diet is dominated by unrefined CHO (resistant starch), the hydrolysis is somewhat delayed. The oligosaccharides are then hydrolysed by oligosaccharidases lining the enterocytes to monosaccharaides (glucose is the dominating monosaccharide). The major part of the monosaccharaides is absorbed (co-transported with sodium) in the small intestine. Monosaccharides bind to K- and M-cells, which leads to hormonal response (see below for description of cell types). Peak concentration of oligosaccharides in the small intestinal lumen occurs in the distal part of duodenum and proximal jejunum. Polysaccharides continue to be cleaved by amylases to monosaccharaides. The majority of CHO has been absorbed before food leaves jejunum. Monosaccharaides may bind to L- and M-cells (see below) in the jejunum. In the ileum, very little monosaccharides remain to be absorbed here, unless diet has a high amount of more resistant CHO. Unabsorbed monosaccharaides may bind to receptors on L- and M-cells and give rise to an incretin response. Undigested resistant starch and fibre will enter proximal colon. Some resistant starch and soluble fibre are broken down to monosaccharaides, but most are being fermented into short chain fatty acids. The short chain fatty acids may bind to receptors on L-cells and give rise to an incretin response.

Short Description of Some of the Involved Cell Types and their Hormones

X/A like cells are found in the fundus area of the stomach. Upon stimulation from mainly glucose, and to smaller degree fatty acids, the secretion of ghrelin is decreased. Ghrelin differs from the other hormones in such that food decreases its secretion, and high ghrelin levels increases appetite. X/A-cells are antagonists to the gastro-intestinal brake and the proposed product is aimed to decrease the activity of the X/A-cell, in other words decrease the secretion of ghrelin.

D-cells are located in the stomach, but also in other part of the GI system. Upon stimulation somatostatin is released. Somatostatin is the inhibitory "hormone" and suppresses the release of GI hormones such as: Gastrin, Motilin, VIP, GIP and GLP-1, as well as insulin and glucagon. Increased somatostatin leads to decrease rate of gastric emptying, and reduces smooth muscle contractions and blood flow within the intestine.

I-cells are located in duodenum and jejunum. Upon stimulation from fatty acids and amino acids, CCK is released. CCK inhibits gastric emptying, gastric acid secretion and stimulates the pancreas to release digestive enzymes. CCK also increases satiety. As the levels of the substances that stimulated the release of CCK drop, the concentration of CCK drops as well. The release of CCK is also inhibited by somatostatin and pancreatic peptide (PP). I-cells are part of the GI brake and the proposed product is aimed to increase the activity of the I-cell.

K-cells are located primarily in the duodenum but also in jejunum. Upon stimulation from mainly glucose, and a lesser degree from fatty acids, GIP is released, which augments insulin secretion. GIP also stimulates lipoprotein lipase activity in adipocytes. Several studies show that GIP concentration is positively associated with obesity. GIP knockout mice are "obesity resistant". K-cells are antagonists to the GI brake and the proposed product is aimed to decrease the activity of the K-cell.

S-cells are located primarily in the duodenum but also in jejunum. When the chyme enters the duodenum, the pH drops and Secretin is released. Secretin stimulates bicarbonate secretion and inhibition of gastric acid secretion, colonic contraction, and motility.

M-cells are located primarily in the duodenum. Here motilin is secreted. Motilin increases GI motility and stimulates the production of pepsin. A high level of motilin secreted between meals into the blood stimulates the contraction of the fundus and antrum and accelerates gastric emptying. Motilin stimulates gallbladder emptying and increases the squeeze pressure of the lower esophageal sphincter. Motilin stimulates the release of pancreatic polypeptide and somatostatin.

L-cells are located primarily in the distal part of the small intestine, as well as in the proximal colon. Upon stimulation from monosaccharaides, free fatty acids and amino acids; GLP-1, PYY and oxyntomodulin are released. Also, in colon short fatty acids from bacterial fermentation of non-digested oligosaccharides can stimulate the L-cells. GLP-1 improves glucose homeostasis by increasing insulin secretion during meals. GLP-1 also suppresses glucagon secretion. GLP-1 and PYY decreases GI motility and inhibits the secretion of digestive enzymes into the lumen. Plasma GLP-1 increases sooner during carbohydrate than during fat ingestion probably due to stimulation of sweet taste receptors on the tongue initiating a neural reflex to the L cells. GLP-1, PYY and oxyntomodulin reduce food intake. L-cells are part of the GI brake (main component of ileal brake) and the proposed product is aimed to increase the activity of the L-cell. The L-cell is the proposed product's most important target.

In addition to the above-mentioned cell types that can be found throughout the GI tract, hormones are secreted from the pancreas. Apart from glucagon and insulin, two other hormones are important to mention: vasoactive intestinal peptide (VIP) and pancreatic polypeptide (PP). VIP has an important immunomodulatory role. In the GI-tract, VIP stimulates the secretion of water and electrolytes into the chyme, as well as stimulating contraction of enteric smooth muscle, stimulating pancreatic bicarbonate secretion, and inhibiting gastrin-stimulated gastric acid secretion. All these effects work together to increase GI motility. PP is secreted by PP cells in the islets of Langerhans. Plasma concentrations are maximal after meals, in proportion to the quantity of energy consumed. PP down-regulates the secretion of CCK and high concentrations decrease appetite.

COMPOSITIONS OF THE INVENTION

As mentioned above, the invention provides:
i) A composition comprising both orlistat and acarbose—the composition may be composed of different parts such as granules, coating layers, minitablets etc.
ii) A composition comprising orlistat, but not acarbose—the composition may be composed of different parts such as granules, coating layers, minitablets etc.
iii) A composition comprising acarbose, but not orlistat—the composition may be composed of different parts such as granules, coating layers, minitablets etc.

In the following, the description is focused on a composition comprising both orlistat and acarbose. However, in order to arrive at a composition of the invention comprising orlistat and not acarbose, such a composition is achieved by leaving the out acarbose in general and if acarbose is present in a specific part, where orlistat is not present, then this part should be left out. The same applies to a composition of the invention comprising acarbose and not orlistat. Such a composition is achieved by leaving out orlistat in general and if orlistat is present in a specific part, where acarbose is not present, then this part should be left out.

A composition of the invention is designed to release orlistat and acarbose at different rates and locations along the GI tract to achieve a sufficient effect on metabolic control (for example weight management as well as glucose and lipid homeostasis) and to reduce side-effects and increase tolerability. Moreover as discussed in the preceding paragraphs, it is important to ensure that the GI brake is triggered, i.e. to ensure that orlistat and acarbose is not degraded in the acidic regions in the postprandial stomach and do not hamper digestion to such a degree that limited amounts of glucose and fatty acids are available to trigger the GI brake.

Formulation of the G1, G2 and G3 Parts of the Composition

The G1 part of the composition is designed to release acarbose in a prolonged manner. The prolonged release is obtained by providing a G1 part that contains acarbose and a prolonged release polymer or a lipid. The prolonged release polymer typically has a poor water-solubility, ie it is a hydrophobic polymer, and may be selected from the group consisting of ethylcellulose, acrylates or acrylic acid derivatives, gelatin, coating agent selected from the group consisting of co-polymers based on polymethacrylic acid and methacrylates, ethyl acrylate and methyl acrylate, co-polymers of acrylic and methacrylic acid esters, hydroxypropyl methylcellulose phthalate, cellulose acetate phthalate, polyvinyl acetate phthalate or mixtures thereof. The lipid may be selected from fatty acids and/or esters, fatty alcohols, cetyl alcohol, stearyl alcohol, mineral oils, hydrogenated vegetable oils, vegetable oils, acetylated hydrogenated soybean oil glycerides, Castor oil, preferably solid at room temperature, most preferably hydrogenated vegetable oil.

The hydrophobic polymer or lipid is typically present in G1 in a concentration of from about 10% to about 50% w/w such as from about 15% to about 45% w/w or from about 20 to about 40% w/w of the total weight of G1.

The hydrophobic polymer or lipid may be substituted by or supplemented with hydroxypropylmethylcellulose or a wax such as, e.g. glycerol monostearate, white wax, carnauba wax, stearyl alcohol, stearic acid, polyethylene glycol and triglycerides or mixtures thereof.

Hydroxypropylmethylcellulose or wax is typically present in G1 in a concentration of from about 10% to about 50% w/w such as from about 15% to about 45% w/w or from about 20 to about 40% w/w of the total weight of G1.

The G2 part of the composition is designed to have a delayed release of acarbose and orlistat, but once release starts then it is relatively rapid. This release pattern is obtained by combining the drug substances with one or more surfactants (especially in order to increase the solubility of orlistat) and an enteric polymer, i.e. a polymer that has a pH dependent solubility such that it is not soluble at low pH (normally at pH 4 or less), but soluble at neutral/alkaline pH.

The polymer may be incorporated into the formulation of G2 or it may be used as a coating material to coat the G2 formulation.

The surfactant is typically selected from the group consisting of anionic, cationic or non-ionic surfactant. Non-ionic are e.g., polysorbate 20, polysorbate 21, polysorbate 40, polysorbate 60, polysorbate 61, polysorbate 65, polysorbate 80, polysorbate 81, polysorbate 85, polysorbate 120, sorbitan monoisostearate, sorbitan monolaurate, sorbitan monopalmitate, sorbitan monostearate, sorbitan monooleate, sorbitan sesquioleate, sorbitan trioleate, glyceryl monooleate and polyvinylalcohol. Anionic surfactants include docusate sodium and sodium lauryl sulphate. Cationic surfactants includes e.g. benzalkonium chloride, benzethonium chloride and cetrimide.

The total concentration of surfactants is typically present in G2 in a concentration of from about 0.5% to about 30% w/w of the total weight of G2. Preferably, the concentration is from about 1% to about 10% w/w such as from about 1% to about 8% w/w.

The enteric polymer is typically an acrylate or acrylic acid polymer or co-polymer. The acrylic polymer may comprise one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

The acrylic polymer may be used in the form of an acrylic resin lacquer used in the form of an aqueous dispersion, such as that which is commercially available from Rohm Pharma under the tradename Eudragit® or from Colorcon under the tradename Acryl-EZE®. The acrylic coating may comprise a mixture of two acrylic resin lacquers commercially available from Evonik under the tradenames Eudragit® RL 30 D and Eudragit® RS 30 D, respectively. Eudragit® RL 30 D and Eudragit® RS 30 D are copolymers of acrylic and methacrylic esters with a low content of quaternary ammonium groups, the molar ratio of ammonium groups to the remaining neutral (meth)acrylic esters being 1:20 in Eudragit® RL30 D and 1:40 in Eudragit® RS 30 D.

Eudragit® RL/RS mixtures are insoluble in water and in digestive fluids. However, coatings formed from the same are swellable and permeable in aqueous solutions and digestive fluids. The Eudragit® RL/RS dispersions may be mixed together in any desired ratio in order to ultimately obtain a modified release formulation having a desirable dissolution profile.

The enteric polymer may also be a coating agent selected from the group consisting of co-polymers based on polymethacrylic acid and methacrylates, ethyl acrylate and methyl acrylate, co-polymers of acrylic and methacrylic acid esters, hydroxypropyl methylcellulose phthalate, cellulose acetate phthalate, polyvinyl acetate phthalate or mixtures thereof.

In the G2 part, the enteric polymer is typically present in a concentration of from about 15 to about 50% w/w based on the total weight of the G2 formulation. It is preferred that the concentration is from about 15% to about 40% w/w or from about 20% to about 40% w/w. As it specifically appears from Examples 1E, 2D, 4F, 4Q, 5D many other pharmaceutically acceptable excipients may be included in the G1, G2 or G3 formulations.

The G3 part is designed to release orlistat in a prolonged manner. Orlistat may be release at a low degree already in the stomach. Orlistat is very poor water-soluble and in order to achieve the desired release, orlistat is combined with one or more surfactants. The surfactant may be one or more of those mentioned above under G2. The surfactant is present in G3 in a concentration from about 1% to about 30% w/w of the total weight of the G3 formulation. Preferably, it is present from about 2% to about 20% w/w or from about 3% to about 20% w/w.

Alternatively or additionally, the release of orlistat from G3 can be obtained by incorporation of a water-soluble or water-swellable polymer such as hydroxypropylmethylcellulose or other cellulose derivatives like eg methylcellulose, carboxymethylcellulose, hydroxypropylcellulose.

Such a water-soluble polymer is typically incorporated into the G3 formulation in a concentration of from about 70 to about 90% w/w based on the total weight of G3. Preferably, the concentration is from about 80 to about 90% w/w.

The G1, G2 (or G2A, G2B) and G3 parts may also contain other pharmaceutically acceptable ingredients selected from those mentioned herein. Moreover, in order to manufacture a final composition G1, G2 (or G2A, G2B), and/or G3 may be admixed with one or more pharmaceutically acceptable excipient or may be G1, G2 (or G2A, G2B), and/or G3 coated eg with a film coating or with a coating that hinders or reduces negative impact of one part to another part.

The part G1 of the composition may be in the form of granules, pellets, minitablets etc. or part G1 is incorporated into a two-layer tablet, where part G1 is contained in one of the two layers. The layer containing part G1 may be provided with a delayed release coating.

Part G2, or G2A and G2B, of the composition may be in the form of granules, pellets, minitablets etc. containing an enteric polymer or provided with an enteric coating, or G2, or G2A and G2B, is incorporated into a two-layer tablet, where part G2, or G2A and G2B, is contained in one of the two layers and the layer containing part G2, or G2A and G2B, is provided with an enteric coating.

Part G3 may be in the form of granules, pellets, minitablets etc. or it is contained in a two layer tablet, wherein part G3 is contained in one of the two layers.

The final modified-release composition according to the invention may be in the form of a multiple-unit tablet, a bi-layer multiple-unit tablet, a coated tablet, a multiple-unit capsule or a multiple-unit oral powder. Typically, G1, G2, or G2A and G2B, and G3 are in the form of pellets, granules, spheres or the like, and the modified-release composition according to the invention is in the form of a multiple-unit tablet, capsule, sachet or powder.

To assist in the design of when and where in the GI tract orlistat and acarbose should be released from a MR composition of the invention, an in silico simulation model has been used in the theoretical predictions, which is described in the following.

In-Silico Simulation of the Absorption Process from the GI Tract to Guide Choosing the Composition and Dose Distribution.

Accurate and reliable in silico prediction of GI absorption for novel active pharmaceutical ingredients (API) is a major challenge and of great importance in the drug discovery and pharmaceutical product development. A semi-physiological in silico model (performed via computer simulation) was developed based on clinical and literature data for both APIs (orlistat and acarbose), GI physiology and biochemistry (see the description herein). The principles of the modelling and simulation in the GI tract are displayed in FIG. 3.

Biopharmaceutical simulation of GI processes deploy a modified version of the Compartmental Absorption and Transit model (CAT) for the GI tract along with a one-compartmental pharmacokinetic model to describe the local GI concentration-time profile of any of the two APIs (orlistat and acarbose). The stomach and the small intestine are modelled as compartments coupled in series. Originally, CAT depicts the small intestines (SI) by 7 compartments whereas the adopted GI-model deploys 1 compartment for the stomach and 6 compartments for the small intestine transit, respectively[53]. Physiological parameters for the different regions such as volumes, areas, transit times and pH in the intestinal media were adopted as proposed[54]. To better describe the physiologic gastric emptying during fed conditions, the stomach transit was described by a 30 min lag phase followed by an emptying rate equal to 0.5% of the initial volume per min (zero-order process)[55]. The intraluminal content (i.e. dissolved API, product components) flows from one compartment to the next bringing dissolved matter, particles and formulation. In contrast, bile salt micelles and local digestion enzyme activity and inhibition are modelled with a time-constant concentration in each compartment. Each compartment is assumed to be ideal, i.e. concentrations, pH etc. have the same value everywhere. The compartments have various pH values and thus the solubility of ionisable drugs changes along the GI tract.

For an ideal GI compartment with transit time $\tau$, the amount of substance leaving the GI compartment during unit time is $$F_{outflow} = X/\tau \qquad \text{(Equation 1)}$$

where X is the amount of each API present in the GI compartment. The outflow of drug from one compartment goes directly into the next one. However, there is an implicit uptake of water in each tank so the volumetric flow is reduced along the GI tract. In addition to the flow to next compartment there are other dynamic processes occurring in each GI compartment. Particles may dissolve or grow, dissolved drug may be distributed to lipid particles and/or bile salt micelles, bound to enzymes, released from enzymes or be absorbed through the gut wall. In this model dispersed system has been simulated. However, the model assumed no backflow from the intestinal wall, i.e. once absorbed into the intestinal epithelial wall the drug cannot be distributed back to the intestinal compartments.

The areas available for absorption in the GI compartments were calculated from the respective volume and a mean radius (weighted by the segments length) of 1.15 cm. This approach was based on the assumption that the fluid in the GI tract is distributed as small segments from where the absorption occur, i.e., there are parts along the intestine with no fluid where no absorption take place. Also, even if the gut can be depicted as a tube, certain structures, such as folding, villi and microvilli, affect the available area for absorption. This was accounted for in this GI-model by using an area amplification factor ranging from 3 to 1, proximal to distal, in the small intestine as previously stated to be physiologically relevant[54].

The flow from an intestinal compartment, i.e. compartment 2 to 7, over the apical membrane is proportional to the intestinal permeability, the free monomer concentration in the bulk, and the surface area available for absorption.

The data analysis of the observed in vitro and simulations of GI processing of the formulation and each of the two API concentration-time profiles (acarbose and orlistat) in the different GI compartments are shown in FIGS. 4 and 5. The observed in vitro release data demonstrate that the fixed-dose oral modified-release dosage form provide the designed release profiles of acarbose and orlistat. The simulations performed with the described mathematical model, based on the observed in vitro release, demonstrate that the fixed-dose oral modified-release dosage form provide the targeted concentration-time profiles of acarbose and orlistat along the GI tract that will optimize the safety and effect properties of the fixed dose combination of acarbose and orlistat in this designed modified-release oral dosage form. If only the curves for acarbose or orlistat, respectively, are considered, these curves are mathematical modelling for an acarbose-containing composition of the invention (i.e. without orlistat) or an orlistat-containing composition of the invention (i.e. without acarbose).

Compositions

Compositions of the invention have been developed based on research involving characterization and identification of the impact of both physical form of the two APIs (i) and formulation technology (ii) on the GI absorption, bioavailability, digestive physiology and local effects. These factors determine the local concentration-time profile of both APIs along the GI tract, which determine the effect and side-effect panorama. The GI luminal composition, volumes of the GI fluids and hydrodynamic conditions generated by the GI motility which are controlled by endocrine and neural factors, also influence drug release and dissolution. However, the effect of dissolution on GI absorption is also modulated by a plethora of other factors involved in the drug absorption process as described by Sjögren et al in 2014[56]. For instance, the overall impact of dissolution on GI drug absorption is strongly influenced by the effective intestinal permeability ($P_{eff}$), most likely mediated by improved sink condition[57,58]. In a similar fashion, capacity limited processes such as intestinal degradation and/or complexation, carrier-mediated transport and/or efflux processes through the intestinal wall, metabolism in the intestinal mucosa, and lymphatic transport must all be considered to determine the impact of drug form and formulation on absorption and bioavailability. Moreover, many of these key processes are GI region specific. The pH dependent degradation of both orlistat and acarbose in the acidic regions of the postprandial stomach has been reduced significantly by the design of multiple pellets with enteric-coated polymer(s). The multiple-unit design of the MR formulation will optimize the gastric mixing and reduce the intra- as well as the inter-individual variability in gastric emptying.

Thus, in order to predict the influence of APIs' physical form (i) and formulation technologies (ii) on GI drug absorption all of the factors described need to be taken into consideration. Compositions of the present invention have been developed based on an integrated approach, which considers the interplay among the above mentioned factors in order to establish the optimal dose and drug release properties to maximize the effect on the GI brake (and subsequent metabolic control management) by affecting the luminal digestion of carbohydrates and lipids in stomach, duodenum, jejunum, ileum and colon.

Biopharmaceutical properties of each API are central for the design of a fixed oral combination modified release (MR) products that has the main objective for optimizing the GI brake mechanisms. The selection of a product design providing optimal clinical properties for these indications (i.e. obesity, weight reduction and treatment of type 2-diabetes), the maintenance of defined local exposure-time profile in target patient group(s), the generation of low systemic exposure-time (which should be low for this fixed oral combination product intended for local effect) are key for a successful product development in this case[59]. Finally, the need to link formulation and manufacturing to clinical performance has received increased emphasis with the introduction of quality-by-design (QbD) principles[60,61].

These two APIs, acarbose and orlistat, which exhibit challenging biopharmaceutical properties, e.g. pH dependent degradation in acidic conditions, huge difference in lipophilicity, low aqueous solubility, sometimes in combination with limited intestinal $P_{eff}$, often require complex formulation strategies to enable successful local concentration time profile in the GI tract that may optimize the GI brake mechanism, side-effect intensity and frequency, clinical efficacy and patient compliance. The pharmaceutical product development aimed to optimize the local GI concentration time profile and inhibition of digestive enzymes throughout the stomach and small intestine as well as to some extent in the large intestine. A key to a successful development is that sufficient amounts of lipids and carbohydrates are digested and absorbed as hexoses and free fatty acids in the ileum to stimulate a strong ileal brake mechanism. In those cases, where acarbose is the sole drug substance, a key to success is that sufficient amounts of carbohydrates are digested and absorbed as hexoses in the ileum to stimulate a strong ileal brake, and in those cases where orlistat is the sole drug substance, lipids must be digested to fatty acids. This can only be achieved by establishing a balance between drug release, gastric stability, solubility, precipitation, enzyme inhibition and drug absorption. Oral MR dosage forms might be based on high energetic solid-state forms of the API, reduction of the API particle size (sometimes as far as the nanoscale), lipid formulations or soluble drug complexes[62].

The design and development of such oral MR formulations have been supported by use of biopharmaceutical simulations of the dynamic interplay between biopharmaceutical, pharmaceutical and GI-physiological factors. In the FIGS. 4a, 4b, 5a and 5b the total luminal monomer concentration of orlistat and acarbose, respectively, shows the most likely regional intra intestinal monomer drug amount-time profile over 5 hours and 10 hours post dosing, respectively. The appearance rate of drug monomers in the lumina) bulk was determined by the designed drug release rate from the formulation in these simulations.

As mentioned herein before, the present invention provides an oral MR composition comprising orlistat and acarbose, wherein the composition contains individually distinct parts with different release pattern. The composition typically contains three or four different parts:
i) a first part, G1, targeted for a delayed release in the stomach and prolonged release in the small intestine and containing from 5 to 70% w/w of the total amount of acarbose,
ii) a second part, G2 or G2A and G2B, targeted for a release in the proximal small intestine and containing from 10 to 90% w/w of the total amount of orlistat and from 30 to 95% w/w of the total amount of acarbose, and
iii) a third part, G3, targeted for a release in the proximal small intestine containing from about 10 to about 80% w/w of the total amount of orlistat, and
the total amount of orlistat and acarbose, respectively, in the composition is 100% w/w.

As apparent from the disclosure herein part ii) may be divided into two separate parts, one containing orlistat (G2B) and the other containing acarbose (G2A).

As seen from the disclosure herein and the examples, the various parts of the composition may be obtained in many different ways. All possibilities are within the scope of the present invention.

The target release profile may be achieved by using three different granules (or pellets or minitablets) containing acarbose or orlistat or both APIs:

Granules or part of the composition containing acarbose
1. $DR_{DC}$-$PR_{GASTRIC}$ (Delayed release by "delayed coating" (DC), prolonged release starting in the stomach). Denoted as Granule 1 or G1.
2. $DR_{EC}$-$RR_{PROX\ SI}$ (Delayed release by enteric coating (EC), rapid release in the proximal small intestine). Denoted as Granule 2 or G2 or G2A.

Granules or part of the composition containing orlistat
3. $DR_{EC}$-$RR_{PROX\ SI}$ (Delayed release by enteric coating (EC), rapid release in the proximal small intestine). Denoted as Granule 2 or G2 or G2B.
4. $DR_{DC}$-$PR_{GASTRIC}$ and/or $DR_{EC}$-$PR_{INTESTINAL}$ (Delayed release by "delayed coating" (DC) or enteric coating (EC), prolonged release predominantly in the proximal intestine). Denoted as Granule 3 or G3.

In those cases, where the final composition is not composed of different granules, pellets, minitablets or the like, but where the composition is in the form of a coated tablet, the G1 part is typically a coating containing acarbose for relatively slow release, the G2 part is typically an enteric coating containing acarbose and orlistat for rapid release of acarbose and orlistat in the small intestine and the G3 part is for slow release of orlistat in the small intestine. As seen from the examples herein, an amount of acarbose may also be included in G3. Thus, such a composition typically has a core, which is the G3 part. The core is coated with an enteric coating, which is the G2 part, and on top of this enteric coating is a further coating provided, which is the G1 part. Between the core and/or between the coating layers, a further coating may be provided to protect either the core or the topcoating for any degradating effect caused by the enteric coating materials contained in the G2 part.

G1 and G3 are designed to have a prolonged release (PR) of orlistat and/or acarbose starting in the stomach, optionally with up to 40 minutes delay, such as preferably 20-40 minutes delay. G2 is a combination of both acarbose and orlistat and is designed to be gastro-resistant (enteric coated) and to release orlistat and acarbose rapidly after entering the duodenum and proximal small intestine due to the change in pH from the acid condition in the stomach to the neutral condition in the small intestine. G1 and G3 are designed to release orlistat and/or acarbose in a prolonged manner with the intention of obtaining release of orlistat and acarbose from duodenum and distal jejunum, where the ileal brake feed-back mechanism is located, see FIG. 6.

Figure 7A:
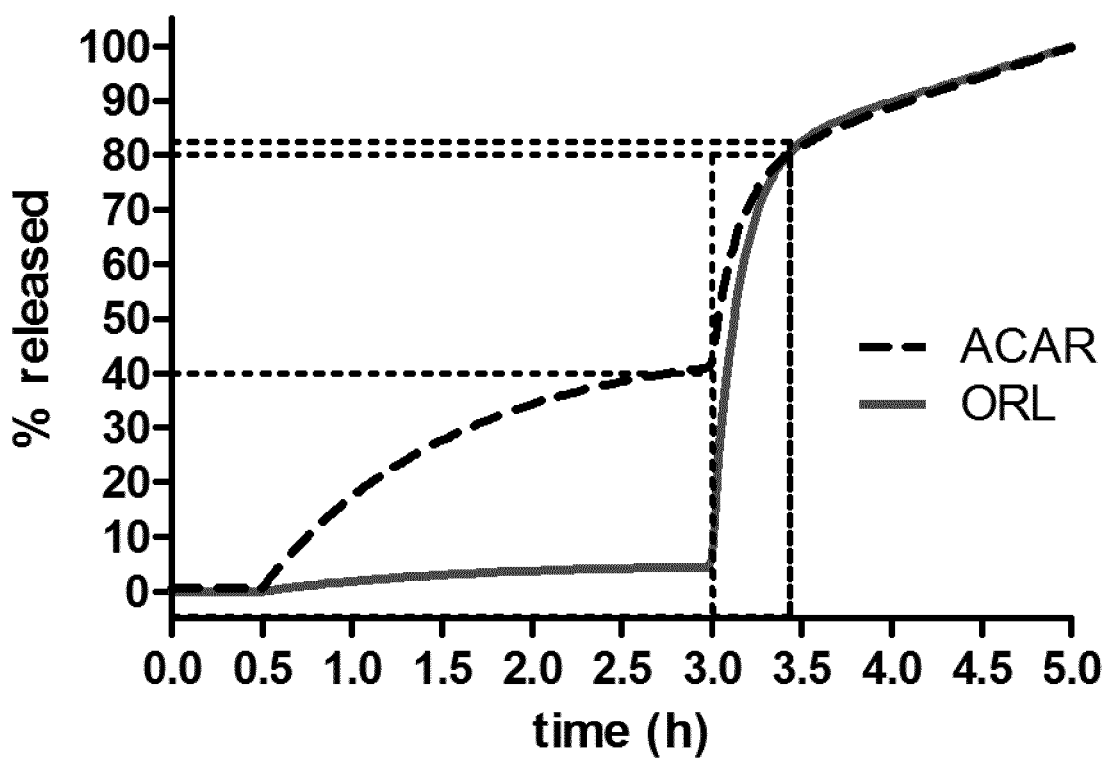

Target release profiles obtained by the three sub-doses of G1-G3 for each of the two APIs is illustrated in FIG. 7a herein. It is important to balance the amounts of orlistat and acarbose in the individual parts of the MR composition in order to obtain the desired clinical outcome.

A composition of the invention aims at fulfilling the following dissolution pattern when tested in accordance with the in vitro dissolution tests described in the United States Pharmacopoeia General Test Chapter on DISSOLUTION <711>[63] using Apparatus 2 (SAM SOTAX automatic sampler connected to HPLC apparatus or Fraction Collector AT7 SMART SOTAX). The following conditions are used; 900 ml vessel volume, paddle at 75 rpm, minigranules are prepared in capsules size TOO white/white, capsules are put into spiral stainless steel sinker 25-27×11 mm. Bi-phasic dissolution medium (900 ml and 37.0±0.5° C.,) is employed, for t=0 h to t=3 h, 25 mM $KH_2PO_4$ and pH=3.2 (corresponding to in vivo gastric fed state conditions) and for t=3 h to t=8 h, 25 mM $KH_2PO_4$ and pH=6.5 (adjusted by NaOH 5M) and addition of Sodium Dodecyl Sulphate to a total concentration of 0.5% w/w (corresponding to in vivo intestinal fed state conditions).

Samples are collected in time series. The amount of released API (orlistat and/or acarbose) is determined by HPLC (HPLC Agilent Technologies type 1100 or 1200 with DAD detector, monitored with OpenLab software, Agilent Technologies) as follows: 2 HPLC columns in series; Hibar, Purosphere, RP-8 (L=150 mm, internal diameter 4.6 mm, particle size 5 μm) and APS-2-Hypersyl (L=250 mm, internal diameter 4 mm, particle size 5 μm), flow rate 2 mL/min, injection volume 50 μL, sample temperature 25° C., column temperature 40° C., run time 15 minutes. Elution buffer solution: 0.6 g $KH_2PO_4$ and 0.35 g $Na_2HPO_4$, $2H_2O$ in 1 L of water, mobile phase buffer solution: 28% v/v; acetonitrile: 72% v/v. Detection by UV spectrometer at 210 nm. A standard preparation of acarbose and orlistat in water/acetonitrile 50/50 v/v with 3 external calibration points was used. The samples was not prepared and put into amber vials.

The complete composition of the invention aims to have the following amounts dissolved of acarbose and orlistat at different timepoints during in vitro dissolution:

| Sample taken at time t after start of the test of complete composition | Dissolved acarbose (% w/w) [target] | Dissolved orlistat (% w/w) [target] |
| --- | --- | --- |
| 15 min, pH 3.2 | 0-30 [0] | 0-10 [0] |
| 1 h, pH 3.2 | 0-50 [30] | 0-10 [5] |
| 3 h, pH 6.5 | 30-80 [50] | 0-20 [5] |
| 3.5 h, pH 6.5 | 40-95 [75] | 10-95 [30] |
| 4 h, pH 6.5 | 50-100 [85] | 20-100 [50] |
| 4.5 h, pH 6.5 | 60-100 [90] | 40-100 [70] |
| 6 h, pH 6.5 | 70-100 [95] | 70-100 [85] |
| 8 h, pH 6.5 | 70-100 [100] | 70-100 [90] |

Figure 11:
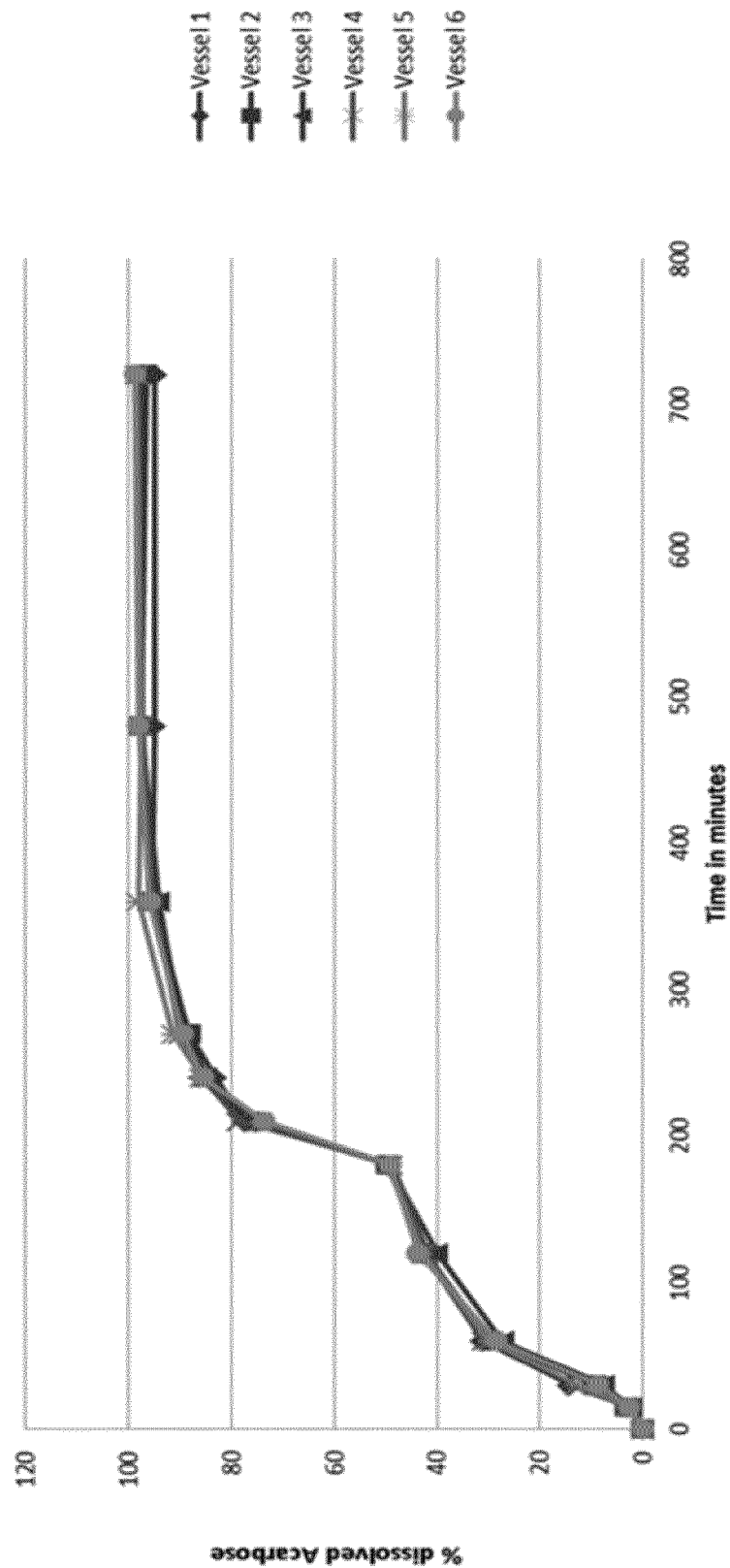
Figure 12:
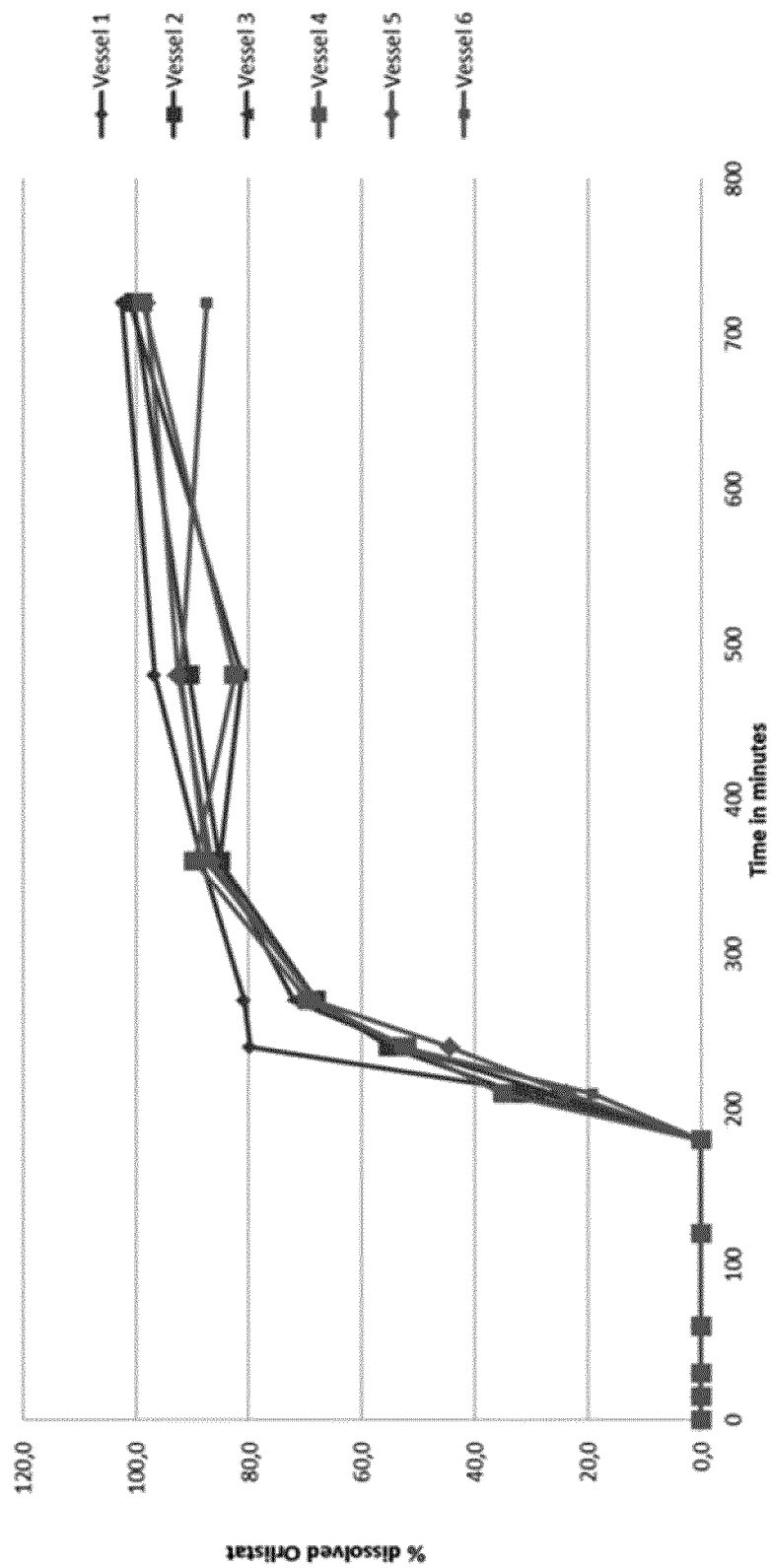

In vitro dissolution data for a multiple-unit capsule, i.e. Example 4H, is presented in FIG. 11 (acarbose) and FIG. 12 (orlistat).

The composition of the G1 granules alone aims to have the following amounts dissolved of acarbose at different timepoints during in vitro dissolution:

| Sample taken at time t after start of the test of G1 granules | Dissolved acarbose (% w/w) [target] |
| --- | --- |
| 15 min, pH 3.2 | 0-30 [0] |
| 1 h, pH 3.2 | 0-50 [35] |
| 3 h, pH 6.5 | 30-80 [70] |
| 3.5 h, pH 6.5 | 40-95 [75] |
| 4 h, pH 6.5 | 50-100 [80] |
| 4.5 h, pH 6.5 | 60-100 [80] |
| 6 h, pH 6.5 | 70-100 [85] |
| 8 h, pH 6.5 | 70-100 [90] |

Figure 13:
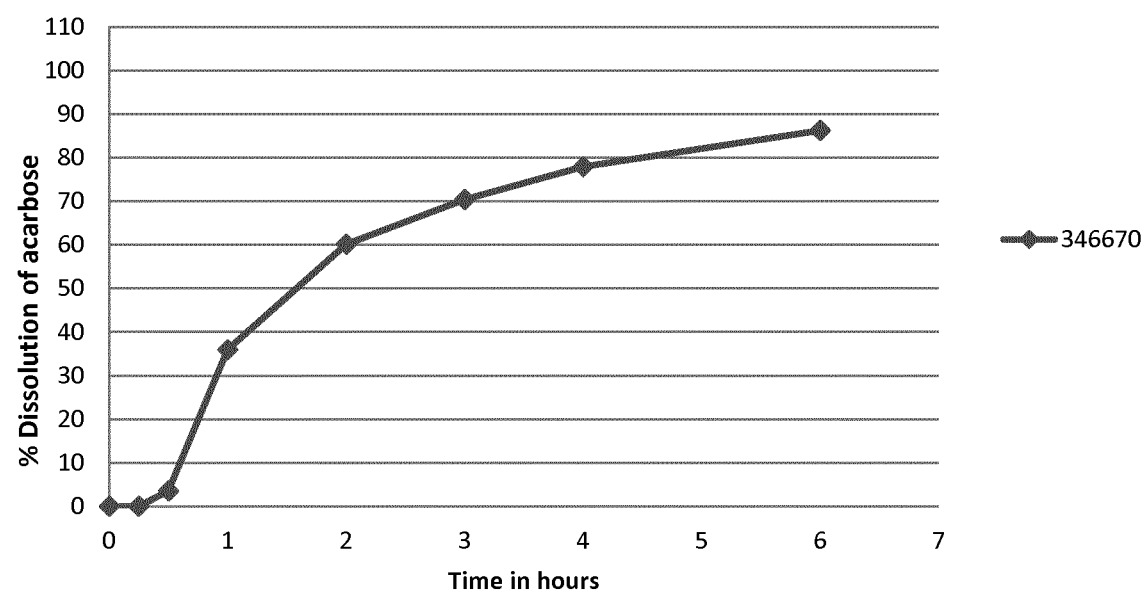

In vitro dissolution data for a G1 granule included in Example 4H, is presented in FIG. 13 (acarbose). The dissolved amount in % relates to % release of the G1 granule.

The composition of the G2 granules alone aims to have the following amounts dissolved of acarbose and orlistat at different timepoints during in vitro dissolution:

| Sample taken at time t after start of the test of G2 granules | Dissolved acarbose (% w/w) [target] | Dissolved orlistat (% w/w) [target] |
| --- | --- | --- |
| 15 min, pH 3.2 | 0-10 [0] | 0-10 [0] |
| 1 h, pH 3.2 | 0-30 [10] | 0-10 [0] |
| 3 h, pH 6.5 | 0-30 [15] | 0-20 [0] |
| 3.5 h, pH 6.5 | 50-95 [80] | 10-95 [25] |
| 4 h, pH 6.5 | 60-100 [90] | 30-100 [50] |
| 4.5 h, pH 6.5 | 70-100 [100] | 50-100 [75] |
| 6 h, pH 6.5 | 70-100 [100] | 70-100 [85] |
| 8 h, pH 6.5 | 70-100 [100] | 70-100 [90] |

Figure 14:
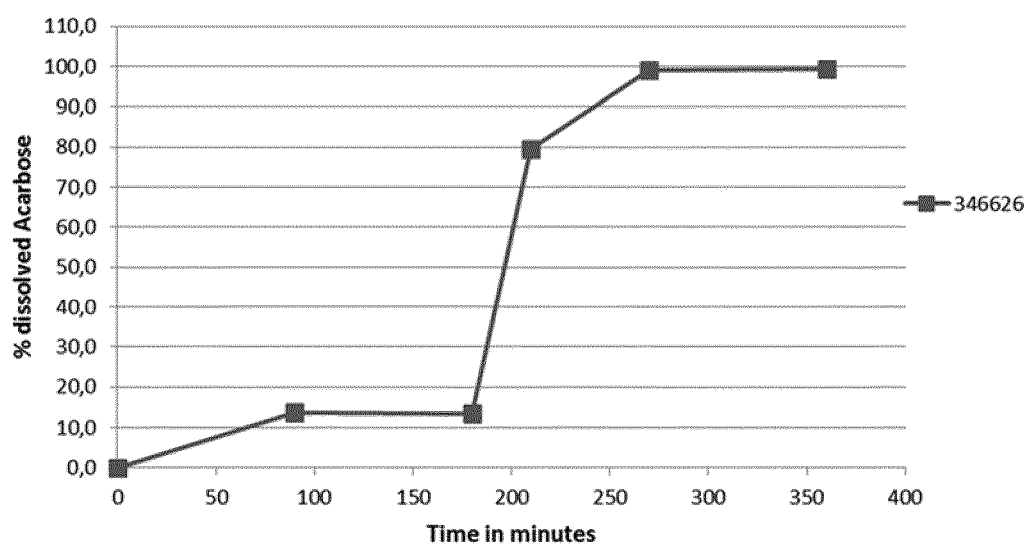
Figure 15:
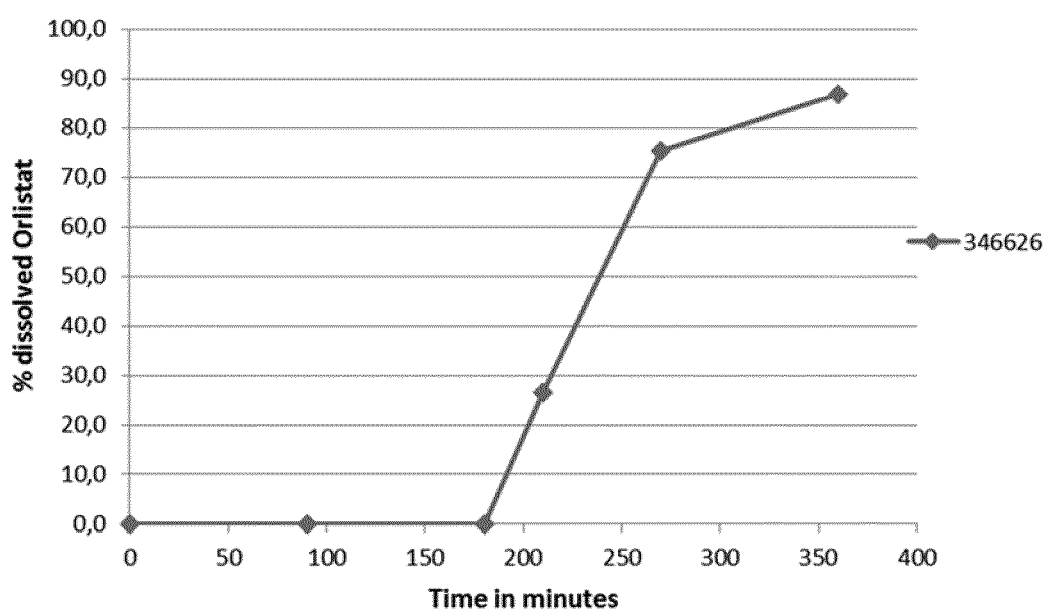

In vitro dissolution data for a multiple-unit capsule, i.e. Example 4H, is presented in FIG. 14 (acarbose) and FIG. 15 (orlistat). The dissolved amount in % relates to % release of the G2 granule.

The composition of the G3 granules alone aims to have the following amounts dissolved of acarbose and orlistat at different timepoints during in vitro dissolution:

| Sample taken at time t after start of the test of G3 granules | Dissolved orlistat (% w/w) [target] |
| --- | --- |
| 15 min, pH 3.2 | 0-10 [0] |
| 1 h, pH 3.2 | 0-20 [5] |
| 3 h, pH 6.5 | 0-30 [10] |
| 3.5 h, pH 6.5 | 10-95 [25] |
| 4 h, pH 6.5 | 20-100 [35] |
| 4.5 h, pH 6.5 | 30-100 [45] |
| 6 h, pH 6.5 | 70-100 [90] |
| 8 h, pH 6.5 | 70-100 [100] |

Figure 16:
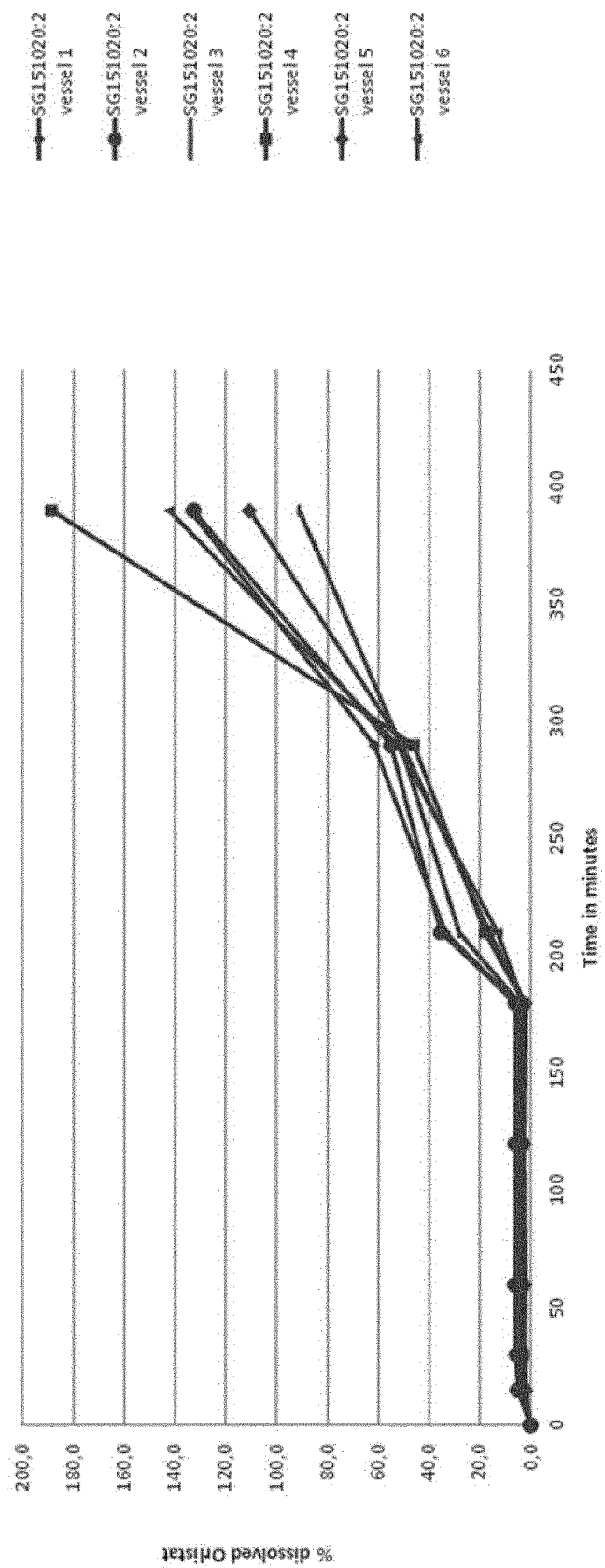

In vitro dissolution data for a multiple-unit capsule, i.e. Example 4H, is presented in FIG. 16 (orlistat). The dissolved amount in % relates to % release of the G3 granule.

This invention may be presented as (at least) three individual compositions intended to be administered orally at the same time or it may be in form of one oral MR dosage form (Granules 1-3, see above). Thus, it may be e.g. in the form of three solid dosage forms, where the first dosage form (corresponding to G1) is a prolonged release ($DR_{DC}$-$PR_{GASTRIC}$) dosage form intended to start its release of acarbose in the stomach releasing acarbose gradually during the transit through the GI tract until distal jejunum is reached. This first delayed prolonged release $DR_{DC}$-$PR_{GASTRIC}$ composition may be formulated as tablets, capsules, granules, pellets, mini-tablets or pellets made by extrusion/spheronization etc. with a delaying coating, where the coating is applied to delay the release by approximately 0-40 minutes of the API. The second composition (corresponding to G2) is intended to be enteric coated (EC) and then have a rapid release (RR) of the APIs when it enters the duodenum and proximal small intestine. This second $DR_{EC}$-$RR_{PROX\ SI}$ composition may be one (APIs combined) or two (APIs separated) different tablets, capsules, granules, pellets, mini-tablets or pellets made by extrusion/spheronization etc. with an EC-coating. The third composition (corresponding to G3) may also be a solid dosage form, intended to start its release of primarily orlistat with approximately 0-40 minutes delay i.e. ideally just before the composition reaches duodenum and the proximal part of the small intestine and then releasing orlistat gradually during the transit through the GI tract until distal jejunum is reached. This third delayed prolonged release $DR_{DC}$-$PR_{GASTRIC}$ and/or $DR_{EC}$-$PR_{INTESTINAL}$ composition could be formulated as tablets, capsules, granules, pellets, mini-tablets or pellets made by extrusion/spheronization etc. with a delaying coating that delays the release by approximately 0-40 minutes and/or an enteric coating that delays the start of the release even more. Thus, the aim is that the composition releases orlistat and acarbose until it reaches distal jejunum and to have no release of any of the two drugs in ileum, where the ileal brake feed-back mechanism is located. The idea is to in the first phase have a prolonged and sustained baseline release to distal jejunum of both acarbose and orlistat with at least approximately up to 20 minutes delay. In the second phase, at duodenum and proximal small intestine, a rapid release of both acarbose and orlistat will take place; and in the third phase at mid-jejunum the last part of the prolonged release will complete the total release. This can be obtained using a variety of techniques such as formulating the dosage form as MR-tablets, MR-capsules, MR-granules, MR-pellets, MR-mini-tablets etc. optionally with a coating that provides prolonged release and/or enteric coating or by formulating the MR-dosage form with excipients that enables a prolonged release e.g. by providing matrix formulations. In the paragraphs below various formulation principles are mentioned, all within the scope of the present invention. Moreover, in the experimental part numerous examples of suitable compositions are given.

If the composition of the invention is made up of three or four individual compositions as described above, then the present invention also relates to a kit comprising the first, the second, the third and the fourth composition, if present, optionally with instructions to use thereof. The kit may be in the form of a package or in the form of a blister package.

However, it would be an advantage to provide the three or four parts in a single modified-release (MR) composition. Alternatively, as two single modified-release compositions, one containing acarbose (corresponding to part G1 and G2A) and the other containing orlistat (corresponding to part G2B and G3).

Such a composition is a MR composition, where the doses of the total amount of the APIs are sub-divided into the individual parts that are individually designed in order to control the release pattern of each sub-dose.

At least five main design principles can be used in order to reach the release pattern of the two APIs in this fixed oral dose combination product. These principles are explained in the following. However, other formulation principles that lead to similar results are intended to be within the scope of this invention.

The compositions of the invention are in the form of oral dosage forms including tablets, capsules, granules, pellets, mini-tablets etc. For illustrative purposes only, multiple-unit tablets, bi-layer tablets, coated tablets, capsules and oral powders are described below, but it could as well be any of the other types of solid dosage forms or combination of dosage forms.

Due to the favourable release profiles of the APIs from the different units, the invention may also be presented as a formulation only containing either acarbose or orlistat. A way to manufacture such compositions is to exclude one granule (G1 or G3) and to exchange the active substance part to a filler in G2 and then combine the two granules into a multiple-unit dosage form mentioned below (see also Example 4Q, Example 4R and Example 4S). This is applicable to all the dosage forms below but only presented for the multiple-unit capsule.

A composition of the invention may suitably be in the form of a multiple-unit tablet or capsule or a layered tablet such as a bi-layer tablet or a coated tablet in the form of a combined multiple-unit and single-unit (monolithic) tablet.

Figure 8:
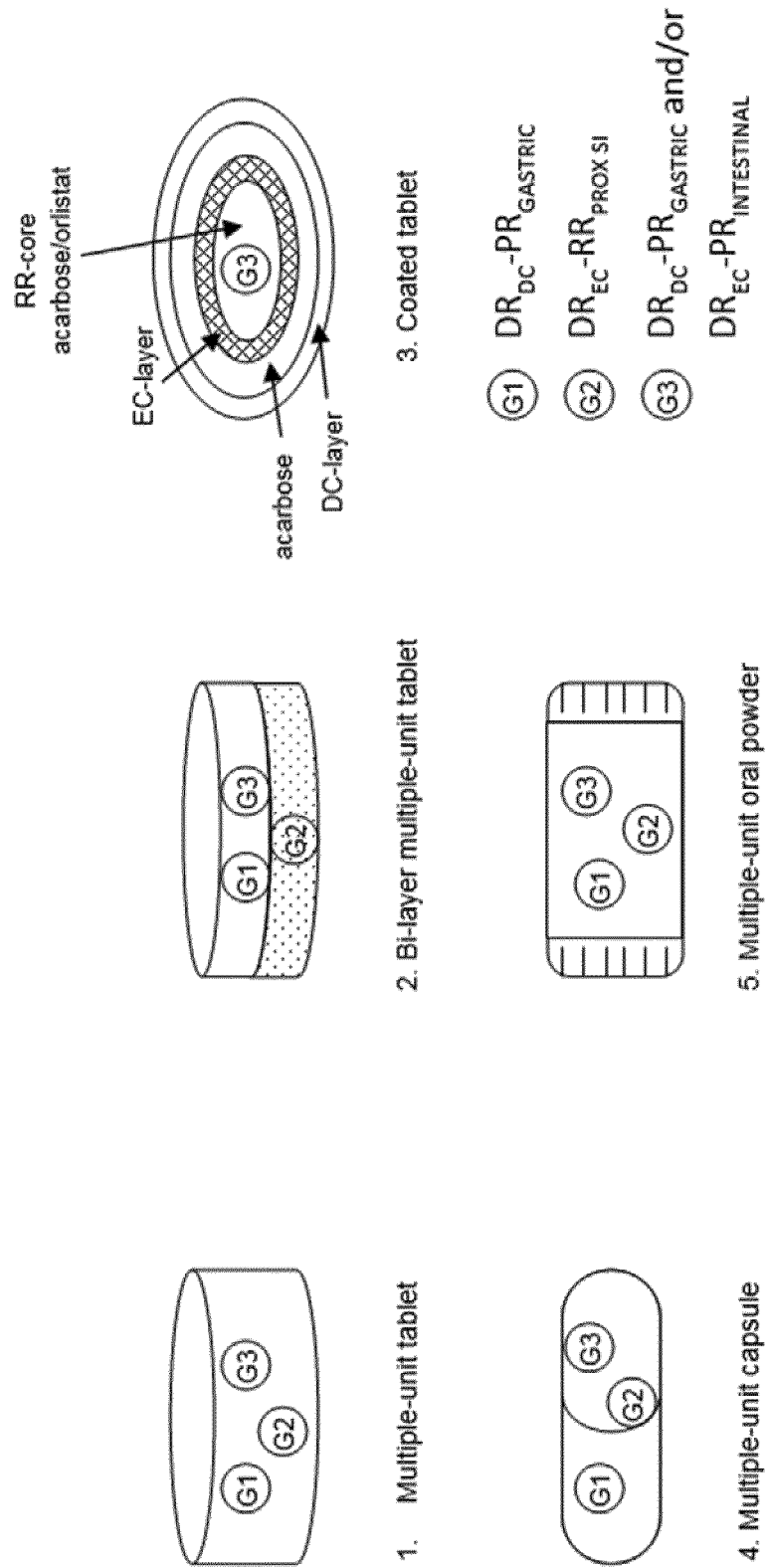

The five exemplified design principles are the following:
1. Multiple-unit tablet
2. Bi-layer multiple-unit tablet
3. Coated tablet
4. Multiple-unit capsule
5. Multiple-unit oral powder The dosage forms are schematically illustrated in FIG. 8 herein.

1. Multiple-Unit Tablet

Figure 9:
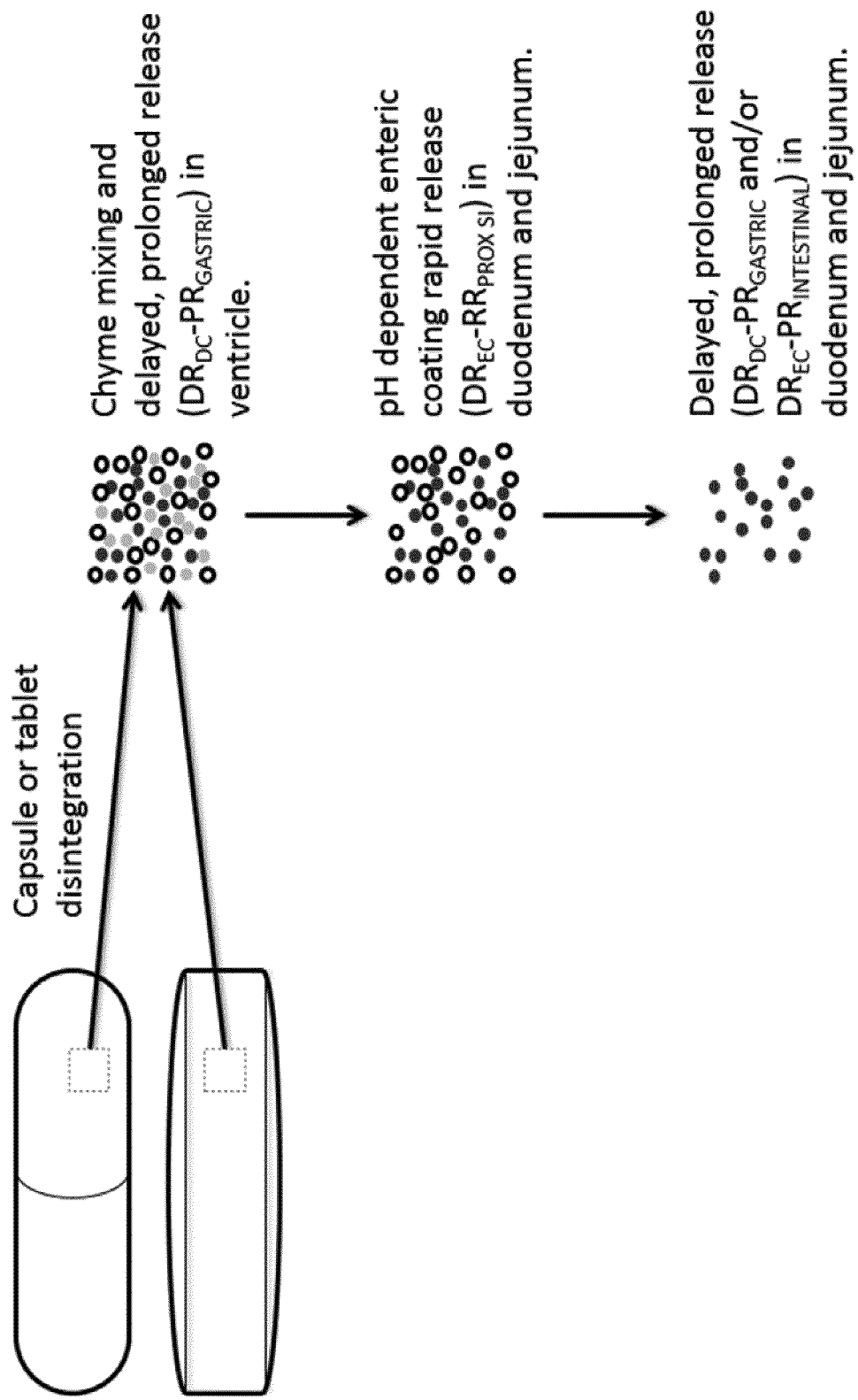

A multiple-unit tablet is formulated by preparing (at least) three different types of granules (Granule 1-3 or G1-3, see above), pellets or mini-tablets or pellets made by extrusion/spheronization with different design principles that subsequently are blended to a homogenous mixture together with additional pharmaceutical excipients and thereafter formed into a tablet by a standard powder compression operation. The design principle of the multiple-unit tablet is illustrated in FIGS. 8 and 9 herein where the three types of sub-units corresponds to delayed prolonged release granules ($DR_{DC}$-$PR_{GASTRIC}$) of acarbose (G1) and orlistat (G3) and enteric coated rapid release granules ($DR_{EC}$-$RR_{PROX\ SI}$) containing both acarbose and orlistat (G2).

The preferred design principle is a multiple-unit MR dosage form, i.e. the APIs are formulated as multiple units, each one consisting of API and suitable pharmaceutical excipients. The rationales behind this conclusion are:
1. It is considered ideally that before emptied into the proximal small intestine primarily acarbose will effectively disperse in the stomach, mix with and be homogenously distributed within the gastric food contents. It is assumed that the mixing with the food chyme will be maintained throughout the small intestine. This is achieved by dispersing acarbose in $DR_{DC}$-$PR_{GASTRIC}$ granules (G1) of about 0.5 mm or smaller (e.g. 100-500 µm) in size or minitablets of about 1.5 mm in size that can start to disperse after approximately up to 40 minutes delay in the food contents of the stomach and continue to disperse in the proximal small intestine after administration and tablet disintegration.
2. A multiple-unit form is needed from biopharmaceutical and regulatory perspectives for the administration of the enteric coated rapid release granules ($DR_{EC}$-$RR_{PROX\ SI}$ or G2); it is to be mentioned that the enteric coat protects the API from being released until there is a shift in pH from to less acid, neutral, alkaline pH. In other words, the release will not take place in the stomach, but one delivered to the small intestine, the release is rapid.
3. A drug release pattern that is approximately the same for a whole tablet as for half a tablet is possibly easier to obtain for a multiple-unit tablet than for a single-unit tablet (the breakage will not result in the formation of a new surfaces that can affect the drug release).

2. Bi-Layer Multiple-Unit Tablet

A bi-layer multiple-unit tablet should be considered as an alternative to the formulation approach mentioned above. The $DR_{EC}$-$RR_{PROX\ SI}$ (G2) containing part of the tablet must however still be designed as a multiple-unit tablet in order to get an enteric protection and as rapid release of orlistat in the proximal intestine as possible. Thus, a bi-layer tablet consisting of a combined multiple-unit and single-unit (monolithic) tablet is the consequence. The PR layer may be compressed with a higher compression force to increase the dissolution time, while the $DR_{EC}$-$RR_{PROX\ SI}$ granule (G2) containing layer may be compressed with less force preventing the granules from breakage and enabling a fast disintegration and distribution before entering the proximal small intestine. Alternatively, the bi-layer tablet may be formulated using a double compression Bi-Layer Tablet Press, for example Korsch model XM 12, equipped with a second layer feeder.

The design principle of the bi-layer tablet is illustrated in FIG. 8 herein.

3. Coated Tablet

A coated tablet is formulated by preparing a tablet core containing orlistat and acarbose intended for drug release in the proximal small intestine. The core may also contain prolonged release granules, pellets or mini-tablets of API, primarily orlistat ($DR_{DC}$-$PR_{GASTRIC}$ or "G3" in FIG. 8). The tablet core is then coated with an enteric coating. On top of the enteric coating is an additional layer with API—primarily acarbose—for stomach release. This layer may finally be protected by a delaying coating of approximately 0-40 minutes.

A coated tablet may also be formulated as described in the examples herein, i.e. a tablet core containing acarbose and orlistat for prolonged release, the tablet core being provided with an enteric coating containing acarbose and orlistat (which are rapidly released once the enteric coating dissolves) and on top of the enteric coat is a further coat providing a prolonged release of acarbose. Between the core and the enteric coat and/or between the enteric coat and the topcoat a further coating layer may be provided to protect one or more substance from negative impact from the enteric coating layer.

4. Multiple-Unit Capsule

A multiple-unit capsule is formulated by preparing (at least) three granules, pellets or mini-tablets with different design principles that subsequently are blended to a homogenous mixture together with additional pharmaceutical excipients and thereafter filled into a capsule by a standard capsule filling operation. The design principle of the multiple-unit capsule is the same as for the multiple-unit tablet mentioned above where the three types of sub-units corresponds to two types of delayed prolonged release granules of acarbose ($DR_{DC}$-$PR_{GASTRIC}$) and of orlistat ($DR_{DC}$-$PR_{GASTRIC}$ and/or $DR_{EC}$-$PR_{INTESTINAL}$) and enteric coated rapid release granules of both acarbose and orlistat ($DR_{EC}$-$RR_{PROX\ SI}$) as illustrated in FIGS. 8 and 9. In vitro dissolution results are displayed for the three-granule (G1+G2+G3) combination from a hard gelatin capsule—acarbose release in FIG. 11 and orlistat in FIG. 12. The single granules have also been tested separately, i.e. G1 acarbose release in FIG. 13, G2 acarbose release in FIG. 14, G2 orlistat release in FIG. 15 and G3 orlistat release in FIG. 16. Tested alternatives to G1 with coated ethylcellulose/hydroxypropylmethylcellulose (HPMC) are presented as G1 extruded pellet with ethylcellulose/HPMC in FIG. 17 and as G1 extruded pellet with hard fat/GMS in FIG. 18.

Figure 19:
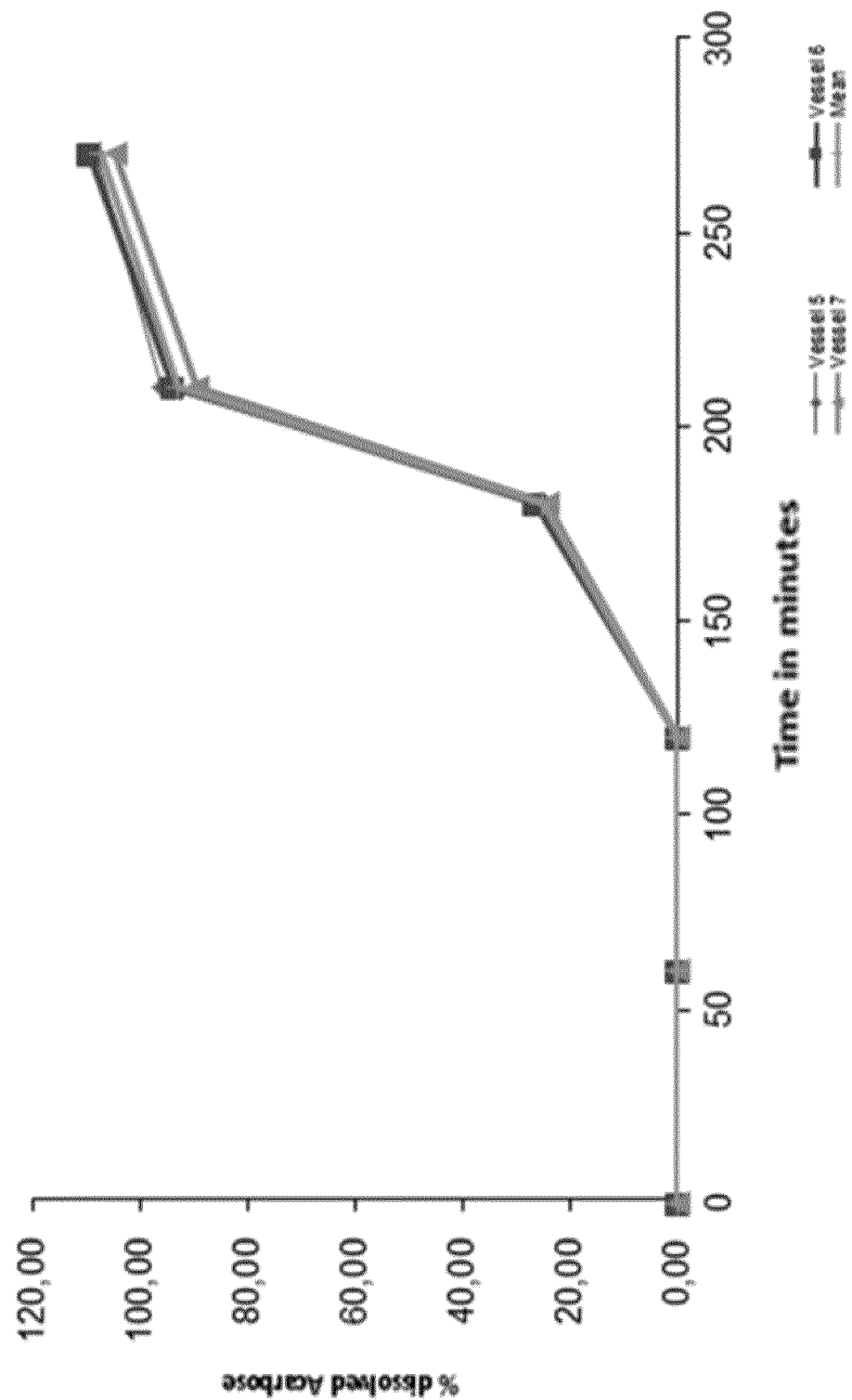
Figure 20:
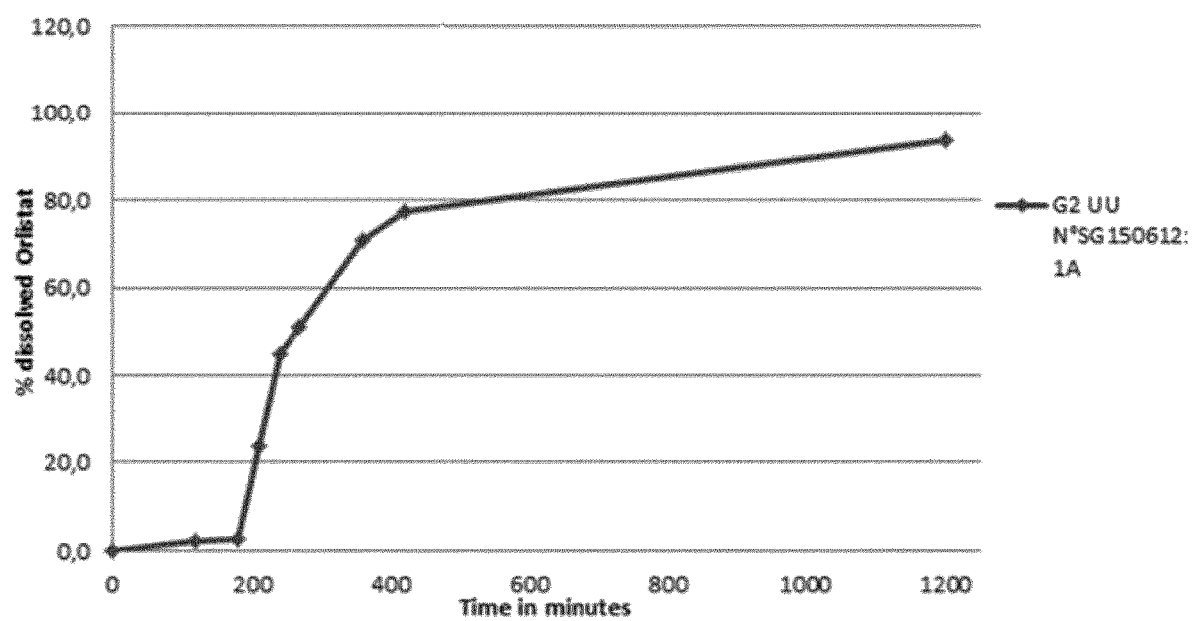

Tested alternative to G2 with coated ethylcellulose/HPMC is presented as G2 extruded pellet core with acarbose release in FIG. 19 and orlistat release in FIG. 20.

5. Multiple-Unit Oral Powder

A composition of the invention may suitably be in the form of a single unit sachet filled with powder for oral administration in the form of a combined multiple-unit powder. A multiple-unit powder is formulated by preparing (at least) three granules, pellets or mini-tablets with different design principles that subsequently are blended to a homogenous mixture together with additional pharmaceutical excipients and thereafter filled into a single unit sachet by a standard sachet filling operation. The design principle of the multiple-unit capsule is the same as for the multiple-unit tablet and capsule mentioned above where the three types of sub-units corresponds to two types of delayed prolonged release granules of acarbose ($DR_{DC}$-$PR_{GASTRIC}$) and of orlistat ($DR_{DC}$-$PR_{GASTRIC}$ and/or $DR_{EC}$-$PR_{INTESTINAL}$) and enteric coated rapid release granules of both acarbose and orlistat ($DR_{EC}$-$RR_{PROX\ SI}$) as illustrated in FIG. 8 herein.

Two other compositions aiming for a modified release including the combination of acarbose and orlistat has previously been described in patent EP 0638317 A1 with a HPMC-coated tablet and in patent application CN 102872062 A with a two-layer tablet. The compositions are presented in Example 7A (EP 0638317) and Example 7B (CN 102872062) below. The manufactured compositions have been tested for in vitro dissolution and the results are presented in FIG. 21 (EP 063831) and FIG. 22 (CN 102872062).

General Formulation Issues

In addition to the delivery aspects discussed above, the preparation should show the following general product properties:

Acceptable variation in dose and dose distribution between the different parts of the composition Compositions with good mechanical strength and low friability No incompatibilities between API and pharmaceutical excipients Stable preparation Acceptable taste (ideally without taste)

Good pharmaceutical finish, including uniform colour

Easily breakable in two halves, when the composition is in the form of a tablet

Drug release properties the same for a whole tablet and a half tablet, when the composition is in the form of a tablet APIs that are stable in the GI-tract Granules should not be bio(muco)-adhesive after disintegration in vivo Enteric Coated Rapid Release ($DR_{EC}$-$RR_{PROX\ SI}$d Granules (G2)—Formulation Issues The enteric coated granules should be unaffected by the conditions in the stomach but quickly dissolve in the upper part of the intestine, i.e. a complete dissolution of the APIs within about 30-60 min. The preparation should show the following performance:

Quick wetting of and liquid penetration into the tablet or capsule followed by short disintegration time of the tablet or capsule (target time about 1-5 min during in vitro testing).

The disintegrated granules/pellets/mini-tablets should disperse in the stomach and thereafter gradually be transferred into the intestine in physically intact form (a process occurring for about 30 min).

After entry into the upper part of the intestine, the enteric coating dissolves quickly (about 5-30 min).

Quick wetting of and liquid penetration of the remainder of the enteric coated granules/pellets/mini-tablets followed by quick wetting of APIs.

A rapid dissolution of APIs (about 5-30 min).

In order to prepare a composition of the invention one or more pharmaceutically acceptable excipients may be used. Selection of a pharmaceutically acceptable excipient may depend on whether it is used in the $DR_{DC}$-$PR_{GASTRIC}$ (G1), $DR_{DC}$-$PR_{GASTRIC}$ and/or $DR_{EC}$-$PR_{INTESTINAL}$ (G3), $DR_{EC}$-$RR_{PROX\ SI}$ (G2) or extragranular part of the composition; thus, a pharmaceutically acceptable excipient that functions to delay the release of an active ingredient other than the enteric coating is normally not suitable for use in the $DR_{EC}$-$RR_{PROX\ SI}$ (G2) part of the composition. Likewise, a pharmaceutically acceptable excipient that is likely to rapidly release active ingredients will normally not be suitable for use in the $DR_{DC}$-$PR_{GASTRIC}$ (G1) or $DR_{DC}$-$PR_{GASTRIC}$ and/or $DR_{EC}$-$PR_{INTESTINAL}$ (G3) parts of the composition. In the following is given an overview of pharmaceutically acceptable excipients for use in accordance with the present invention. A person skilled in the art will know which excipients are suitable for use in the different parts of the composition.

In the present context, the term "pharmaceutically acceptable excipient" is intended to denote any material, which is inert in the sense that it substantially does not have any therapeutic and/or prophylactic effect per se. A pharmaceutically acceptable excipient may be added to the active drug substance(s) with the purpose of making it possible to obtain a pharmaceutical formulation, which has acceptable technical properties. A pharmaceutically acceptable excipient in relation to solid dosage forms normally includes fillers, diluents, binders, wetting agents, pH adjusting agents, solubilizers, stabilizers, surfactants, modified release agents, colorants, flavouring agents etc.

If one or more of the parts of the composition is in the form of multiple units, such units may be coated. The final composition may also be provided with a coating.

With regard to the function of a pharmaceutically acceptable excipient, there is normally some overlap. Thus, e.g. microcrystalline cellulose may function as a binder as well as a filler and starch may function as a binder as well as a disintegrant. Accordingly, the specific examples given in the following may belong to other groups than that specifically mentioned.

As mentioned above, fillers/diluents/binders may be in pharmaceutical formulations according to the present invention. Examples dextrins, maltodextrins (e.g. Lodex® 5 and Lodex® 10), dextrose, fructose, glucose, inositol, erythritol, isomalt, lactitol, maltitol, maltose, mannitol, sorbitol, sucrose, tagatose, trehalose, xylitol, lactose (e.g., spray-dried lactose, 〈-lactose,®-lactose, Tablettose®, various grades of Pharmatose®, Micro-tose or Fast-Floc®), low-substituted hydroxypropylcellulose (e.g LH 11, LH 20, LH 21, LH 22, LH 30, LH 31, LH 32 available from Shin-Etsu Chemical Co.), L-hydroxypropylcellulose (low-substituted) (e.g. L-HPC-CH31 and L-HPC-LH11), microcrystalline cellulose (e.g., various grades of Avicel®, such as Avicel® PH101, Avicel® PH102 or Avicel® PH105, Elcema® P100, Emcocel®, Vivacel®, Ming Tai® and Solka-Floc®), dextrins, maltodextrins (e.g. Lodex® 5 and Lodex® 10), starches or modified starches (e.g potato starch, maize starch, rice starch, pre-gelatinised starch), polyvinylpyrrolidone, polyvinylpyrrolidone/vinyl acetate copolymer, agar (e.g. sodium alginate), calcium hydrogen phosphate, calcium phosphate (e.g. basic calcium phosphate, calcium hydrogen phosphate), calcium sulphate, calcium carbonate, carboxyalkylcellulose, dextrates, dibasic calcium phosphate, gelatine, gummi arabicum, hydroxypropyl cellulose, hydroxypropylmethylcellulose, magnesium carbonate, magnesium chloride, methylcellulose, polyethylene glycol, polyethylene oxide, polysaccharides e.g. dextran, soy polysaccharide, sodium carbonate, sodium chloride, sodium phosphate.

Glidants and lubricants may be incorporated such as stearic acid, metallic stearates, talc, waxes and glycerides with high melting temperatures, hydrogenated vegetable oils, colloidal silica, sodium stearyl fumarate, polyethylenglycols and alkyl sulphates. Suitable lubricants include talc, magnesium stearate, calcium stearate, stearic acid, hydrogenated vegetable oils and the like.

Fatty acids, fatty alcohols and fatty esters, for example: ethyl oleate, sodium oleate, lauric acid, methyl laurate, oleic acid, sodium caprate Dioctyl calcium sulfosuccinate, dioctyl potassium sulfosuccinate, dodecyltrimethylammonium bromide, hexadecyltrimethylammonium bromide, trimethyltetradecylammonium bromide, polyoxyehtylene ethers (polyoxyehtylene-9-lauryl ether), sodium dodecyl sulphate, sodium dioctyl sulfosuccinate, sodium laurate, sodium 5-thoxysalicylate, sodium salicylate;

Bile salts, for example:
sodium deoxycholate, deoxycholic acid, sodium cholate, cholic acid, sodium glycocholate, sodium glycodeoxycholate,
sodium taurocholate, sodium taurodeoxycholate.

Solubilizers such as cyclodextrins, for example:
beta-yclodextrin, dimethyl-beta-cyclodextrin, gamma-cyclodextrin, hydroxypropyl beta-cyclodextrin, methyl cyclodextrin; and dimethyl-beta-cyclodextrin.

The solubilizer can include an alcohol. Non-limiting examples of alcohols that can be used as solubilizers include tocopherol, ethyl alcohol, isopropanol, butanol, benzyl alcohol, ethylene glycol, propylene glycol, butanediol, glycerol, pentaerythritol, transcutol, dimethyl isosorbide, polyethylene glycol and mixtures thereof. In one embodiment, the solubilizer can be ethyl alcohol, benzyl alcohol, tocopherol, and mixtures thereof.

Modifying release agents may be used such as fatty acids and esters, fatty alcohols, cetyl alcohol, stearyl alcohol, mineral oils, hydrogenated vegetable oils, vegetable oils, acetylated hydrogenated soybean oil glycerides, Castor oil, phosphate esters, amides, phthalate esters, glyceryl cocoate oleyl alcohol, myristyl alcohol, sucrose octaacetate, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, poloxamers, polyvinyl alcohols, sorbitan monolaurate, sorbitan monooleate, sorbitan monopalmitate, sorbitan monostearate, sorbitan sesquioleate, sorbitan trioleate, sorbitan tristearate, ethylcellulose, cellulose acetate, cellulose propionate, cellulose nitrate, cellulose derivative selected from the group consisting of methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose, cellulose acetate, polylactic acid or polyglycolic acid and copolymers thereof, methacrylates, a co-polymer of methacrylate-galactomannan etc., polyvinyl alcohols, glycerinated gelatine and cocoa butter.

As mentioned above, the individual parts, the individual multiple units or the final composition may be coated. The coating material depends on the function of the coating. In the event where the coating is not applied with the purpose of delaying or prolonging the release the coating may be a film coating.

Suitable hydrophilic film formers for use in such a coating (i.e. a coating that does not delay or prolong the release) The film formers may be chosen from water-soluble or water-dispersible polymers such as starches or modified starches, gums, modified cellulose, polyvinylalcochol, polyacrylic acid, polyvinylpyrrolidone, polyethylenimine or mixtures thereof. The film formers may typically be hydroxypropylmethylcellulose (HPMC) (e.g. HPMC E5, HPMC E15), hydroxyethylcellulose, hydroxypropylcellulose, methylcellulose, polydextrose and maltodextrin, Sepifilm™ and Sepifilm™ LP available from Seppic S. A., Pharmacoat® available from Shin-Etsu Chemical Co. Other suitable polymers may be vinyls; such as polyvinylpyrrolidone and polyvinylacohol, or glycols; such as polyethylene glycol, or acrylics; such as methacrylic acid copolymers.

In order to optimize the properties of the film one or more film additive may be used such as e.g. a plasticizer. Suitable film additives include acetylated monoglyceride, acetyltributyl, acetyltributyl citrate, acetyltriethyl citrate, benzyl benzoate, calcium stearate, castor oil, cetanol, chlorebutanol, colloidal silica dioxide, dibutyl phthalate, dibutyl sebacate, diethyl oxalate, diethyl malate, diethyl maleate, diethyl malonate, diethyl fumarate, diethyl phthalate, diethyl sebacate, diethyl succinate, dimethylphthalate, dioctyl phthalate, glycerin, glyceroltributyrate, glyceroltriacetate, glyceryl behanate, glyceryl monostearate, hydrogenated vegetable oil, lecithin, leucine, magnesium silicate, magnesium stearate, polyethylene glycol, propylene, glycol, polysorbate, silicone, stearic acid, talc, titanium dioxide, triacetin, tributyl citrate, triethyl citrate, zinc stearate, wax.

The film-forming agent may also be admixed with anti-adhesives such as, e.g. colloidal silica, inert fillers, and pigments in a manner known per se.

Tackiness of the water-dispersible film-forming substances may be overcome by simply incorporating an anti-adhesive in the coating. The anti-adhesive is preferably a finely divided, substantially insoluble, pharmaceutically acceptable non-wetting powder having anti-adhesive properties in the coating. Examples of anti-adhesives are metallic stearates such as magnesium stearate or calcium stearate, microcrystalline cellulose, or mineral substances such as calcite, substantially water-insoluble calcium phosphates or substantially water-insoluble calcium sulphates, colloidal silica, titanium dioxide, barium sulphates, hydrogenated aluminium silicates, hydrous aluminium potassium silicates and talc. A preferred anti-adhesive is talc.

The above-mentioned film additives may also be used in coatings intended for delayed or prolonged release.

An enteric coating is typically gastro-resistant meaning that it is composed of material that is insoluble at a pH corresponding to pH in the stomach (i.e. pH below 4), whereas it dissolve when pH is shifted to neutral/alkaline pH. This enteric coating material is typically a methacrylic acid copolymer, i.e. a copolymer of methacrylate-galactomannan. The dissolution process of the enteric coating depends on the pKa of the polymer applied.

Examples of film-forming agents which are suitable for use to obtain prolonged release are agents selected from the group consisting of cellulose derivatives such as, e.g., ethylcellulose, cellulose acetate, cellulose propionate, cellulose butyrate, cellulose valerate, cellulose acetate propionate; acrylic polymers such as polymethyl methacrylate; vinyl polymers such as, e.g., polyvinyl acetate, polyvinyl formal, polyvinyl butyryl, vinyl chloride-vinyl acetate copolymer, ethylene-vinyl acetate copolymer, vinyl chloride-propylene-vinyl acetate copolymer; siliconpolymers such as ladder polymer of sesquiphenyl siloxane, and colloidal silica; polycarbonate; polystyrene; polyester; coumaroneindene polymer; polybutadiene; and other high molecular synthetic polymers.

The acrylic polymer may comprise one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

The acrylic coating may be an acrylic resin lacquer used in the form of an aqueous dispersion, such as that which is commercially available from Rohm Pharma under the tradename Eudragit® or from Colorcon under the tradename Acryl-EZE®. The acrylic coating may comprise a mixture of two acrylic resin lacquers commercially available from Evonik under the tradenames Eudragit® RL 30 D and Eudragit® RS 30 D, respectively. Eudragit® RL 30 D and Eudragit® RS 30 D are copolymers of acrylic and methacrylic esters with a low content of quaternary ammonium groups, the molar ratio of ammonium groups to the remaining neutral (meth)acrylic esters being 1:20 in Eudragit® RL30 D and 1:40 in Eudragit® RS 30 D.

Eudragit® RL/RS mixtures are insoluble in water and in digestive fluids. However, coatings formed from the same are swellable and permeable in aqueous solutions and digestive fluids. The Eudragit® RL/RS dispersions may be mixed together in any desired ratio in order to ultimately obtain a modified release formulation having a desirable dissolution profile.

The amount of the enteric coating applied is adapted so as to obtain a predetermined dissolution characteristic of the fraction of the composition in the proximal small intestine, i.e. the "Second part" release of the described invention.

A rapid release (RR) oral dosage form typically contains a disintegrant or superdisintegrant. The disintegrant or "disintegrating agent" that may be employed may be defined as any material that is capable of accelerating to a measurable degree the disintegration/dispersion of a composition of the invention. The disintegrant may thus provide for an in vitro disintegration time of less than 1-5 min, as measured according to e.g. the standard United States Pharmacopoeia (USP) disintegration test method[64]. This may be achieved, for example, by the material being capable of swelling, wicking and/or deformation when placed in contact with water and/or mucous (e.g. intestinal fluid), thus causing granules/pellets/mini-tablets to disintegrate when so wetted. Suitable disintegrants[65] include cellulose derivatives such as hydroxypropyl cellulose (HPC), low substituted HPC, methyl cellulose, ethyl hydroxyethyl cellulose, carboxymethyl cellulose calcium, carboxymethyl cellulose sodium, microcrystalline cellulose, modified cellulose gum; starch derivatives such as moderately cross-linked starch, modified starch, hydroxylpropyl starch and pregelatinized starch; and other disintegrants such as calcium alginate, sodium alginate, alginic acid, chitosan, docusate sodium, guar gum, magnesium aluminium silicate, polacrilin potassium and polyvinylpyrrolidone. Combinations of two or more disintegrants may be used. Preferred disintegrants include so-called "superdisintegrants"[66], such as cross-linked polyvinylpyrrolidone, sodium starch glycolate and croscarmellose sodium. Combinations of two or more superdisintegrants may be used.

Disintegrants may also be combined with superdisintegrants in compositions of the invention. Disintegrants and/or superdisintegrants are preferably employed in an (e.g. total) amount of between 0.5 and 15% by weight based upon the total weight of a composition. A preferred range is from about 0.1 to about 5%, such as from about 0.2 to about 3% (e.g. about 0.5%, such as about 2%) by weight. If employed in particulate form, particles of disintegrants and/or superdisintegrants may be presented with a particle size (weight and/or volume based average or mean diameter, see above) of between about 0.1 and about 100 μm (e.g. about 1 and about 50 μm). Alternatively, disintegrants and/or superdisintegrants may also be present as a constituent in composite excipients. Composite excipients may be defined as co-processed excipient mixtures. Examples of composite excipients comprising superdisintegrants are Parteck® ODT, Ludipress® and Prosolv® EASYtab.

To facilitate the dispersion rate in the proximal small intestine orlistat may be presented in the compositions of the invention in the form of microparticles. Microparticles preferably possess a weight based mean diameter, number based mean diameter, surface based mean diameter and/or a volume based mean diameter of between about 0.5 μm and about 30 μm, e.g. about 15 μm, such as between about 1 μm and about 10 μm. As used herein, the term "weight based mean diameter" will be understood by the skilled person to include that the average particle size is characterized and defined from a particle size distribution by weight, i.e. a distribution where the existing fraction (relative amount) in each size class is defined as the weight fraction, as obtained by e.g. sieving (e.g. wet sieving). As used herein, the term "number based mean diameter" will be understood by the skilled person to include that the average particle size is characterized and defined from a particle size distribution by number, i.e. a distribution where the existing fraction (relative amount) in each size class is defined as the number fraction, as measured by e.g. microscopy. As used herein, the term "volume based mean diameter" will be understood by the skilled person to include that the average particle size is characterized and defined from a particle size distribution by volumevolume, i.e. a distribution where the existing fraction (relative amount) in each size class is defined as the volume fraction, as measured by e.g. laser diffraction. As used herein, the term "surface based mean diameter" will be understood by the skilled person to include that the average particle size is characterized and defined from a particle size distribution by surface, i.e. as measured by eg photosedimentation.

Microparticles of orlistat may be prepared by standard micronization techniques, such as grinding, jet milling, dry milling, wet milling, precipitation, etc. An air elutriation process may be utilized subsequently to prepare specific size fractions, if required.

Additionally or alternatively, orlistat nanoparticles can be made by processes that include, or that further include, any other methods of reducing particle size, such as high pressure homogenization, recrystallization, grinding, sieving and/or centrifuging, to produce nanoparticles having an average particle size diameter of less than 1 um.

Orlistat nanoparticles may consist of only orlistat, such as when the milling process is affected without the use of a milling aid or other excipients. Orlistat nanoparticles may consist of the orlistat and a milling aid, such as where the milling process includes the use of a milling aid. The weight/weight ratio of orlistat to milling aid in the orlistat nanoparticles may be from approximately 10:1 to 20:1. The orlistat nanoparticles may not include a carrier. In some cases, the orlistat nanoparticles do not include a binder. Thus, the orlistat nanoparticles may be prepared without any carrier or binder to obtain orlistat nanoparticles having an average particle size of less than 1 urn that do not include carrier or binder material.

The orlistat nanoparticles may have an average particle size diameter of 0.01 μm, 0.05 μm, 0.1 μm, 0.2 μm, 0.3 μm, 0.4 μm, 0.5 μm, 0.6 μm, 0.7 μm, 0.8 μm, 0.9 μm, less than 1 μm, or an average particle size diameter between any two of these values. The orlistat nanoparticles may have an average particle size diameter of greater than 0.1 μm and less than 1.0 μm. The orlistat nanoparticles have a median particle size diameter of 0.2 μm. Up to 10% of the orlistat nanoparticles may have a particle size diameter of 0.1 μm or less. In some cases, at least 90% of the orlistat nanoparticles have a particle size diameter of up to 0.8 μm. In some cases, at least 80% of the orlistat nanoparticles have a particle size diameter of between 0.1 μm and 0.8 μm. The orlistat nanoparticles may have a median particle size diameter of 0.2 μm, wherein up to about 10% of the orlistat nanoparticles have a particle size diameter of 0.1 μm or less and 90% of the orlistat nanoparticles have a particle size diameter of up to 0.8 μm, or wherein at least 80% of the orlistat nanoparticles have a particle size diameter of between 0.1 μm and 0.8 μm.

To prevent hydrophobic agglomerates or clusters of orlistat or to improve properties like e.g. dissolution, a surfactant may be presented in the composition of the invention. Surfactants that may be employed are typically non-ionic (e.g., polysorbate 20, polysorbate 21, polysorbate 40, polysorbate 60, polysorbate 61, polysorbate 65, polysorbate 80, polysorbate 81, polysorbate 85, polysorbate 120, sorbitan monoisostearate, sorbitan monolaurate, sorbitan monopalmitate, sorbitan monostearate, sorbitan monooleate, sorbitan sesquioleate, sorbitan trioleate, glyceryl monooleate and polyvinylalcohol), anionic (e.g., docusate sodium and sodium lauryl sulphate) or cationic (e.g., benzalkonium chloride, benzethonium chloride and cetrimide).

In order to understand the complex environment in which orlistat and acarbose released from this invention exert their actions, the following paragraphs address the physiological background of the invention.

Gastrointestinal (GI) Absorption of Orally Administered Drug Products—Definition of Drug Absorption Oral administration of pharmaceutical products (immediate, controlled, extended or modified release products) is the preferred route for the majority of pharmaceutical products. The most common approach to evaluate the in vivo performance of orally administered drugs and dosage forms is to make a pharmacokinetic (PK) analysis of the determined plasma concentrations of the unchanged drug and/or its metabolites. Sometimes this PK data analysis is combined with a use of imaging techniques (such as magnetic resonance imaging, MRI) that simultaneously monitor the transit of the drug/dosage form through the GI tract. The oral bioavailability (F) is one of the most useful PK parameter in this context and F is strongly related to the pharmacological effect and safety for systemically acting drug products given by the oral route. F is affected by a number of processes, discussed below. F is the result of three general processes: fraction dose absorbed across the apical cell membrane into the cellular space of the enterocyte, described as fa, intestinal first-pass metabolism (EG) and hepatic first-pass metabolism (EH) (equation 1)[67,68].

$$F = fa \cdot (1 - EG) \cdot (1 - EH) \quad \text{(equation 1)}$$

Figure 10:
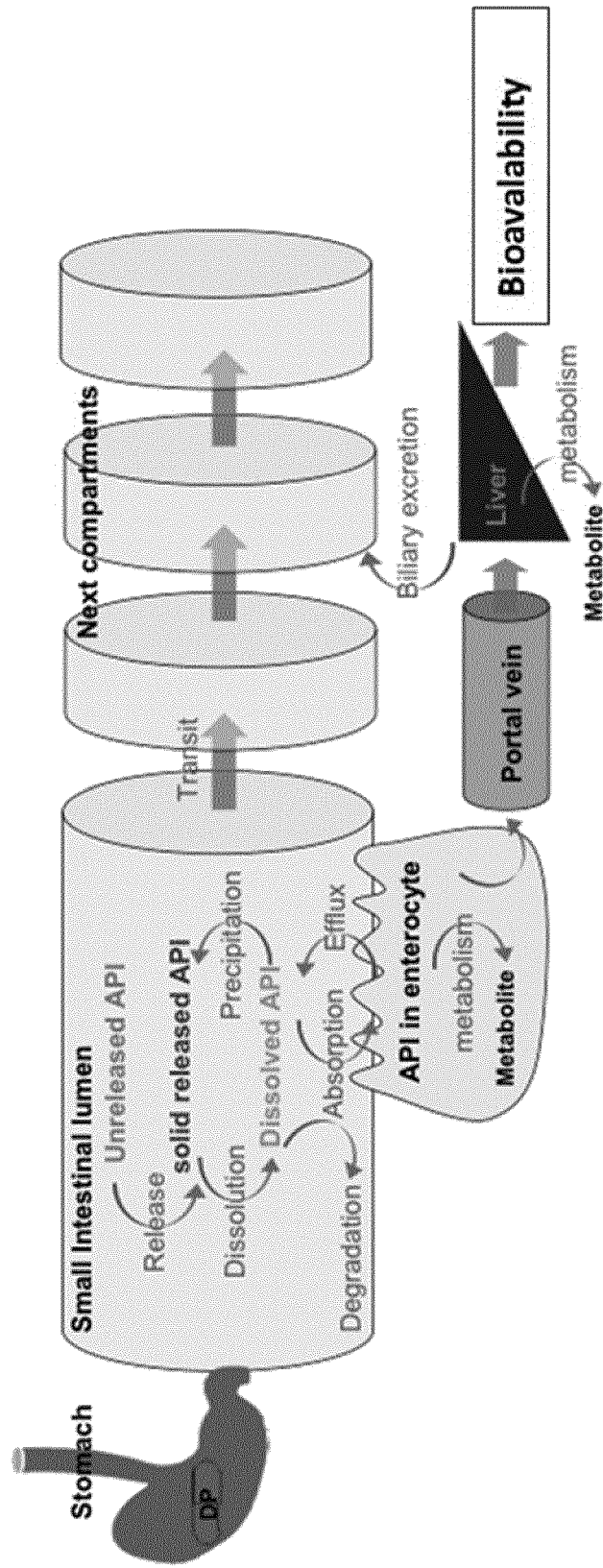

A schematic overview of most relevant processes involved is also provided in FIG. 10 herein.

The fraction of the dose absorbed across the apical epithelial membrane of the intestinal cells (both small and large intestine) (fa) (i.e. disappeared from GI lumen) is affected by various physiological and biochemical factors. These factors will to various extent influence drug solubility, drug release, dissolution, luminal degradation/complexation and effective intestinal wall permeability. In general, these factors can be grouped into three categories: (i) physicochemical factors of the drug molecule itself (i.e. active pharmaceutical ingredient; API), (ii) pharmaceutical factors such as design of formulations, including choice of pharmaceutical excipients and the physical/solid state form of the API in the final product, and (iii) physiological and pathophysiological factors in the GI system.

The composition of the present invention is an oral modified-release (MR) fixed dose combination formulation, where drug release, dissolution and intestinal effective permeability ($P_{eff}$) will occur in the stomach, in a larger part of the small intestine and to some extent in the large intestine. The biopharmaceutical simulations have provided a model that assists in the design and development of this MR formulation. This makes regional variation among GI factors even more critical. This fixed oral combination product will also have its active pharmacological sites located along the GI tract. The effect will therefore be directly affected to the concentration-time profiles of both drugs along the GI-tract. The incidence and extent of side-effects and safety issues for this local fixed combination will be related to both the local concentration-time profiles in the GI-tract for both APIs.

Gastrointestinal (GI) Physiology and its Role in Drug Absorption

In general drug absorption from the stomach is limited mainly due to low surface area of the gastric epithelium and unfavourable pH. Instead the small intestine is the major absorbing organ and the large intestine contributes to various extent dependent on the BCS class for the API[69]. The intestine is a long muscular tube with specialized regions where digestion and storage of diet occur. These intestinal regions are to different degrees supplied by arteries and drained by veins and a lymphatic trunk, which all are supported in a sheath of connective tissue below the thorax, termed the mesentery. Functionally, the GI system is divided into a preparative and primary storage region (mouth and stomach), a secretory and absorptive region (small intestine), a water reclamation system (ascending colon) and finally a waste-product storage system (the descending and sigmoid colon). Based on the luminal conditions and the nature of the tissue change along the GI tract, only the small intestine is structured to allow for maximal absorption of both nutrients from diet and pharmaceutical drugs. Important factors for establishing efficient local drug therapies include the free luminal concentration of API, the effective area, chemical stability, interaction with luminal particles (colloidal lipid related and other) and transit time in the different regions.

Ingestion and Stomach Physiology in Fasted and Fed States

The processing of eaten food inside the oral cavity is essential for defining and understanding the initial conditions of the chyme in the postprandial stomach that a local acting pharmaceutical product will be exposed to. The initial mixing between the components of the local fixed combination composition of the present invention and the ingested diet is crucial for the overall efficiency and side-effect panorama. The texture of food is significantly changed by mastication and salivation leading to particles of different size, shape, surface area and mechanical resistance as well as to varying physicochemical properties of the surrounding medium including pH value, surface tension or viscosity. All of these parameters affect the solubility and dissolution properties and accordingly the local concentrations of both APIs in this solid oral dosage form ingested together with a meal (which could be just prior meal intake, simultaneously and/or just after the finalizing of the meal intake). Mastication and salivation are the first steps of digestion and their interaction is essential to prepare the food for further gastric emptying and GI processing. After food enters the oral cavity, the individual particles are grinded and simultaneously mixed with saliva for lubrication and cohesive binding in order to form a swallowable bolus (a mixture of chewed food and saliva).

The stomach is in general divided into three functional parts. The fundus region acts together with the middle part of the stomach (corpus) as a storage compartment. In the distal part (antrum), food particles are milled, sieved and finally emptied through the gastric pylorus into proximal small intestine (duodenum). The stomach volume depends largely on its filling status. In the fasted state, the stomach is rather empty containing only a small volume of gastric juice (around 30-80 ml) and some gas. In the postprandial state, stomach filling volume may increase to 1000 ml or even more, depending on the volume of the ingested food and drinks as well as the individual physiology status[70-72]. This dynamic volume is an essential factor for the design of this local acting product.

The actual intra-gastric volume of the content is dynamic and depends on the fasting gastric volume, ingested volume of the meal, cumulative saliva and gastric secretion and is reduced by gastric emptying[73,74]. The total gastric volume has been shown to be larger than the consumed meal volume up to 3 h after intake of a light meal[75]. During digestion, gastric juice is produced with a total daily secretion volume of approximately 2000-3000 ml. In the fasted state, an unstimulated secretion rate of about 1 mL/min occurs that increases after meal intake to rates of 10 mL/min up to 50 mL/min[76]. The dynamic gastric filling volume is the saliva process with dynamic flow rate of up to 10 mL/min. The total daily secretion volume is 1000-1600 ml per day[77,78 74, 75]. Due to moderate peristaltic mixing, gastric contents are not homogenously distributed, which has a major importance for the design of the fixed oral MR combination composition of the present invention where a local effect throughout the GIT is essential. Typically, a lipid layer is located on top of the gastric fluid due to the lower density of fat compared to that of water. However, patient posture and ingestion order of the meal will influence the intra-gastric location of the lipid layer[79,80]. Solid particles accumulate in the more distal parts of the stomach due to their higher gravity, where they are ground by antral milling. Gastric emptying occurs as a decanting process of the watery phase with small suspended particles and emulsion droplets[81]. This uneven gastric distribution is considered in the design of this oral dosage form in order to optimize the efficiency and side-effect panorama.

The flow properties of gastric contents range from Newtonian flow for pure water towards non-Newtonian, pseudoplastic flow behaviour with shear thinning in the presence of solid particles[82-84]. Estimated values for the viscosity of the gastric contents are in the range of 10 to 2000 mPa·s[85].

Gastric motility is characterized by two different gastric motor patterns that originate from pacesetter cells located at the greater curvature of the corpus. In the fasted state, the interdigestive migrating motor complex (IMMC) occurs that enables the emptying of non-digestible objects from the gastric lumen during phases of high intensity with maximum pressures in the pyloric region of up to 300 mbar[85b,c]. One IMMC front moves from the proximal stomach to the ileum every 1 to 2 h[86]. The IMMC is interrupted by meal ingestion as the digestive motor activity is initiated. The intensity of the gastric pressure waves is typically lower in the fed state than during phases of high intensity in fasted state[87].

The shortage of in vivo data on gastric flow is due to the experimental difficulties for these in vivo determinations.

However, Boulby et al. observed peak velocities of 2 to 8 cm/s[88]. Computer simulations based on computational fluid dynamics have also been performed but reported a rather broad range of estimated values[89,90]. Under postprandial conditions liquids may probably also be cleared within a few minutes from the stomach due to a mechanism called "Magenstrasse"[91].

As for hydrodynamics, data on intragastric mechanical conditions are highly variable. It seems that the antral grinding forces represent the highest shear forces acting on solids in the fed stomach with grinding force values in the range of 0.2 to 1.89 N[92].

During digestion only liquids and small suspended particles are delivered to the small intestine whilst larger particles are retained by gastric sieving mediated by pylorus[93]. Due to the diversity of the relevant food parameters it is not possible to define a clear cut-off size for the emptying through pylorus[94,95].

Liquids are emptied according to first-order kinetics with emptying rates that are influenced by both caloric content and meal composition. Ranges are reported from 2 to 4 mL/min, where initial emptying rates may reach values of up to 10 to 40 mL/min[74,96,97]. Comparable high gastric emptying rates are also observed after ingestion of water (non-caloric liquids) under fasting conditions[98]. Solid particles are emptied according to a biphasic pattern.

Intestinal Surface Area and Effective Permeability

The surface area of the gut is commonly regarded as a long muscular tube, which is increased by folding, and by small intestinal villi and microvilli. Based on static morphology, several workers have calculated the apparent mucosal surface area of the small intestine after removal, fixation and staining to be approximately 2.2 $m^2$ [99]. It appears that for nutrition, there is an excess capability and only the top of the villus may be utilized for absorption of nutrients. The villus folding change dynamically with transit of food and the microvilli break off to form mixed micellar phases near the apical boundary. The effective epithelial surface area is highly dynamic and is affected by nutritional status, exposure to noxious agents and by the luminal viscosity. A recent literature review[100] indicates a total length of ~5 m (oroanal), where approximately 70% refers to the small intestine (major region for nutrient uptake). There exists a considerable interindividual variation. The inner diameter of the small intestine averages 2.5 cm and that of the large intestine averages 4.8 cm. The mucosa of the small intestine is enlarged ~1.6 times by the plicae circulares. It is expected that villi and microvilli together amplify the small intestinal surface area by 60-120 times. Surface amplification due to microvilli in the colon is ~6.5 times. The mean total mucosal surface of the digestive tract interior averages ~32 $m^2$, of which about 2 $m^2$ refers to the large intestine[100].

Effective human small intestinal permeability ($P_{eff}$) is often based on multiple parallel transport processes. Drugs with a jejunal (in vivo) $P_{eff} > 1.5 \times 10^{-4}$ cm/s will be completely absorbed no matter which transport mechanism(s) are utilized. Many drugs that are significantly effluxed in vitro have a rapid and complete intestinal absorption (i.e. >85%) mediated by passive transcellular diffusion. The human intestinal epithelium has a large resistance (i.e. low $P_{eff}$) towards large and hydrophilic compounds. In addition, the paracellular route has a low contribution for compounds larger than approximately molecular weight 200.

The pH of the GI Tract

The intraluminal pH throughout GI tract affects release, dissolution and solubility of pharmaceutical excipients, API and the digestion of diet and may have a strong effect on the activity of this locally acting product. In the fasted state the gastric pH value of healthy adults is reported to be within pH 1 to pH 3 and represent no gender differences[101-103]. In elderly patients and also as a function of ethnic difference, various degrees of achlorhydria have been reported[104]. The daily intake of food causes rises in pH, with fatty meals causing a sustained rise in proximal gut pH, which may be important if a heavy meal is taken at night. After a high-fat breakfast, the maximum gastric peak pH was reached within the first 5 min and pH decreased gradually to values below pH 3 after 1-2 hours. Due to regional differences in the presence of acid secreting glands, pH gradients in the stomach contents have been observed[103,100]. The data also reflects the observation that in the stomach, the pH in the fundus will typically be one pH unit higher than in the pyloric antrum. In the fed stomach, the sampling device can find itself in pockets of acid or in the food mass[105].

GI Tract Transit and Motility

In normal GI tract physiology, a balance exists between propulsive, peristaltic movements and mixing contractions, which are controlled by signalling between external nerves, especially the vagus, by intestinal short-range pathways and through the plexii. Local responses also occur and may cause spasm. These different conditions (i.e. fasted and fed states) together with various physiological status of GI tract are causing a both high inter- and intra-individual variability that strongly affects the rate and extent of absorption from various orally administered pharmaceutical products. For a locally acting product, these factors will have a strong influence on effects and side-effects.

The fasting and fed GI motilities are distinct and different[106]. In the fed mode, contractions travel down the wall of the stomach, originating below the fundus and forming an annular ring, the pyloric cylinder. Towards the pylorus, the walls collapse, squeezing the contents through a partially closed sphincter and causing retropulsion of larger particles back into the stomach. The mechanism sieves the contents, retaining larger objects (such as enteric coated particles and/or other pharmaceutical related particles) for trituration and is a major determinant of the gastric emptying and onset of drug absorption for any pharmaceutical solid dosage form. Disintegrating objects, near the sphincter are emptied as a series of pulses. This wave of contraction travels then from the stomach to the terminal ileum and then wear-off and disappears.

The luminal conditions change along the GI tract and strongly affect the in vivo release, dissolution, solubility and permeability and accordingly the in vivo performance of any pharmaceutical dosage (i.e. overall rate and extent of absorption)[107-109]. The intraluminal pressure following the passage through the pyloric sphincter and ileocaecal valve may reach values of up to 300 mbar[110]. Furthermore, similar pressure amplitudes have also been reported to exist in the colon[111]. These high-pressure events might affect release mechanism(s) from MR dosage forms. The small intestinal transit time is in the range of 3-5 hrs and appears to be independent upon the dosage form[112]. However, this value probably reflects the typical feeding regimen used in these specific clinical trials as small intestinal transit is triggered by food intake via a mechanism known as gastro-ileocaecal reflex[113,114]. Movement of dosage forms through the small intestine is characterized by typically short episodes of transport where peak velocities of up to 50 cm/s may be reached (jet propulsion) and phases of rest[115]. Typically, dosage forms spend most of the total transit time at rest in the small intestine, typically in the terminal ileum. Under fasting conditions, dosage forms are not necessarily in continuous contact with intestinal water[113].

Presence of GI-Fluids

GI fluids are produced by saliva, gastric and intestinal secretions, pancreatic secretions and water as described above. The small intestine is a very efficient absorber of water, which has a high effective permeability ($P_{eff}$) in the jejunum in vivo, approximately $2 \times 10^{-4}$ cm[116][117]. The gastric emptying rate (described as half-time) of water from a fasted stomach is approximately 10 to 15 minutes or less. After emptying into the small intestines, water is quickly absorbed into the systemic circulation. In imaging studies (magnetic resonance imaging; MRI), residual water can only be seen in a few pockets along the small intestines[113]. Free water is rarely seen in the colon[113].

GI Absorption in the Fed State

The two APIs (orlistat and acarbose) and the formulated oral MR dosage form according to the present invention is designed to act via local mechanisms that result in therapeutic effect on reduction of both weight and cardiovascular risk factors. Any of these two APIs in this novel oral MR formulation mediate their therapeutic effects via local mechanisms located in the small and large intestine, but in particular ileum. The main mechanism of action is based on a two-step principle where specific enzyme inhibition is the first step to cause a delayed digestion where the formed ligands originating from the diet will act on receptors throughout the GI tract. Moreover, the energy inhibiting properties of orlistat will still be present, although to a lower degree. There is no pharmacological effect in the systemic circulation that adds to the therapeutic effect, which means that the local concentration-time profile throughout the GI tract and the interaction with enzyme is crucial for both effects and side-effect panorama. Accordingly, these APIs have biopharmaceutical and pharmaceutical properties that lead to low rate and extent of GI absorption. For instance, acarbose has very hydrophilic properties (log P −8.1) that classifies the API as a Biopharmaceutical Classification System (BCS) class III drug[68,118]. It has also been reported that the intestinal absorption (fa) and bioavailability are below 5%[119]. Orlistat has very lipophilic properties (log P 8.4) that classifies the API as a Biopharmaceutical Classification System (BCS) class II or IV drug[68,118]. It has also been reported that the intestinal absorption (fa) and bioavailability is below 5%[24]. The very lipophilic properties of orlistat predict that the effective small intestinal permeability might be between low to high, but the low rate and extent of intestinal absorption is explained by the low solubility and low dissolution rate in the GI fluids. A composition of the invention is designed taken into account the different physico-chemical properties and the different mechanisms of action of the two APIs.

Other Aspects of the Invention

Other aspects of the invention appear from the appended claims. The details described above apply mutatis mutandis to the other aspects as well.

In particular, the invention also relates to
A. A method for the treatment or prevention of: overweight and obesity; type 2 diabetes; Elevated blood glucose level (such as impaired glucose tolerance), Polycystic ovarian syndrome; Disorders of lipoprotein metabolism and other lipidemias (such as hyperglyceridemia); Nonalcoholic fatty liver disease (NAFLD); Nonalcoholic steatohepatitis; or metabolic syndrome, the method comprising administering a modified-release composition as defined herein.
B. A modified-release composition as described in detail hereim, but wherein part G2B and G3 are excluded.
C. A modified release composition as described herein, but wherein part G1 and G2A are excluded.
D. A modified-release composition as described herein for use in triggering the gastro-intestinal brake as defined in this application.
E. A method for the treatment or prevention of: overweight and obesity; type 2 diabetes; Elevated blood glucose level (such as impaired glucose tolerance), Polycystic ovarian syndrome; Disorders of lipoprotein metabolism and other lipidemias (such as hyperglyceridemia); Nonalcoholic fatty liver disease (NAFLD); Nonalcoholic steatohepatitis; or metabolic syndrome, the method comprising administering a modified-release composition as described herein.
F. A modified-release composition as described herein for use in the treatment of overweight and obesity; type 2 diabetes; Elevated blood glucose level (such as impaired glucose tolerance), Polycystic ovarian syndrome; Disorders of lipoprotein metabolism and other lipidemias (such as hyperglyceridemia); Nonalcoholic fatty liver disease (NAFLD); Nonalcoholic steatohepatitis; or metabolic syndrome.
G. A cosmetic method for reducing body weight, the method comprising administering to a subject in need thereof a modified-release composition as described herein.

LEGENDS TO DRAWING

FIG. 1a-b. The pH dependent degradation of orlistat (ORL) and acarbose (ACA) when the solubility from a powder was investigated at 37° C. The degradation product was also observed in the chromatogram.

FIG. 2. A schematic overview of how digested nutrients act through various mechanisms to affect gastrointestinal motility and satiety[35].

Figure 3:
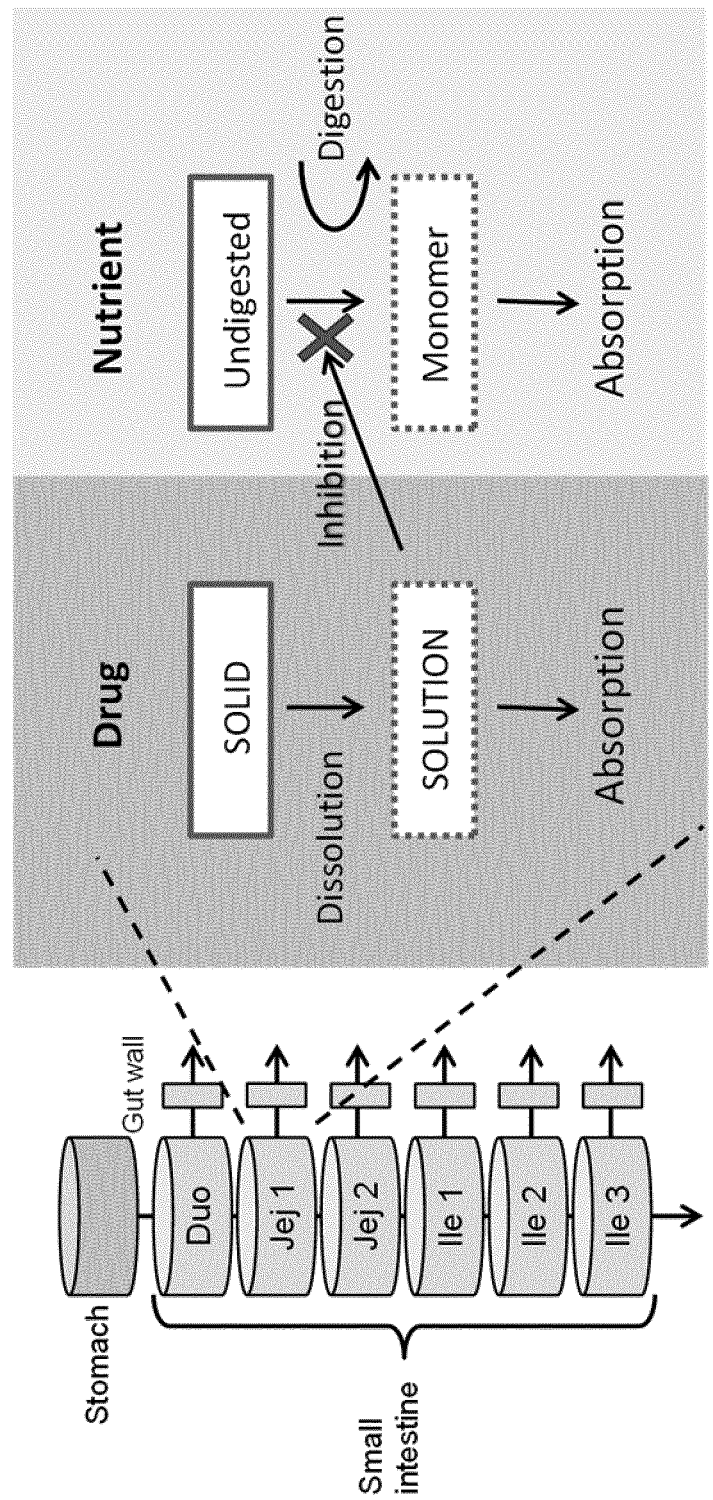

FIG. 3. A schematic view of the gastrointestinal simulation model. To the left, the seven ideal tanks of the gastrointestinal tract. To the right the interplay between general biopharmaceutical processes and the enzyme inhibition.

Figure 4A:
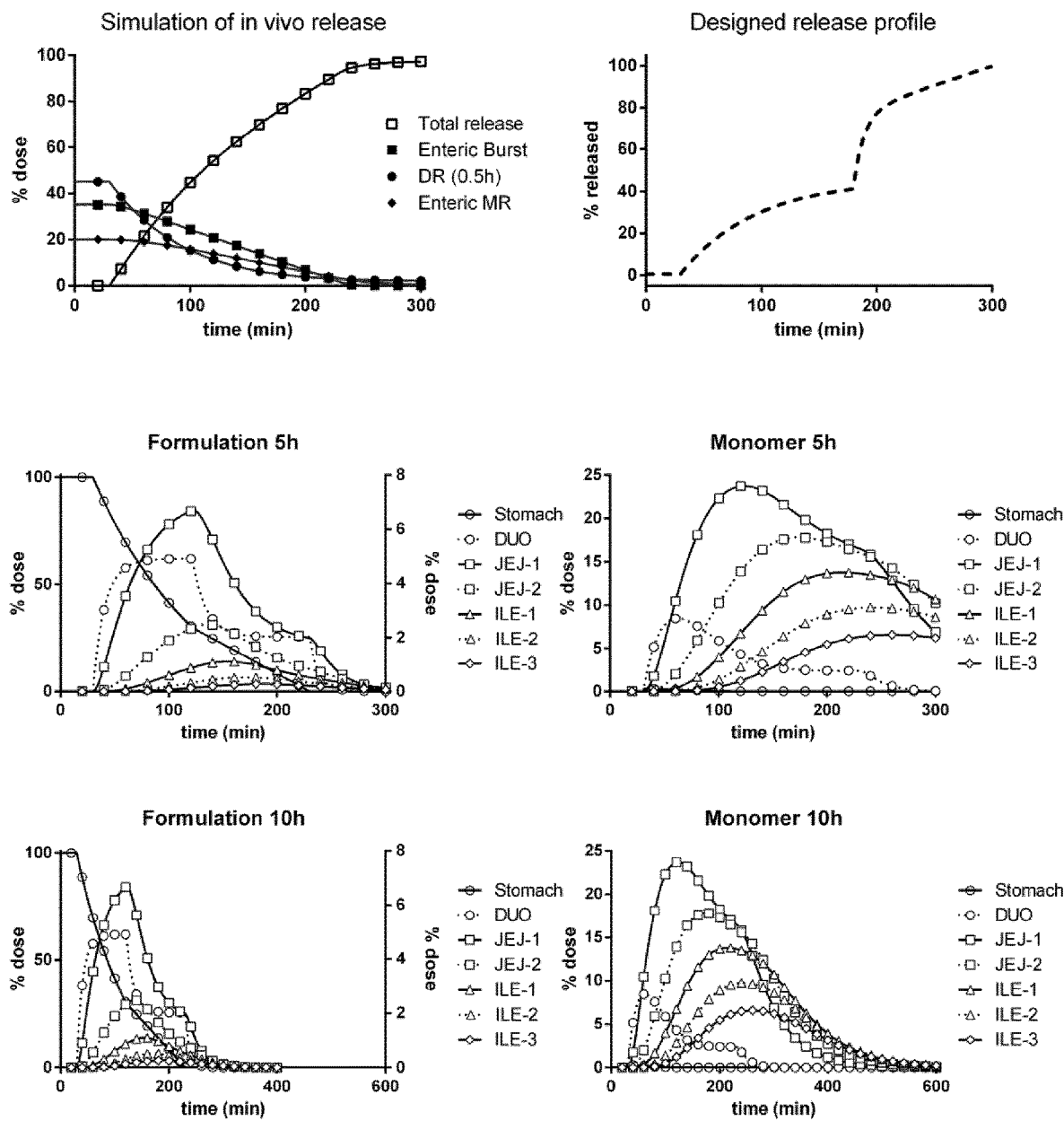
Figure 4B:
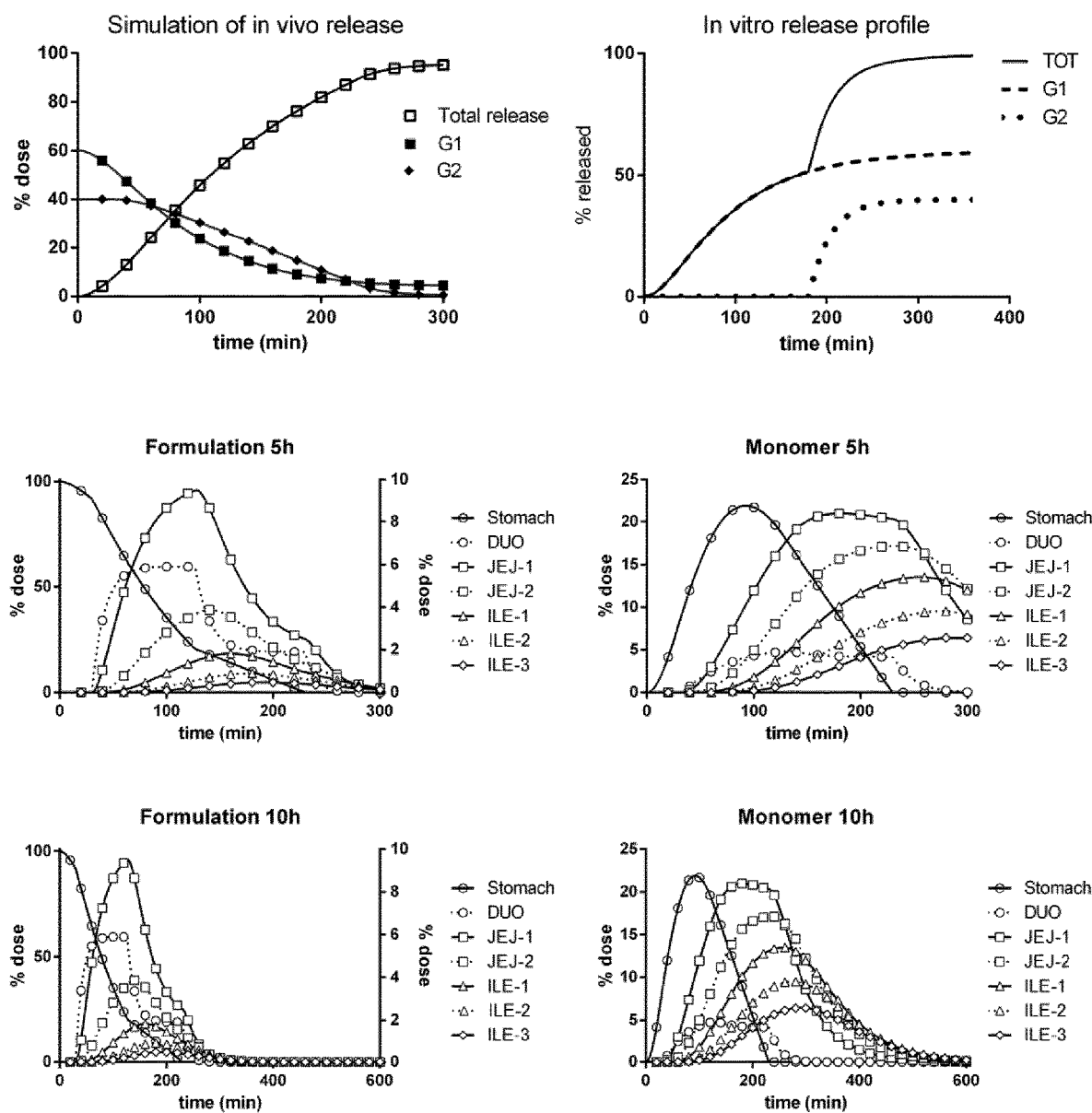

FIG. 4a-b. In the two set of figures above the modelling and simulations of the in vivo release profile based on (a) an ideal release profile and (b) measured in vitro release profile for acarbose are presented. a. In the two figures above the modelling and simulations of the in vivo release profile and the ideal release profile for acarbose are presented. Below in the four figures the local gastrointestinal amount of acarbose (both as a monomer and in the formulation) over time in the different GI segments 5 and 10 hours post dosing. It is clear that the highest luminal concentration of unabsorbed drug (amount left in the luminal GI-segment) is highest in the proximal small intestine and lower in the stomach and distal small intestine. b. In the two figures above the modelling and simulations of the in vivo release profile based on the measured in vitro release profile for acarbose are presented. Below in the four figures the local gastrointestinal amount of acarbose (both as a monomer and in the formulation) over time in the different GI segments 5 and 10 hours post dosing are shown based on the in vitro release data. It is clear that the highest luminal concentration of unabsorbed drug (amount left in the luminal GI-segment) is highest in the proximal small intestine and in the stomach and lower in the distal small intestine. This will provide this oral MR product with the target of the mechanisms of action as planned. If only the curves for acarbose or orlistat, respectively, are considered, these curves are models and simulations of the in vivo release profile based on the measured in vitro release profile for an acarbose-containing composition of the invention (i.e. without orlistat) or an orlistat-containing composition of the invention (i.e. without acarbose).

Figure 5A:
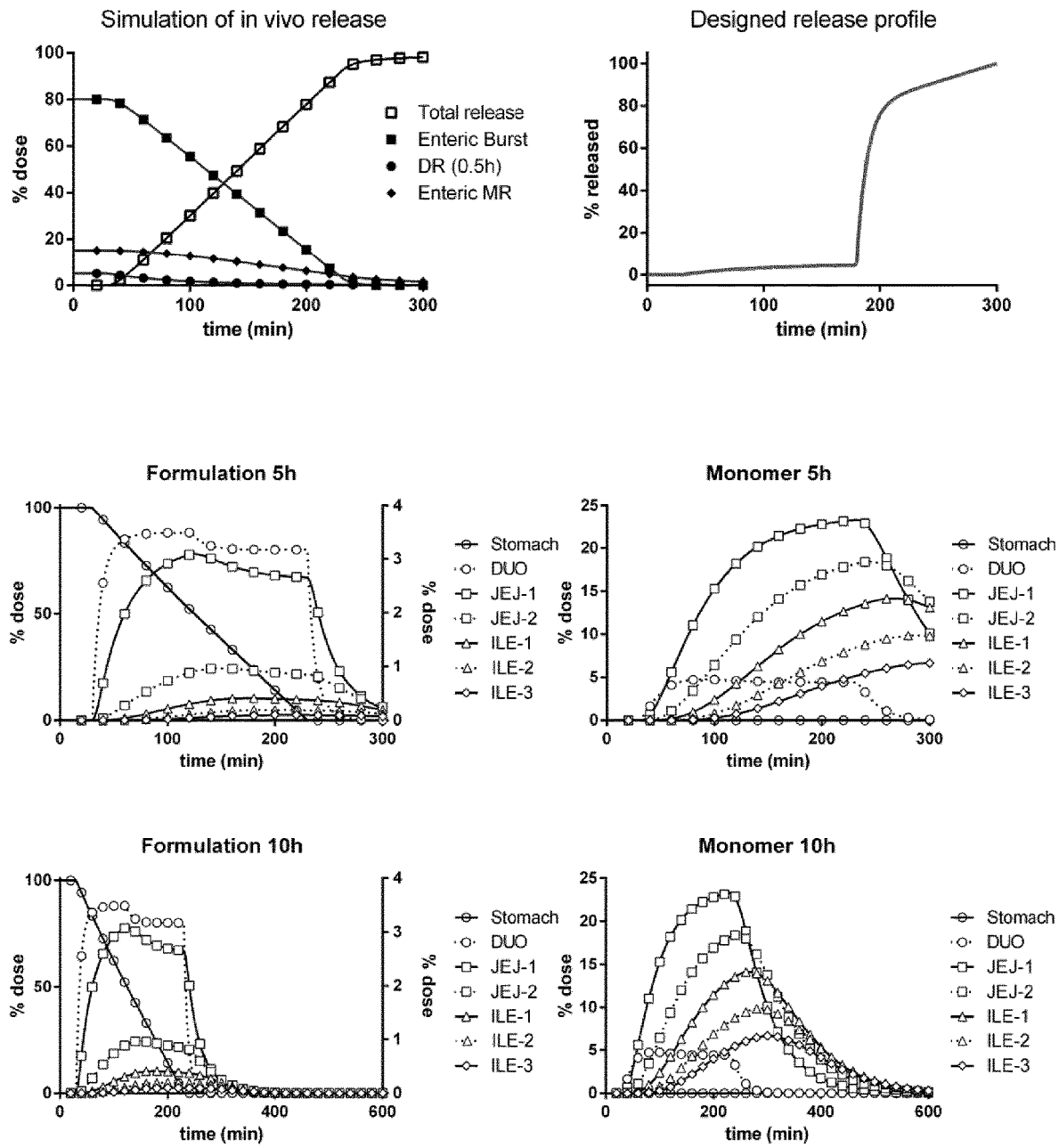
Figure 5B:
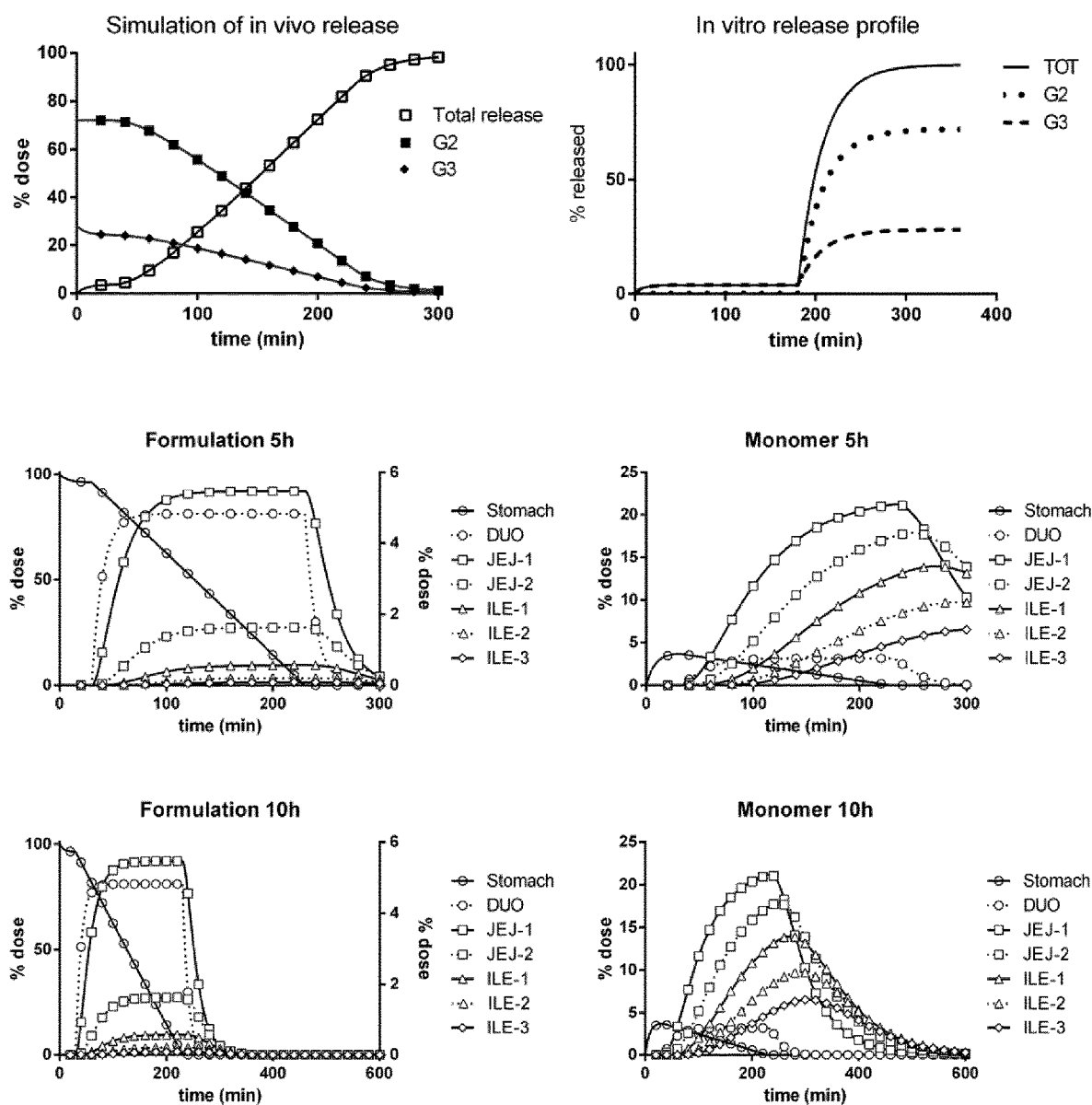

FIG. 5a-b. In the two set of figures above the modelling and simulations of the in vivo release profile based on (a) an ideal release profile and (b) measured in vitro release profile for orlistat are presented. a. In the two figures above the modelling and simulations of the in vivo release profile and the ideal release profile for orlistat are presented. Below in the four figures the local gastrointestinal amount of orlistat (both as a monomer and in the formulation) over time in the different GI segments 5 and 10 hours after dosing. It is clear that the highest luminal concentration of unabsorbed drug (amount left in the luminal GI-segment) is highest in the proximal small intestine and in the stomach and lower in the distal small intestine. b. In the two figures above the modelling and simulations of the in vivo release profile based on the measured in vitro release profile for orlistat are presented. Below in the four figures the local gastrointestinal amount of orlistat (both as a monomer and in the formulation) over time in the different GI segments 5 and 10 hours post dosing are shown based on the in vitro release data. It is clear that the highest luminal concentration of unabsorbed drug (amount left in the luminal GI-segment) is highest in the proximal small intestine and lower in the stomach and in the distal small intestine. This will provide this oral MR product with the target of the mechanisms of action as planned. If only the curves for acarbose or orlistat, respectively, are considered, these curves are models and simulations of the in vivo release profile based on the measured in vitro release profile for an acarbose-containing composition of the invention (i.e. without orlistat) or an orlistat-containing composition of the invention (i.e. without acarbose).

Figure 6:
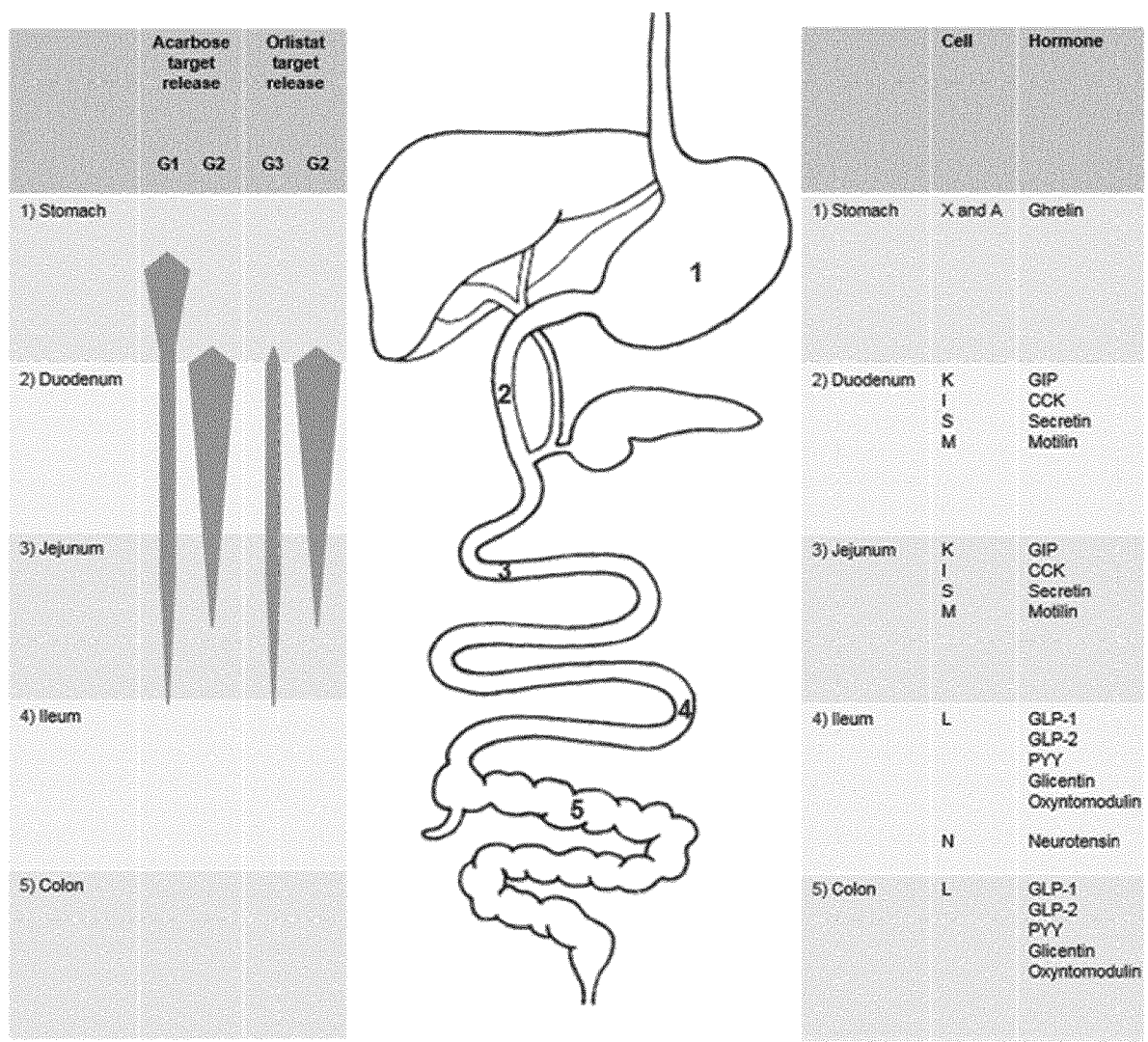

FIG. 6. Target drug release and cell/hormone disposition in the GI tract.

Figure 7B:
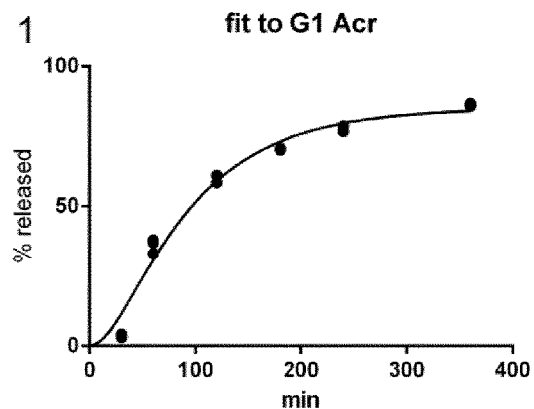
Figure 7B:
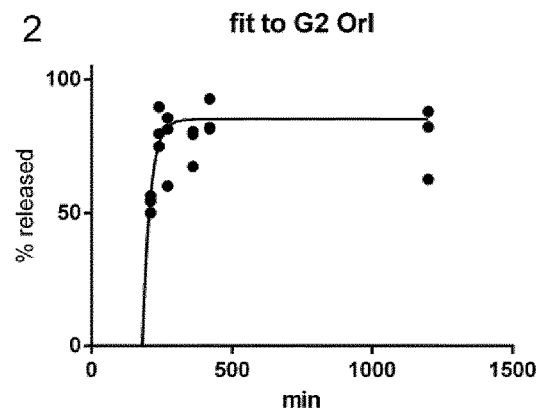
Figure 7B:
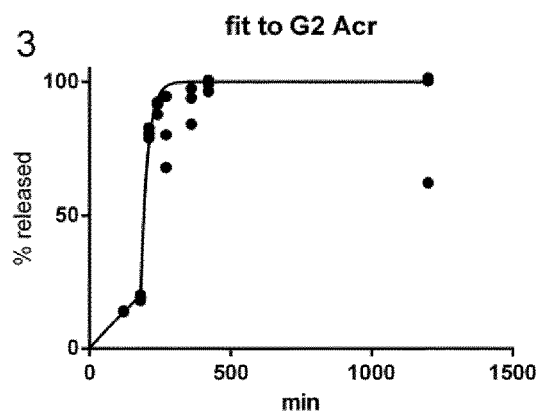
Figure 7B:
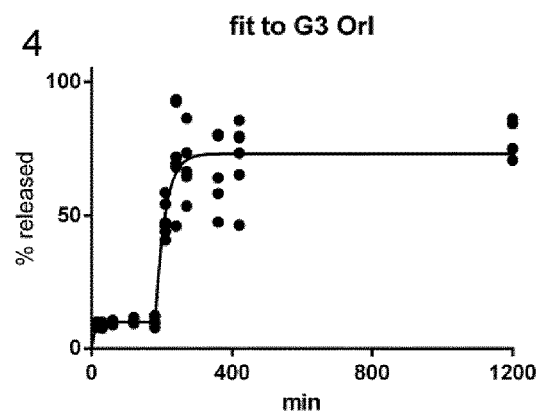
Figure 7B:
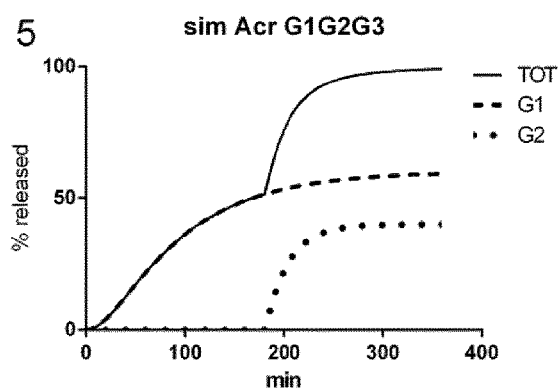
Figure 7B:
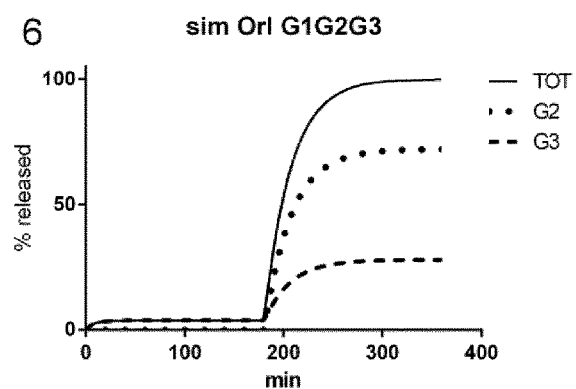

FIG. 7a-b. Target release profiles of acarbose (ACAR) and orlistat (ORL), where 0-3 hours corresponds to average hold time (First part release) in the stomach, 3.0-3.5 hours (Second part release) to proximal small intestine and 3.5-5.0 hours (Third part release) to jejunum. b. To each investigated fraction of the dosage form (G1 and G2 for acarbose and G2 and G3 for orlistat) a release model was fitted to the observed in vitro data (plot 7b.1-4). The observations are represented by dots and the model fitted curve is shown as a solid line. The two plots in the bottom (7b.5 and 7b.6) display the simulated overall combined release (solid line) based on the observed in vitro release data for acarbose (G1 and G2) and orlistat (G2, and G3), respectively. If only the curves for acarbose or orlistat, respectively, are considered, these curves are models and simulations of the in vivo release profile based on the measured in vitro release profile for an acarbose-containing composition of the invention (i.e. without orlistat) or an orlistat-containing composition of the invention (i.e. without acarbose).

FIG. 8. Five dosage form design principles. G=Granule.

FIG. 9. After oral administration together with any of the meals, the APIs will be delivered to the three different regions in the GI tract.

FIG. 10. Schematic overview of most relevant processes involved in drug release, absorption and bioavailability.

FIG. 11. Individual dissolution profiles for acarbose for Example 4H G1+G2+G3 multiple-unit capsule in 25 mM phosphate buffer at pH 3.2 during time 0-180 min and at pH 6.5>180 min with addition of 0.5% SDS at 180 min.

FIG. 12. Individual dissolution profiles for orlistat for Example 4H G1+G2+G3 multiple-unit capsule in 25 mM phosphate buffer at pH 3.2 during time 0-180 min and at pH 6.5>180 min with addition of 0.5% SDS at 180 min.

FIG. 13. Mean dissolution profile for acarbose, G1 ethylcellulose/HPMC-coated MCC-spheres (G1 346670) from Example 4H multiple-unit capsule in 25 mM phosphate buffer at pH 3.2 during time 0-180 min and at pH 6.5>180 min with addition of 0.5% SDS at 180 min.

FIG. 14. Mean dissolution profile for acarbose, G2 enteric coated MCC-spheres (346626) from Example 4H multiple-unit capsule in 25 mM phosphate buffer at pH 3.2 during time 0-180 min and at pH 6.5>180 min with addition of 0.5% SDS at 180 min.

FIG. 15. Mean dissolution profile for orlistat, G2 enteric coated MCC-spheres (346626) from Example 4H multiple-unit capsule in 25 mM phosphate buffer at pH 3.2 during time 0-180 min and at pH 6.5>180 min with addition of 0.5% SDS at 180 min.

FIG. 16. Individual dissolution profiles for orlistat, G3 wet granulation from Example 4H multiple-unit capsule in 25 mM phosphate buffer at pH 3.2 during time 0-180 min and at pH 6.5>180 min with addition of 0.5% SDS at 180 min.

Figure 17:
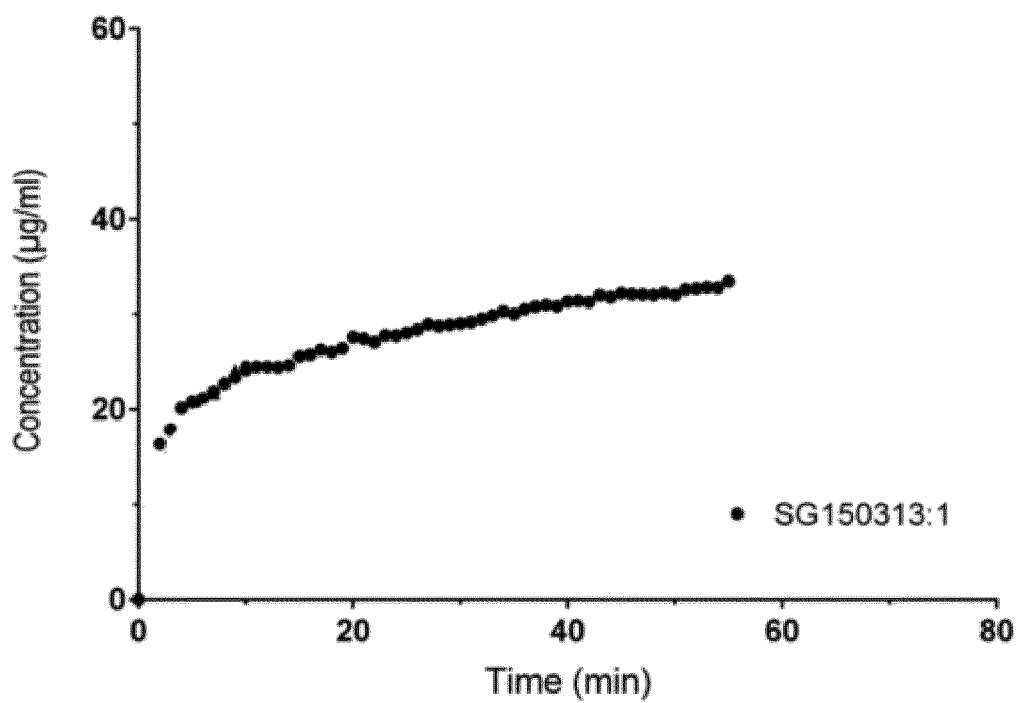

FIG. 17. Mean dissolution profile for acarbose, G1 extruded ethylcellulose/HPMC (SG150313:1) from Example 1J multiple-unit tablet in 50 mM phosphate buffer at pH 6.8.

Figure 18:
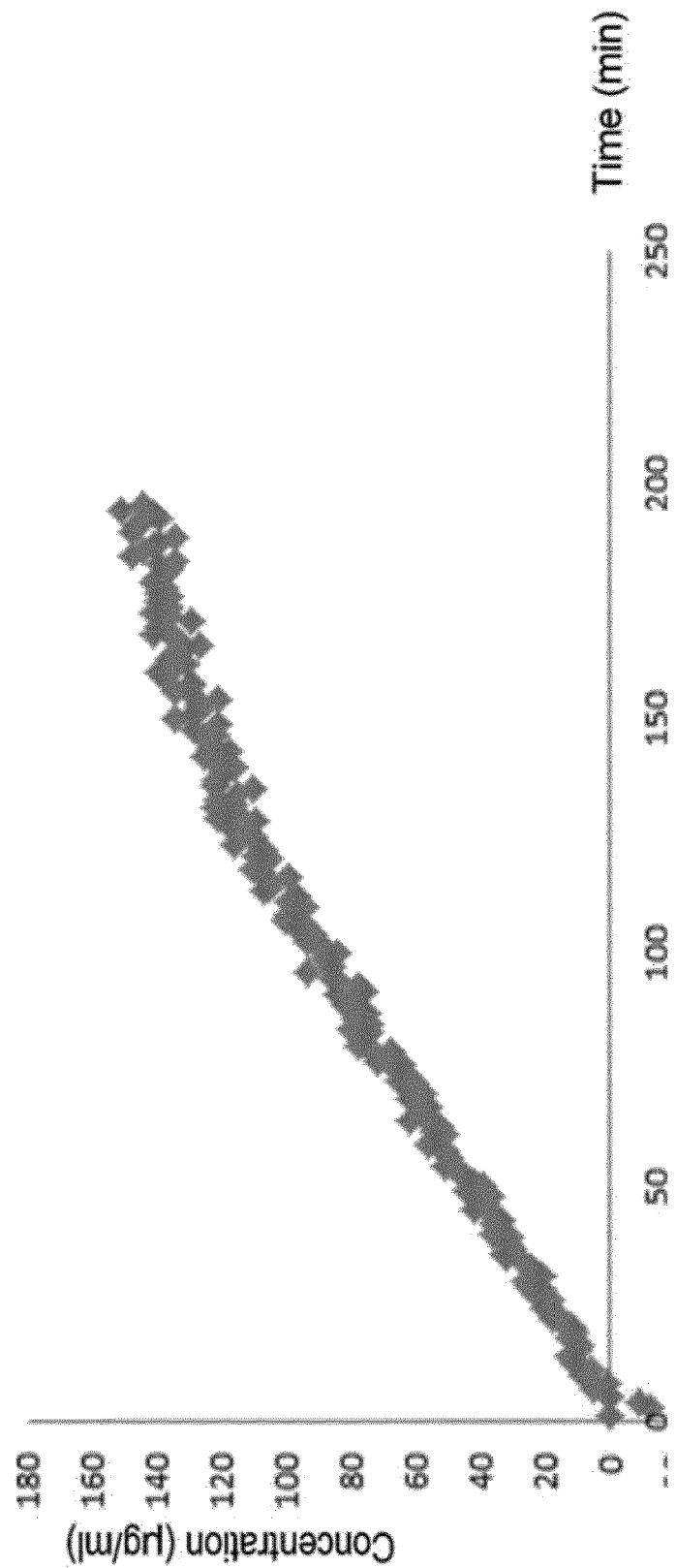

FIG. 18. Dissolution profile for acarbose, G1 extruded hard fat/GMS from Example 1M multiple-unit tablet in 50 mM phosphate buffer at pH 3.5 and 3.0% SDS.

FIG. 19. Dissolution profile for acarbose, G2 enteric coated extruded pellet core from Example 1K multiple-unit tablet in 100 mM phosphate buffer at pH 3.2 during time 0-180 min and at pH 6.5>180 min.

FIG. 20. Dissolution profile for orlistat, G2 enteric coated extruded pellet core from Example 1K multiple-unit tablet in 25 mM phosphate buffer at pH 3.2 during time 0-180 min and at pH 6.5>180 min with addition of 0.5% SDS at 180 min.

FIG. 21. Roche patent formulation (EP 0638317 A1). a: The release of acarbose from the composition. b: The release of orlistat from the composition. Both a. and b. are in 25 mM phosphate buffer at pH 3.2 during time 0-180 min and at pH 6.5>180 min with addition of 0.5% SDS at 180 min.

FIG. 22. Chinese patent formulation (CN 102872062 A). a: The release of acarbose form a separate preparation of the acarbose containing half of the complete formulation. b: The release of orlistat from a separate preparation of the orlistat containing half of the complete formulation. Both a. and b. are in 25 mM phosphate buffer at pH 3.2 during time 0-180 min and at pH 6.5>180 min with addition of 0.5% SDS at 180 min.

FIG. 23a-d. a. In the two set of figures above the modelling and simulations of the in vivo release profile based on (left) a simulation of the release profile and (right) measured in vitro release profile for orlistat are presented from an oral solid dosage form according to patent EP 0638317 A1. Below in the four figures the local gastrointestinal amount of orlistat (both as a monomer and in the formulation) over time in the different GI segments 5 and 10 hours post dosing. It is clear that the highest luminal concentration of unabsorbed drug (amount left in the luminal GI-segment) is highest in the in the stomach and lower in the distal small intestine. This oral dosage form has a very different in vitro release profile than the invention b. In the two figures above the modelling and simulations of the in vivo release profile based on the measured in vitro release profile for acarbose are presented an oral solid dosage form according to patent EP 0638317 A1. Below in the four figures the local gastrointestinal amount of acarbose (both as a monomer and in the formulation) over time in the different GI segments 5 and 10 hours post dosing are shown based on the in vitro release data. It is clear that the highest luminal concentration of unabsorbed drug (amount left in the luminal GI-segment) is highest in the in the stomach and lower in the distal small intestine. This oral dosage form has a very different in vitro release profile than the invention.

c. In the two set of figures above the modelling and simulations of the in vivo release profile based on (left) a simulation of the release profile and (right) measured in vitro release profile for acarbose are presented from an oral solid dosage form according to patent CN 102872062 A. Below in the four figures the local gastrointestinal amount of acarbose (both as a monomer and in the formulation) over time in the different GI segments 5 and 10 hours post dosing. It is clear that the highest luminal concentration of unabsorbed drug (amount left in the luminal GI-segment) is highest in the in the stomach and lower in the distal small intestine. This oral dosage form has a very different in vitro release profile than the invention d. In the two figures above the modelling and simulations of the in vivo release profile based on the measured in vitro release profile for orlistat are presented an oral solid dosage form according to patent CN 102872062 A. Below in the four figures the local gastrointestinal amount of orlistat (both as a monomer and in the formulation) over time in the different GI segments 5 and 10 hours post dosing are shown based on the in vitro release data. It is clear that the highest luminal concentration of unabsorbed drug (amount left in the luminal GI-segment) is highest in the in the stomach and lower in the distal small intestine. This oral dosage form has a very different in vitro release profile than the invention.

The invention is illustrated by way of the following non-limiting examples:

MATERIAL AND METHODS

Material

Acarbose (Bayer Shering Pharma AG, Germany and Zhejiang Hisun, China), orlistat (Biocon, India, Chongqing, China, Zhejiang Hisun, China and Ranbaxy, India), microcrystalline cellulose (MCC, Avicel® PH-101, FMC, Ireland), lactose (α-lactose monohydrate, Inhalose® 230 and SuperTab® SD spray-dried, DMV-Fonterra Excipients GmbH & Co.KG, The Netherlands), mannitol (Parteck® M 200, Merck, KGaA, Germany), hydroxypropylmethylcellulose (HPMC K4M), ethylcellulose (with two different viscosities; Ethocel™ 10FP and Ethocel™ 100FP, Dow Chemical Company, USA), sodium carboxymethylcellulose (Blanose™, Ashland, USA) glyceryl monostearate (Alfa Aesar GmbH & Co KG, Germany), sodium laurylmonostearate (sodium stearyl fumarate, Pruv®, JRS Pharma, Germany), ethanol (99.7% w/w, Solveco Chemicals and Kemetyl AB, Sweden) sterile water (Fresenius AB, Sweden), sodium chloride (Sigma-Aldrich, Germany), potassium phosphate monobasic (Sigma-Aldrich, Germany), sodium hydroxide (Fixanal Fluka Analytical, Sigma-Aldrich, Germany), hydrochloric acid (Titripur, Merck KGaA, Germany), sodium docecyl sulfate (sodium lauryl sulphate or "SDS", Sigma-Aldrich, Germany), hydrogenated vegetable oil, type II ("Hard fat", Dynasan® P60, Sasol GmbH, Germany), polysorbate 80 (Tween™ 80, Alfa Aesar GmbH & Co KG, Germany), polyvinylpyrrolidone K25 (Povidone® K25, BASF SE, Germany) and croscarmellose sodium (Ac-Di-Sol®, SD-711, FMC, Ireland). Coating compositions Opadry® (HPMC-based) 03K19229 clear (Colorcon Ltd., UK) and Acryl-EZE® II 493Z120005 yellow (Colorcon Ltd., UK).

In Vitro Dissolution Methods

Method A, HPLC Detection

A composition of the invention aims at fulfilling the following dissolution pattern when tested in accordance with the in vitro dissolution tests described in the United States Pharmacopoeia General Test Chapter on DISSOLUTION <711>[63] using Apparatus 2 (SAM SOTAX automatic sampler connected to HPLC apparatus or Fraction Collector AT7 SMART SOTAX). The following conditions are used; 900 ml vessel volume, paddle at 75 rpm, minigranules are prepared in capsules size TOO white/white, capsules are put into spiral stainless steel sinker 25-27×11 mm. Bi-phasic dissolution medium (900 ml and 37.0±0.5° C.,) is employed, for t=0 h to t=3 h, 25 mM $KH_2PO_4$ and pH=3.2 (corresponding to in vivo gastric fed state conditions) and for t=3 h to t=8 h, 25 mM $KH_2PO_4$ and pH=6.5 (adjusted by NaOH 5M) and addition of Sodium Dodecyl Sulphate to a total concentration of 0.5% w/w (corresponding to in vivo intestinal fed state conditions).

Samples are collected in time series. The amount of released API (orlistat and/or acarbose) is determined by HPLC (HPLC Agilent Technologies type 1100 or 1200 with DAD detector, monitored with OpenLab software, Agilent Technologies) as follows: 2 HPLC columns in series; Hibar, Purosphere, RP-8 (L=150 mm, internal diameter 4.6 mm, particle size 5 μm) and APS-2-Hypersyl (L=250 mm, internal diameter 4 mm, particle size 5 μm), flow rate 2 mL/min, injection volume 50 μL, sample temperature 25° C., column temperature 40° C., run time 15 minutes. Elution buffer solution: 0.6 g $KH_2PO_4$ and 0.35 g $Na_2HPO_4$, $2H_2O$ in 1 L of water, mobile phase buffer solution: 28% v/v; acetonitrile: 72% v/v. Detection by UV spectrometer at 210 nm. A standard preparation of acarbose and orlistat in water/acetonitrile 50/50 v/v with 3 external calibration points was used. The samples was not prepared and put into amber vials.

Method B, UV Detection

The dissolution studies that were performed using a USP basket (USP I apparatus) dissolution instrument (PTWS 310, Hainburg, Germany) equipped with 1000 ml vessels. A standard volume of 500 mL at 37±2° C., sample amount of 150 mg and stirring rate 100 rpm were used. Acarbose absorbance maximum at 210 nm. The buffer dissolution media was prepared by mixing 250 mL 0.2 M potassium dihydrogen phosphate with 112 mL 0.2 M (23.31 g 1 M) sodium hydroxide and diluted to 1000 mL with deionized water. The pH was measured to be ~6.8±0.1. Prior to filling the vessels, the compendial media was de-aerated according to the methodology described in the Ph. Eur., i.e. through heating (~41° C.) followed by vacuum filtering (filter porosity 0.22 μm). The temperature of the dissolution media during testing was maintained at 37±0.5° C. Each dissolution test (n≥2) was preceded at the longest for about 3 hours. The stirring was initiated directly as the baskets were lowered in the medium whereas the stirring of the paddles was started prior to addition of granules. When using baskets the granules were weighed directly into a fine meshed plastic net bag placed at the bottom of the basket. When using paddles the granules were added directly in the medium thus enabling direct dispersion of the particles. The weight of the granules was chosen to correspond to doses of 20 mg drug.

Method B has only been used for spheronized G1 pellets containing acarbose and the dissolution rate limiting excipients ethylcellulose/hydroxypropylmethylcellulose or hard fat/glyceryl monostearate—see FIG. 17 and FIG. 18. All other in vitro dissolution tests have been performed with HPLC detection according to method A as described above or with slight differences in ionic strength and addition of sodium lauryl sulphate during development.

Example 1. Multiple-Unit Tablet

Example 1A, Orlistat 90 mg/Acarbose 30 mg

| Ingredient | % w/w |
|---|---|
| $DR_{DC}$-$PR_{GASTRIC}$ Granules (G1) | |
| Acarbose | 0.2-1 |
| Filler | 0-20 |
| Disintegrant | 0-5 |
| Binder | 0-5 |
| Prolonged release polymer | 0-10 |
| Coating polymer, 30-60 min delay | 1-10 |
| Sub-total: | 1-51 |
| $DR_{EC}$-$RR_{PROX\,SI}$ Granules (G2) | |
| Orlistat | 4-12 |
| Acarbose | 2-4 |
| Filler | 0-10 |
| Binder | 0-5 |
| Disintegrant | 0-10 |
| Solubilizer | 0-5 |
| Sub-coating polymer | 0-5 |
| Enteric coating polymer | 1-11 |
| Sub-total: | 7-52 |
| $DR_{DC}$-$PR_{GASTRIC}$ Granules (G3) | |
| Orlistat | 3-6 |
| Prolonged release polymer | 10-40 |
| Coating polymer, 30-60 min delay | 0-10 |

Example 1A, Orlistat 90 mg/Acarbose 30 mg

| Ingredient | % w/w |
|---|---|
| Sub-total: | 13-56 |
| Extragranular ingredients | |
| Filler | 0-50 |
| Glidant | 0-2 |
| Lubricant | 0-2 |
| Total: | 100 |

Example 1B, Orlistat 90 mg/Acarbose 30 mg

| Ingredient | mg/tablet | % w/w |
|---|---|---|
| $DR_{DC}$-$PR_{GASTRIC}$ Granules (G1) | | |
| Acarbose | 5 | 0.6 |
| Filler | 47 | 5.9 |
| Disintegrant | 5 | 0.6 |
| Binder | 3 | 0.4 |
| Prolonged release polymer | 30 | 3.8 |
| Coating polymer, 30-60 min delay | 10 | 1.3 |
| Sub-total: | 100 | 13 |
| $DR_{EC}$-$RR_{PROX\,SI}$ Granules (G2) | | |
| Orlistat | 65 | 8.1 |
| Acarbose | 25 | 3.1 |
| Filler | 30 | 3.8 |
| Binder | 25 | 3.1 |
| Disintegrant | 30 | 3.8 |
| Solubilizer | 5 | 0.6 |
| Sub-coating polymer | 12 | 1.5 |
| Enteric coating polymer | 48 | 6.0 |
| Sub-total: | 230 | 29 |
| $DR_{DC}$-$PR_{GASTRIC}$ Granules (G3) | | |
| Orlistat | 25 | 3.1 |
| Prolonged release polymer | 215 | 27 |
| Coating polymer, 30-60 min delay | 10 | 1.3 |
| Sub-total: | 250 | 31 |
| Extragranular ingredients | | |
| Filler | 211 | 26 |
| Glidant | 4 | 0.5 |
| Lubricant | 5 | 0.6 |
| Total: | 800 | 100 |

Example 1C, Orlistat 90 mg/Acarbose 30 mg

| Ingredient | mg/tablet | % w/w |
|---|---|---|
| $DR_{DC}$-$PR_{GASTRIC}$ Granules (G1) | | |
| Acarbose | 5 | 6.3 |
| Mannitol | 47 | 5.9 |
| Croscarmellose sodium | 5 | 0.6 |
| Polyvinylpyrrolidone | 3 | 0.4 |
| Ethylcellulose | 30 | 3.8 |
| Eudragit L30 D-55 (methacrylic acid - ethyl acetate copolymer (1:1) dispersion 30 percent) | 10 | 1.3 |
| Sub-total: | 100 | 13 |
| $DR_{EC}$-$RR_{PROX\,SI}$ Granules (G2) | | |
| Orlistat | 65 | 8.1 |
| Acarbose | 25 | 3.1 |
| Microcrystalline cellulose | 30 | 3.8 |
| Polyvinylpyrrolidone, Povidone | 25 | 3.1 |
| Sodium starch glycolate, Primojel | 30 | 3.8 |
| Sodium lauryl sulphate, SDS | 5 | 0.6 |
| Opadry II Clear (macrogol 3350, polysorbate 80, polyvinyl alcohol and talc) | 12 | 1.5 |
| Acryl-EZE Clear (methacrylic acid copolymer type C, sodium lauryl sulphate, macrogol, talc, sodium bicarbonate and colloidal silica, anhydrous) | 48 | 6.0 |
| Sub-total: | 230 | 29 |
| $DR_{DC}$-$PR_{GASTRIC}$ Granules (G3) | | |
| Orlistat | 25 | 3.1 |
| Hypromellose, HPMC K100 | 215 | 27 |
| Eudragit L30 D-55 (methacrylic acid - ethyl acetate copolymer (1:1) dispersion 30 percent) | 10 | 1.3 |
| Sub-total: | 250 | 31 |

-continued

| Ingredient | mg/tablet | % w/w |
|---|---|---|
| Extragranular ingredients | | |
| Isomalt | 130 | 16 |
| Mannitol | 60 | 7.5 |
| Xylitol | 21 | 2.6 |
| Silica, colloidal anhydrous | 4 | 0.5 |
| Magnesium stearate | 5 | 0.6 |
| Total: | 800 | 100 |

Example 1D, Orlistat 90 mg/Acarbose 30 mg

| Ingredient | mg/tablet | % w/w |
|---|---|---|
| $DR_{DC}$-$PR_{GASTRIC}$ Granules (G1) | | |
| Acarbose | 5 | 6.3 |
| Mannitol | 47 | 5.9 |
| Croscarmellose sodium | 5 | 0.6 |
| Polyvinylpyrrolidone | 3 | 0.4 |
| Glyceryl monostearate | 30 | 3.8 |
| Eudragit L30 D-55 (methacrylic acid - ethyl acetate copolymer (1:1) dispersion 30 percent) | 10 | 1.3 |
| Sub-total: | 100 | 13 |
| $DR_{EC}$-$RR_{PROX\,SI}$ Granules (G2) | | |
| Orlistat | 65 | 8.1 |
| Acarbose | 25 | 3.1 |
| Microcrystalline cellulose | 30 | 3.8 |
| Polyvinylpyrrolidone, Povidone | 25 | 3.1 |
| Sodium starch glycolate, Primojel | 30 | 3.8 |
| Sodium lauryl sulphate, SDS | 5 | 0.6 |
| Opadry II Clear (macrogol 3350, polysorbate 80, polyvinyl alcohol and talc) | 12 | 1.5 |
| Acryl-EZE Clear (methacrylic acid copolymer type C, sodium lauryl sulphate, macrogol, talc, sodium bicarbonate and colloidal silica, anhydrous) | 48 | 6.0 |
| Sub-total: | 230 | 29 |
| $DR_{DC}$-$PR_{GASTRIC}$ Granules (G3) | | |
| Orlistat | 25 | 3.1 |
| Hypromellose, HPMC K100 | 215 | 27 |
| Eudragit L30 D-55 (methacrylic acid - ethyl acetate copolymer (1:1) dispersion 30 percent) | 10 | 1.3 |
| Sub-total: | 250 | 31 |
| Extragranular ingredients | | |
| Isomalt | 130 | 16 |
| Mannitol | 60 | 7.5 |
| Xylitol | 21 | 2.6 |
| Silica, colloidal anhydrous | 4 | 0.5 |
| Magnesium stearate | 5 | 0.6 |
| Total: | 800 | 100 |

The multiple-unit tablets of Example 1A-D are prepared as follows:

A small scale high-shear mixer, Diosna P1/6 with a 0.5 L granulation bowl was used for blending and granulation. The excipients and APIs were initially dry blended for five minutes (MM-act 690 rpm, CM-set 200 rpm, CM-set 4.4 rpm). For all three granules, the granulate liquid (purified water) was added drop wise to the mixture to avoid gelling and/or formation of lumps. The coating dispersions are prepared layer by layer; when preparing the dispersion place the impeller close to the bottom of the coating solution bucket. The stirring rate was increased until a deep vortex is formed. Add gently the powder to disperse in the vortex. Thereafter, adjust stirring rate so that sedimentation and foaming are avoided. Coat the granules in a standard pellet coater. The coating proceeds, with process controls, to a final target average weight increase after drying (dried to achieve loss on drying less than about 2% w/w determined at 105° C.). When the granules are dry and solidified; add isomalt, mannitol, xylitol and the congealed granules in a tumbling mixer. Mix during 10-30 minutes, depending on mixer. Sieve magnesium stearate through a 100-250 μm sieve, add the magnesium stearate to the tumbling mixer and mix for an additional approximately 2 minutes, depending on mixer. Transfer the final blend to a rotary tablet press and compress tablets with a total weight of 800 mg.

Example 1E, Orlistat 60 mg/Acarbose 20 mg

| Ingredient | % w/w |
|---|---|
| $DR_{DC}$-$PR_{GASTRIC}$ Granules (G1) | |
| Acarbose | 2.0 |
| Film-coating polymer, water-soluble | 1-10 |
| Delayed release coating polymer, poorly water-soluble | 1-5 |
| Coating sphere, filler | 1-5 |
| Sub-total: | 5-20 |
| $DR_{EC}$-$RR_{PROX\,SI}$ Granules (G2) | |
| Orlistat | 7.2 |
| Acarbose | 1.4 |
| Film-coating polymer | 2-6 |
| Coating sphere, filler | 10-30 |
| Surface active agent | 0-10 |
| Enteric coating film based on methacrylic acid copolymer | 20-40 |
| Sub-total: | 45-85 |
| $DR_{DC}$-$PR_{GASTRIC}$ Granules (G3) | |
| Orlistat | 2.8 |
| Surface active agent | 0-2 |
| Filler | 1-5 |
| Sub-total: | 3-10 |
| Extragranular ingredients | |
| Filler | 0-50 |
| Glidant | 0-2 |
| Lubricant | 0-2 |
| Total: | 100 |

Example 1F, Orlistat 60 mg/Acarbose 20 mg

| Ingredient | mg/tablet | % w/w |
|---|---|---|
| $DR_{DC}$-$PR_{GASTRIC}$ Granules (G1) | | |
| Acarbose | 11.7 | 2.0 |
| Hydroxypropyl methylcellulose | 1.6 | 0.3 |
| Ethylcellulose, Surelease | 6.8 | 1.1 |
| Microcrystalline cellulose, Celphere CP 203 | 9.9 | 1.6 |
| Sub-total: | 30.0 | 5.0 |
| $DR_{EC}$-$RR_{PROX\,SI}$ Granules (G2) | | |
| Orlistat | 43.3 | 7.2 |
| Acarbose | 8.3 | 1.4 |

| Ingredient | mg/tablet | % w/w |
|---|---|---|
| Hydroxypropyl cellulose, Klucel | 15.4 | 2.6 |
| Microcrystalline cellulose, Celphere CP 203 | 109 | 18.2 |
| Polysorbate 80, Tween 80 | 5.6 | 0.9 |
| Opadry (HPMC low viscosity grade, 6 cps, tri-acetin, and talc) | 9.4 | 1.6 |
| Eudragit L 100-55 (methacrylic acid - ethyl acrylate copolymer (1:1) Type A) | 99.4 | 16.6 |
| Triethyl citrate | 10.1 | 1.7 |
| Talc | 74.6 | 12.4 |
| Sub-total: | 375 | 62.5 |
| $DR_{DC}$-$PR_{GASTRIC}$ Granules (G3) | | |
| Orlistat | 16.7 | 2.8 |
| Polysorbate 80, Tween 80 | 5.8 | 1.0 |
| Microcrystalline cellulose | 7.5 | 1.3 |
| Sub-total: | 30.0 | 5.0 |
| Extragranular ingredients | | |
| Isomalt | 84.0 | 14.0 |
| Microcrystalline cellulose | 75.0 | 12.5 |
| Silica, colloidal anhydrous | 3.0 | 0.5 |
| Magnesium stearate | 3.0 | 0.5 |
| Total: | 600 | 100 |

The tablets have good mechanical resistance and dissolution behaviour.

Example 1G, Orlistat 90 mg/Acarbose 30 mg

| Ingredient | mg/tablet | % w/w |
|---|---|---|
| $DR_{DC}$-$PR_{GASTRIC}$ Granules (G1) | | |
| Acarbose | 18.0 | 2.3 |
| Hydroxypropyl methylcellulose | 2.4 | 0.3 |
| Ethylcellulose, Surelease | 10.2 | 1.3 |
| Microcrystalline cellulose, Celphere CP 203 | 14.9 | 1.9 |
| Sub-total: | 45.5 | 5.7 |
| $DR_{EC}$-$RR_{PROX\,SI}$ Granules (G2) | | |
| Orlistat | 65.0 | 8.1 |
| Acarbose | 12.0 | 1.5 |
| Hydroxypropyl cellulose, Klucel | 23.0 | 2.9 |
| Microcrystalline cellulose, Celphere CP 203 | 163 | 20.4 |
| Polysorbate 80, Tween 80 | 8.3 | 1.0 |
| Eudragit L 100-55 (methacrylic acid - ethyl acrylate copolymer (1:1) Type A) | 199 | 24.9 |
| Triethyl citrate | 20.1 | 2.5 |
| Talc | 99.9 | 12.5 |
| Sub-total: | 591 | 73.9 |
| $DR_{DC}$-$PR_{GASTRIC}$ Granules (G3) | | |
| Orlistat | 25.0 | 3.1 |
| Polysorbate 80, Tween 80 | 1.4 | 0.2 |
| Microcrystalline cellulose | 9.3 | 1.2 |
| Sub-total: | 35.7 | 4.5 |
| Extragranular ingredients | | |
| Isomalt | 65.0 | 8.1 |
| Microcrystalline cellulose | 54.8 | 6.9 |
| Silica, colloidal anhydrous | 4.0 | 0.5 |
| Magnesium stearate | 4.0 | 0.5 |
| Total: | 800 | 100 |

The tablets have good mechanical resistance and dissolution behaviour.

Example 1H, Orlistat 60 mg/Acarbose 20 mg

In this example, multiple-unit tablets are prepared. It is identical with example 1F, but G2 has been extruded and the pellet cores are spheronized.

| Ingredient | mg/tablet | % w/w |
|---|---|---|
| $DR_{DC}$-$PR_{GASTRIC}$ Granules (G1) | | |
| Acarbose | 11.7 | 2.9 |
| Hydroxypropyl methylcellulose | 1.6 | 0.4 |
| Ethylcellulose, Surelease | 6.8 | 1.7 |
| Microcrystalline cellulose, Celphere CP 203 | 9.9 | 2.5 |
| Sub-total: | 30.0 | 7.5 |
| $DR_{EC}$-$RR_{PROX\,SI}$ Granules (G2) | | |
| Orlistat | 43.3 | 10.8 |
| Acarbose | 8.3 | 2.1 |
| Microcrystalline cellulose | 65.8 | 16.5 |
| Polysorbate 80, Tween 80 | 13.4 | 3.4 |
| Mannitol | 9.8 | 2.5 |
| Croscarmellose sodium | 5.9 | 1.5 |
| Sodium stearyl fumarate, Pruv | 2.1 | 0.5 |
| Opadry (HPMC low viscosity grade, 6 cps, tri-acetin, and talc) | 4.5 | 1.1 |
| Acryl-EZE (methacrylic acid copolymer Type C, sodium lauryl sulphate, macrogol, talc, sodium bicarbonate and colloidal silica, anhydrous) | 59.5 | 14.9 |
| Sub-total: | 212 | 53.0 |
| $DR_{DC}$-$PR_{GASTRIC}$ Granules (G3) | | |
| Orlistat | 16.7 | 4.2 |
| Polysorbate 80, Tween 80 | 5.8 | 1.5 |
| Microcrystalline cellulose | 7.5 | 1.9 |
| Sub-total: | 30.0 | 7.5 |
| Extragranular ingredients | | |
| Isomalt | 70.0 | 17.5 |
| Microcrystalline cellulose | 54.0 | 13.5 |
| Silica, colloidal anhydrous | 2.0 | 0.5 |
| Magnesium stearate | 2.0 | 0.5 |
| Total: | 400 | 100 |

Example 1I, Orlistat 60 mg/Acarbose 20 mg

G1 is extruded and spheronized with ethylcellulose/hydroxypropylmethylcellulose (HPMC).

| Ingredient | % w/w |
|---|---|
| $DR_{DC}$-$PR_{GASTRIC}$ Granules (G1) | |
| Acarbose | 2.0 |
| Cellulose-based polymer, water-soluble | 1-10 |
| Delayed release polymer, poorly water-soluble | 1-10 |
| Lubricant | 0-5 |
| Sub-total: | 5-20 |
| $DR_{EC}$-$RR_{PROX\,SI}$ Granules (G2) | |
| Orlistat | 7.2 |
| Acarbose | 1.4 |
| Film-coating polymer | 2-6 |
| Coating sphere, filler | 10-30 |
| Surface active agent | 0-10 |
| Enteric coating film based on methacrylic acid copolymer | 20-40 |
| Sub-total: | 45-85 |

-continued

| Ingredient | % w/w |
|---|---|
| DR$_{DC}$-PR$_{GASTRIC}$ Granules (G3) | |
| Orlistat | 2.8 |
| Surface active agent | 0-2 |
| Filler | 1-5 |
| Sub-total: | 3-10 |
| Extragranular ingredients | |
| Filler | 0-50 |
| Glidant | 0-2 |
| Lubricant | 0-2 |
| Total: | 100 |

Example 1J, Orlistat 60 mg/Acarbose 20 mg

G1 is extruded and spheronized with ethylcellulose/hydroxypropylmethylcellulose (HPMC).

| Ingredient | mg/tablet | % w/w |
|---|---|---|
| DR$_{DC}$-PR$_{GASTRIC}$ Granules (G1) | | |
| Acarbose | 11.7 | 2.0 |
| Hydroxypropyl methylcellulose | 22.8 | 3.8 |
| Ethylcellulose, Ethocel 10 FP | 23.4 | 3.9 |
| Sodium stearyl fumarate, Pruv | 0.6 | 0.1 |
| Sub-total: | 58.5 | 9.8 |
| DR$_{EC}$-RR$_{PROX\,SI}$ Granules (G2) | | |
| Orlistat | 43.3 | 7.2 |
| Acarbose | 8.3 | 1.4 |
| Hydroxypropyl cellulose, Klucel | 15.4 | 2.6 |
| Microcrystalline cellulose, Celphere CP 203 | 109 | 18.2 |
| Polysorbate 80, Tween 80 | 5.6 | 0.9 |
| Opadry (HPMC low viscosity grade, 6 cps, triacetin, and talc) | 9.4 | 1.6 |
| Eudragit L 100-55 (methacrylic acid - ethyl acrylate copolymer (1:1) Type A) | 99.4 | 16.6 |
| Triethyl citrate | 10.1 | 1.7 |
| Talc | 74.6 | 12.4 |
| Sub-total: | 375 | 62.5 |
| DR$_{DC}$-PR$_{GASTRIC}$ Granules (G3) | | |
| Orlistat | 16.7 | 2.8 |
| Polysorbate 80, Tween 80 | 5.8 | 1.0 |
| Microcrystalline cellulose | 7.5 | 1.3 |
| Sub-total: | 30.0 | 5.0 |
| Extragranular ingredients | | |
| Isomalt | 70.0 | 11.7 |
| Microcrystalline cellulose | 60.5 | 10.1 |
| Silica, colloidal anhydrous | 3.0 | 0.5 |
| Magnesium stearate | 3.0 | 0.5 |
| Total: | 600 | 100 |

Example 1K, Orlistat 60 mg/Acarbose 20 mg

G1 is extruded and spheronized with ethyl-cellulose/hydroxypropylmethylcellulose (HPMC). G2 is extruded and spheronized pellet cores.

| Ingredient | mg/tablet | % w/w |
|---|---|---|
| DR$_{DC}$-PR$_{GASTRIC}$ Granules (G1) | | |
| Acarbose | 11.7 | 2.9 |
| Hydroxypropyl methylcellulose | 22.8 | 5.7 |
| Ethylcellulose, Ethocel 10 FP | 23.4 | 5.9 |
| Sodium stearyl fumarate, Pruv | 0.6 | 0.2 |
| Sub-total: | 58.5 | 14.6 |
| DR$_{EC}$-RR$_{PROX\,SI}$ Granules (G2) | | |
| Orlistat | 43.3 | 10.8 |
| Acarbose | 8.3 | 2.1 |
| Microcrystalline cellulose | 65.8 | 16.5 |
| Polysorbate 80, Tween 80 | 13.4 | 3.4 |
| Mannitol | 9.8 | 2.5 |
| Croscarmellose sodium | 5.9 | 1.5 |
| Sodium stearyl fumarate, Pruv | 2.1 | 0.5 |
| Opadry (HPMC low viscosity grade, 6 cps, triacetin, and talc) | 4.5 | 1.1 |
| Acryl-EZE (methacrylic acid copolymer Type C, sodium lauryl sulphate, macrogol, talc, sodium bicarbonate and colloidal silica, anhydrous) | 59.5 | 14.9 |
| Sub-total: | 212 | 53.0 |
| DR$_{DC}$-PR$_{GASTRIC}$ Granules (G3) | | |
| Orlistat | 16.7 | 4.2 |
| Polysorbate 80, Tween 80 | 5.8 | 1.5 |
| Microcrystalline cellulose | 7.5 | 1.9 |
| Sub-total: | 30.0 | 7.5 |
| Extragranular ingredients | | |
| Isomalt | 50.0 | 12.5 |
| Microcrystalline cellulose | 45.0 | 11.3 |
| Silica, colloidal anhydrous | 2.0 | 0.5 |
| Magnesium stearate | 2.0 | 0.5 |
| Total: | 400 | 100 |

The dissolution profile of G1 is shown in FIG. 17 and shows that the desired delay in acarbose release is obtained.

Example 1L, Orlistat 60 mg/Acarbose 20 mg

G1 is extruded and spheronized with hard fat.

| Ingredient | % w/w |
|---|---|
| DR$_{DC}$-PR$_{GASTRIC}$ Granules (G1) | |
| Acarbose | 2.0 |
| Wax, water-soluble | 1-10 |
| Hard fat | 1-10 |
| Filler | 0-5 |
| Sub-total: | 5-20 |
| DR$_{EC}$-RR$_{PROX\,SI}$ Granules (G2) | |
| Orlistat | 7.2 |
| Acarbose | 1.4 |
| Film-coating polymer | 2-6 |
| Coating sphere, filler | 10-30 |
| Surface active agent | 0-10 |
| Enteric coating film based on methacrylic acid copolymer | 20-40 |
| Sub-total: | 45-85 |
| DR$_{DC}$-PR$_{GASTRIC}$ Granules (G3) | |
| Orlistat | 2.8 |
| Surface active agent | 0-2 |
| Filler | 1-5 |
| Sub-total: | 3-10 |

| Ingredient | % w/w |
|---|---|
| Extragranular ingredients | |
| Filler | 0-50 |
| Glidant | 0-2 |
| Lubricant | 0-2 |
| Total: | 100 |

Example 1M, Orlistat 60 mg/Acarbose 20 mg

G1 is extruded and spheronized with hard fat.

| Ingredient | mg/tablet | % w/w |
|---|---|---|
| $DR_{DC}$-$PR_{GASTRIC}$ Granules (G1) | | |
| Acarbose | 11.7 | 2.0 |
| Glyceryl monostearate | 18.7 | 3.1 |
| Hydrogenated vegetable oil type II, Dynasan P60 | 14.6 | 2.4 |
| Mannitol | 13.5 | 2.2 |
| Sub-total: | 58.5 | 9.8 |
| $DR_{EC}$-$RR_{PROX\,SI}$ Granules (G2) | | |
| Orlistat | 43.3 | 7.2 |
| Acarbose | 8.3 | 1.4 |
| Hydroxypropyl cellulose, Klucel | 15.4 | 2.6 |
| Microcrystalline cellulose, Celphere CP 203 | 109 | 18.2 |
| Polysorbate 80, Tween 80 | 5.6 | 0.9 |
| Opadry (HPMC low viscosity grade, 6 cps, triacetin, and talc) | 9.4 | 1.6 |
| Eudragit L 100-55 (methacrylic acid - ethyl acrylate copolymer (1:1) Type A) | 99.4 | 16.6 |
| Triethyl citrate | 10.1 | 1.7 |
| Talc | 74.6 | 12.4 |
| Sub-total: | 375 | 62.5 |
| $DR_{DC}$-$PR_{GASTRIC}$ Granules (G3) | | |
| Orlistat | 16.7 | 2.8 |
| Polysorbate 80, Tween 80 | 5.8 | 1.0 |
| Microcrystalline cellulose | 7.5 | 1.3 |
| Sub-total: | 30.0 | 5.0 |
| Extragranular ingredients | | |
| Isomalt | 70.0 | 11.7 |
| Microcrystalline cellulose | 60.5 | 10.1 |
| Silica, colloidal anhydrous | 3.0 | 0.5 |
| Magnesium stearate | 3.0 | 0.5 |
| Total: | 600 | 100 |

FIG. 16 shows the dissolution profile of G3.

Example 1N, Orlistat 60 mg/Acarbose 20 mg

G1 is extruded and spheronized with hard fat.
G2 is extruded and spheronized pellet cores.

| Ingredient | mg/tablet | % w/w |
|---|---|---|
| $DR_{DC}$-$PR_{GASTRIC}$ Granules (G1) | | |
| Acarbose | 11.7 | 2.0 |
| Glyceryl monostearate | 18.7 | 3.1 |
| Hydrogenated vegetable oil type II, Dynasan P60 | 14.6 | 2.4 |
| Mannitol | 13.5 | 2.2 |
| Sub-total: | 58.5 | 9.8 |
| $DR_{EC}$-$RR_{PROX\,SI}$ Granules (G2) | | |
| Orlistat | 43.3 | 10.8 |
| Acarbose | 8.3 | 2.1 |
| Microcrystalline cellulose | 65.8 | 16.5 |
| Polysorbate 80, Tween 80 | 13.4 | 3.4 |
| Mannitol | 9.8 | 2.5 |
| Croscarmellose sodium | 5.9 | 1.5 |
| Sodium stearyl fumarate, Pruv | 2.1 | 0.5 |
| Opadry (HPMC low viscosity grade, 6 cps, triacetin, and talc) | 4.5 | 1.1 |
| Acryl-EZE (methacrylic acid copolymer Type C, sodium lauryl sulphate, macrogol, talc, sodium bicarbonate and colloidal silica, anhydrous) | 59.5 | 14.9 |
| Sub-total: | 212 | 53.0 |
| $DR_{DC}$-$PR_{GASTRIC}$ Granules (G3) | | |
| Orlistat | 16.7 | 4.2 |
| Polysorbate 80, Tween 80 | 5.8 | 1.5 |
| Microcrystalline cellulose | 7.5 | 1.9 |
| Sub-total: | 30.0 | 7.5 |
| Extragranular ingredients | | |
| Isomalt | 50.0 | 12.5 |
| Microcrystalline cellulose | 45.0 | 11.3 |
| Silica, colloidal anhydrous | 2.0 | 0.5 |
| Magnesium stearate | 2.0 | 0.5 |
| Total: | 400 | 100 |

The multiple-unit tablets of Example 1E-N are prepared as follows:

As the formulation consists of three different active granules they can be denoted G1-G3; i.e. the $DR_{DC}$-$PR_{GASTRIC}$ Granules can be denoted G1 (Granule 1), the $DR_{EC}$-$RR_{PROX\,SI}$ Granules can be denoted G2 (Granule 2) and the $DR_{DC}$-$PR_{GASTRIC}$ Granules can be denoted G3 (Granule 3).

The coated G1 granules are manufactured in a fluidized bed coater in bottom spray (Wurster) configuration (Example 1E-H), such as a bench size Glatt GPCG-1 or similar. Microcrystalline cellulose or sugar alcohol based spheres with an initial size of approximately 250 μm are used as cores in the coating. The coating is performed in two steps: step 1 include an aqueous coating solution with a mix of acarbose and a binder/coating film, such as HPMC, and in step 2 is consisted of a release-delaying coating layer with a mix of ethylcellulose and HPMC, i.e. an additional coating to the acarbose-containing coated cores. The final granules are approximately 400 μm in size.

The spheronized G1 granules are manufactured either by a standard wet-granulation (Example 1I-K) or by a melt-granulation process (Example 1 L-N) in a standard high-shear mixer, such as a Diosna P1/6 with a 0.5 L granulation bowl, with a following extrusion and spheronization in standard equipment, such as NICA model E140 and NICA S320-450. The adjusted combination of poorly soluble hard fat with waxy glyceryl monostearate, co-melted at 80° C., generates enough time to have a soft material during spheronization before solidification. The wet granulated G1 spheres with ethylcellulose/HPMC are dried in standard heating cabinets at 40° C. to be finalized. The final granules are approximately 1 mm in size.

The enteric coated G2 granules are manufactured either by using spheronized pellet cores with APIs distributed throughout the core or by using core spheres of microcrystalline cellulose or sugar alcohol with an initial size of approximately 250 μm with the active substances coated in a layer on the surface. The spheronized pellet cores are produced by using a standard wet-granulation procedure (Example 1H, 1K and 1N) in a standard high-shear mixer, such as a Diosna P1/6 with a 0.5 L granulation bowl, with a following extrusion and spheronization in standard equipment, such as NICA model E140 and NICA S320-450. The enteric coating is performed in a fluidized bed coater in bottom spray (Wurster) configuration, such as a bench size Glatt GPCG-1 or similar. The coating suspensions are prepared by using an overhead stirrer with wing impeller and added by a standard peristaltic pump. When using Eudragit L30 D-55 (methacrylic acid—ethyl acetate copolymer (1:1) dispersion 30 percent) the dispersion is in ethanol 99.5% and when using Acryl-EZE (methacrylic acid copolymer type C, sodium lauryl sulphate, macrogol, talc, sodium bicarbonate and colloidal silica, anhydrous) the dispersion is in water. For the coated cores and an addition of polysorbate 80, an additional talc amount is used in the coating-layer to avoid agglomeration. The final granules with microcrystalline spheres are approximately 500 μm in size and with extruded pellet cores approximately 1 mm.

The wet-granulated G3 granules are prepared by wet granulation. It is performed in a high-shear mixer such as a Diosna P1/6 with a 0.5 L granulation bowl with side-chopper. The impeller speed is 690 rpm in the 0.5 L bowl, i.e. corresponding to a tip speed of 4.0 m/s and the chopper speed is 1200 rpm. The water/ethanol granulation liquid is mixed together with polysorbate 80 (Tween™ 80) for 2 minutes in a 100 mL glass beaker with magnetic stirrer at room temperature. The liquid solution is then drawn into a 50 mL plastic syringe and a cannula is attached. The granulation procedure is performed in three steps with short breaks of approximately 30 seconds for visual inspection between every step:

1. 30 seconds—Dry powder mixing
2. 30 seconds-$1^{st}$ liquid addition; 17 mL (~½) addition with an even pressure via syringe and cannula
3. 30 seconds-$2^{nd}$ liquid addition—17 mL addition (last ~½) as above In a fourth step of 30 seconds "Massing time" (wet mixing) is used for high liquid content batches. For low liquid content batches, no additional massing is needed. Directly after the massing, the wet granules are gently forced through a 1.0 mm sieve (standard sieve for sieve analysis, 200 mm diameter, 1 mm mesh size, Retsch GmbH, Germany) by help of a stainless steel spoon and distributed evenly on a drying tray. The tray is put in a heating cabinet at 35° C.—i.e. below the melting point of orlistat—to dry for at least 12 hours to finalize the G3. The final granules are approximately 500 μm in size.

When the granules are dry and solidified; add isomalt, mannitol, xylitol and the congealed granules in a tumbling mixer. Mix for 10-30 minutes, depending on mixer. Sieve magnesium stearate through a 100-250-μm sieve, add to the tumbling mixer and mix for additional approximately 2 minutes, depending on mixer. Transfer the final blend to a rotary tablet press and compress tablets with a total weight of either 400 mg, 600 mg or 800 mg.

Especially the compositions of Examples 1E, 1F, 1G have excellent properties. All other examples have good/acceptable properties.

Example 2. Bi-Layer Multiple-Unit Tablet

Example 2A, Orlistat 90 mg/Acarbose 30 mg

| Ingredient | % w/w |
|---|---|
| $DR_{DC}$-$PR_{GASTRIC}$ Granules (G1) | |
| Acarbose | 0.2-1 |
| Filler | 0-20 |
| Disintegrant | 0-5 |
| Binder | 0-5 |
| Prolonged release polymer | 0-10 |
| Coating polymer, 30-60 min delay | 1-10 |
| Sub-total: | 1-51 |
| $DR_{EC}$-$RR_{PROX\,SI}$ Granules (G2) | |
| Orlistat | 4-12 |
| Acarbose | 2-4 |
| Filler | 0-10 |
| Binder | 0-5 |
| Disintegrant | 0-10 |
| Solubilizer | 0-5 |
| Sub-coating polymer | 0-5 |
| Enteric coating polymer | 1-11 |
| Sub-total: | 7-52 |
| $DR_{DC}$-$PR_{GASTRIC}$ Granules (G3) | |
| Orlistat | 3-6 |
| Prolonged release polymer | 10-40 |
| Coating polymer, 30-60 min delay | 0-10 |
| Sub-total: | 13-56 |
| Extragranular ingredients, $DR_{DC}$-PR layer | |
| Filler | 0-50 |
| Prolonged release polymer | 0-10 |
| Glidant | 0-2 |
| Lubricant | 0-2 |
| Extragranular ingredients, $DR_{EC}$-$RR_{PROX\,SI}$ layer | |
| Filler | 0-50 |
| Disintegrant | 0-2 |
| Glidant | 0-2 |
| Lubricant | 0-2 |
| Total: | 100 |

Example 2B, Orlistat 90 mg/Acarbose 30 mg

| Ingredient | mg/tablet | % w/w |
|---|---|---|
| $DR_{DC}$-$PR_{GASTRIC}$ Granules (G1) | | |
| Acarbose | 5 | 0.6 |
| Filler | 47 | 5.9 |
| Disintegrant | 5 | 0.6 |
| Binder | 3 | 0.4 |
| Prolonged release polymer | 30 | 3.8 |
| Coating polymer, 30-60 min delay | 10 | 1.3 |
| Sub-total: | 100 | 13 |
| $DR_{EC}$-$RR_{PROX\,SI}$ Granules (G2) | | |
| Orlistat | 65 | 8.1 |
| Acarbose | 25 | 3.1 |
| Filler | 30 | 3.8 |
| Binder | 25 | 3.1 |
| Disintegrant | 30 | 3.8 |
| Solubilizer | 5 | 0.6 |

-continued

| Ingredient | mg/tablet | % w/w |
|---|---|---|
| Sub-coating polymer | 12 | 1.5 |
| Enteric coating polymer | 48 | 6.0 |
| Sub-total: $DR_{DC}$-$PR_{GASTRIC}$ Granules (G3) | 230 | 29 |
| Orlistat | 25 | 3.1 |
| Prolonged release polymer | 215 | 27 |
| Coating polymer, 30-60 min delay | 10 | 1.3 |
| Sub-total: Extragranular ingredients, $DR_{DC}$-PR layer | 250 | 31 |
| Filler | 80 | 10 |
| Prolonged release polymer | 16 | 2.0 |
| Glidant | 2 | 0.3 |
| Lubricant | 2 | 0.3 |
| Extragranular ingredients, $DR_{EC}$-$RR_{PROX\,SI}$ layer | | |
| Filler | 112 | 14 |
| Disintegrant | 6 | 0.7 |
| Glidant | 2 | 0.3 |
| Lubricant | 2 | 0.3 |
| Total: | 800 | 100 |

Example 2C, Orlistat 90 mg/Acarbose 30 mg

| Ingredient | mg/tablet | % w/w |
|---|---|---|
| $DR_{DC}$-$PR_{GASTRIC}$ Granules (G1) | | |
| Acarbose | 5 | 6.3 |
| Mannitol | 47 | 5.9 |
| Croscarmellose sodium | 5 | 0.6 |
| Polyvinylpyrrolidone | 3 | 0.4 |
| Ethylcellulose | 30 | 3.8 |
| Eudragit L30 D-55 (methacrylic acid-ethyl acetate copolymer (1:1) dispersion 30 percent) | 10 | 1.3 |
| Sub-total: $DR_{EC}$-$RR_{PROX\,SI}$ Granules (G2) | 100 | 13 |
| Orlistat | 65 | 8.1 |
| Acarbose | 25 | 3.1 |
| Microcrystalline cellulose | 30 | 3.8 |
| Polyvinylpyrrolidone, Povidone | 25 | 3.1 |
| Sodium starch glycolate, Primojel | 30 | 3.8 |
| Sodium lauryl sulphate, SDS | 5 | 0.6 |
| Opadry II Clear (macrogol 3350, polysorbate 80, polyvinyl alcohol and talc) | 12 | 1.5 |
| Acryl-EZE Clear (methacrylic acid copolymer type C, sodium lauryl sulphate, macrogol, talc, sodium bicarbonate and colloidal silica, anhydrous) | 48 | 6.0 |
| Sub-total: $DR_{DC}$-$PR_{GASTRIC}$ Granules (G3) | 230 | 29 |
| Orlistat | 25 | 3.1 |
| Hypromellose, HPMC K100 | 215 | 27 |
| Eudragit L30 D-55 (methacrylic acid-ethyl acetate copolymer (1:1) dispersion 30 percent) | 10 | 1.3 |
| Sub-total: Extragranular ingredients, $DR_{DC}$-PR layer | 250 | 31 |
| Isomalt | 80 | 10 |
| Hydroxyethylcellulose | 16 | 2.0 |
| Silica, colloidal anhydrous | 2 | 0.3 |
| Magnesium stearate | 2 | 0.3 |
| Extragranular ingredients, $DR_{EC}$-$RR_{PROX\,SI}$ layer | | |
| Isomalt | 112 | 14 |
| Sodium croscarmellose | 6 | 0.7 |
| Silica, colloidal anhydrous | 2 | 0.3 |
| Magnesium stearate | 2 | 0.3 |
| Total: | 800 | 100 |

The bi-layer multiple-unit tablets of Example 2A-C are prepared as follows:

The powder blends including granular (G1, G2, G3) and extragranular ingredients are prepared as described in Example 1A-D above but in two separate blenders—one for each layer. Transfer the blends to a rotary tablet machine with two filling stations adjusted for bi-layer tabletting in two steps; PR/D-PR to 450 mg and then additionally EC-BR 350 mg with a total tablet weight of 800 mg.

Example 2D, Orlistat 60 mg/Acarbose 20 mg

| Ingredient | % w/w |
|---|---|
| $DR_{DC}$-$PR_{GASTRIC}$ Granules (G1) | |
| Acarbose | 2.0 |
| Film-coating polymer, water-soluble | 1-10 |
| Delayed release coating polymer, poorly water-soluble | 1-5 |
| Coating sphere, filler | 1-5 |
| Sub-total: | 5-20 |
| $DR_{DC}$-$PR_{GASTRIC}$ Granules (G3) | |
| Orlistat | 2.8 |
| Surface active agent | 0-2 |
| Filler | 1-5 |
| Sub-total: | 3-10 |
| Extragranular ingredients, $DR_{DC}$-PR layer (G1, G3-layer) | |
| Filler | 0-50 |
| Prolonged release polymer | 0-10 |
| Glidant | 0-2 |
| Lubricant | 0-2 |
| $DR_{EC}$-$RR_{PROX\,SI}$ Granules (G2) | |
| Orlistat | 7.2 |
| Acarbose | 1.4 |
| Film-coating polymer | 2-6 |
| Coating sphere, filler | 10-30 |
| Surface active agent | 0-10 |
| Enteric coating film based on methacrylic acid copolymer | 20-40 |
| Sub-total: | 45-85 |
| Extragranular ingredients, $DR_{EC}$-$RR_{PROX\,SI}$ layer (G2-layer) | |
| Filler | 0-50 |
| Disintegrant | 0-2 |
| Glidant | 0-2 |
| Lubricant | 0-2 |
| Total: | 100 |

Example 2E, Orlistat 60 mg/Acarbose 20 mg

| Ingredient | mg/tablet | % w/w |
|---|---|---|
| $DR_{DC}\text{-}PR_{GASTRIC}$ Granules (G1) | | |
| Acarbose | 11.7 | 2.0 |
| Hydroxypropyl methylcellulose | 1.6 | 0.3 |
| Ethylcellulose, Surelease | 6.8 | 1.1 |
| Microcrystalline cellulose, Celphere CP 203 | 9.9 | 1.6 |
| Sub-total: | 30.0 | 5.0 |
| $DR_{DC}\text{-}PR_{GASTRIC}$ Granules (G3) | | |
| Orlistat | 16.7 | 2.8 |
| Polysorbate 80, Tween 80 | 5.8 | 1.0 |
| Microcrystalline cellulose | 7.5 | 1.3 |
| Sub-total: | 30.0 | 5.0 |
| Extragranular ingredients, $DR_{DC}$-PR layer (G1, G3-layer) | | |
| Isomalt | 60.0 | 10 |
| Hydroxyethylcellulose | 12.0 | 2.0 |
| Silica, colloidal anhydrous | 1.3 | 0.3 |
| Magnesium stearate | 1.3 | 0.3 |
| $DR_{EC}\text{-}RR_{PROX\,SI}$ Granules (G2) | | |
| Orlistat | 43.3 | 7.2 |
| Acarbose | 8.3 | 1.4 |
| Hydroxypropyl cellulose, Klucel | 15.4 | 2.6 |
| Microcrystalline cellulose, Celphere CP 203 | 109 | 18.2 |
| Polysorbate 80, Tween 80 | 5.6 | 0.9 |
| Opadry (HPMC low viscosity grade, 6 cps, triacetin, and talc) | 9.4 | 1.6 |
| Eudragit L 100-55 (methacrylic acid-ethyl acrylate copolymer (1:1) Type A) | 99.4 | 16.6 |
| Triethyl citrate | 10.1 | 1.7 |
| Talc | 74.6 | 12.4 |
| Sub-total: | 375 | 62.5 |
| Extragranular ingredients, $DR_{EC}\text{-}RR_{PROX\,SI}$ layer (G2-layer) | | |
| Isomalt | 83.3 | 13.9 |
| Sodium croscarmellose | 4.5 | 0.7 |
| Silica, colloidal anhydrous | 1.3 | 0.3 |
| Magnesium stearate | 1.3 | 0.3 |
| Total: | 600 | 100 |

Example 2F, Orlistat 90 mg/Acarbose 30 mg

| Ingredient | mg/tablet | % w/w |
|---|---|---|
| $DR_{DC}\text{-}PR_{GASTRIC}$ Granules (G1) | | |
| Acarbose | 18.0 | 2.3 |
| Hydroxypropyl methylcellulose | 2.4 | 0.3 |
| Ethylcellulose, Surelease | 10.2 | 1.3 |
| Microcrystalline cellulose, Celphere CP 203 | 14.9 | 1.9 |
| Sub-total: | 45.5 | 5.7 |
| $DR_{DC}\text{-}PR_{GASTRIC}$ Granules (G3) | | |
| Orlistat | 25.0 | 3.1 |
| Polysorbate 80, Tween 80 | 1.4 | 0.2 |
| Microcrystalline cellulose | 9.3 | 1.2 |
| Sub-total: | 35.7 | 4.5 |
| Extragranular ingredients, $DR_{DC}$-PR layer (G1, G3-layer) | | |
| Isomalt | 50.0 | 6.3 |
| Hydroxyethylcellulose | 16.0 | 2.0 |
| Silica, colloidal anhydrous | 2.4 | 0.3 |
| Magnesium stearate | 2.4 | 0.3 |
| $DR_{EC}\text{-}RR_{PROX\,SI}$ Granules (G2) | | |
| Orlistat | 65.0 | 8.1 |
| Acarbose | 12.0 | 1.5 |
| Hydroxypropyl cellulose, Klucel | 23.0 | 2.9 |
| Microcrystalline cellulose, Celphere CP 203 | 163 | 20.4 |
| Polysorbate 80, Tween 80 | 8.3 | 1.0 |
| Eudragit L 100-55 (methacrylic acid-ethyl acrylate copolymer (1:1) Type A) | 199 | 24.9 |
| Triethyl citrate | 20.1 | 2.5 |
| Talc | 99.9 | 12.5 |
| Sub-total: | 591 | 73.9 |
| Extragranular ingredients, $DR_{EC}\text{-}RR_{PROX\,SI}$ layer (G2-layer) | | |
| Isomalt | 48.0 | 6.0 |
| Sodium croscarmellose | 4.2 | 0.7 |
| Silica, colloidal anhydrous | 2.4 | 0.3 |
| Magnesium stearate | 2.4 | 0.3 |
| Total: | 800 | 100 |

Example 2G, Orlistat 60 mg/Acarbose 20 mg

As Example 2E, but G2 is extruded and spheronized pellet cores.

| Ingredient | mg/tablet | % w/w |
|---|---|---|
| $DR_{DC}\text{-}PR_{GASTRIC}$ Granules (G1) | | |
| Acarbose | 11.7 | 2.9 |
| Hydroxypropyl methylcellulose | 1.6 | 0.4 |
| Ethylcellulose, Surelease | 6.8 | 1.7 |
| Microcrystalline cellulose, Celphere CP 203 | 9.9 | 2.5 |
| Sub-total: | 30.0 | 7.5 |
| $DR_{DC}\text{-}PR_{GASTRIC}$ Granules (G3) | | |
| Orlistat | 16.7 | 4.2 |
| Polysorbate 80, Tween 80 | 5.8 | 1.5 |
| Microcrystalline cellulose | 7.5 | 1.9 |
| Sub-total: | 30.0 | 7.5 |
| Extragranular ingredients, $DR_{DC}$-PR layer (G1, G3-layer) | | |
| Isomalt | 57.0 | 14.3 |
| Hydroxyethylcellulose | 8.0 | 2.0 |
| Silica, colloidal anhydrous | 1.2 | 0.3 |
| Magnesium stearate | 1.2 | 0.3 |
| $DR_{EC}\text{-}RR_{PROX\,SI}$ Granules (G2) | | |
| Orlistat | 43.3 | 10.8 |
| Acarbose | 8.3 | 2.1 |
| Microcrystalline cellulose | 65.8 | 16.5 |
| Polysorbate 80, Tween 80 | 13.4 | 3.4 |
| Mannitol | 9.8 | 2.5 |
| Croscarmellose sodium | 5.9 | 1.5 |
| Sodium stearyl fumarate, Pruv | 2.1 | 0.5 |
| Opadry (HPMC low viscosity grade, 6 cps, triacetin, and talc) | 4.5 | 1.1 |
| Acryl-EZE (methacrylic acid copolymer Type C, sodium lauryl sulphate, macrogol, talc, sodium bicarbonate and colloidal silica, anhydrous) | 59.5 | 14.9 |
| Sub-total: | 212 | 53.0 |

-continued

| Ingredient | mg/tablet | % w/w |
|---|---|---|
| Extragranular ingredients, $DR_{EC}$-$RR_{PROX\ SI}$ layer (G2-layer) | | |
| Isomalt | 55.4 | 13.9 |
| Sodium croscarmellose | 2.8 | 0.7 |
| Silica, colloidal anhydrous | 1.2 | 0.3 |
| Magnesium stearate | 1.2 | 0.3 |
| Total: | 400 | 100 |

Example 2H, Orlistat 60 mg/Acarbose 20 mg

G1 is extruded and spheronized with ethylcellulose/hydroxypropylmethylcellulose.

| Ingredient | % w/w |
|---|---|
| $DR_{DC}$-$PR_{GASTRIC}$ Granules (G1) | |
| Acarbose | 2.0 |
| Cellulose-based polymer, water-soluble | 1-10 |
| Delayed release polymer, poorly water-soluble | 1-10 |
| Lubricant | 0-5 |
| Sub-total: | 5-20 |
| $DR_{DC}$-$PR_{GASTRIC}$ Granules (G3) | |
| Orlistat | 2.8 |
| Surface active agent | 0-2 |
| Filler | 1-5 |
| Sub-total: | 3-10 |
| Extragranular ingredients, $DR_{DC}$-PR layer (G1, G3-layer) | |
| Filler | 0-50 |
| Prolonged release polymer | 0-10 |
| Glidant | 0-2 |
| Lubricant | 0-2 |
| $DR_{EC}$-$RR_{PROX\ SI}$ Granules (G2) | |
| Orlistat | 7.2 |
| Acarbose | 1.4 |
| Film-coating polymer | 2-6 |
| Coating sphere, filler | 10-30 |
| Surface active agent | 0-10 |
| Enteric coating film based on methacrylic acid copolymer | 20-40 |
| Sub-total: | 45-85 |
| Extragranular ingredients, $DR_{EC}$-$RR_{PROX\ SI}$ layer (G2-layer) | |
| Filler | 0-50 |
| Disintegrant | 0-2 |
| Glidant | 0-2 |
| Lubricant | 0-2 |
| Total: | 100 |

Example 2I, Orlistat 60 mg/Acarbose 20 mg

G1 is extruded and spheronized with ethylcellulose/hydroxypropylmethylcellulose.

| Ingredient | mg/tablet | % w/w |
|---|---|---|
| $DR_{DC}$-$PR_{GASTRIC}$ Granules (G1) | | |
| Acarbose | 11.7 | 2.0 |
| Hydroxypropyl methylcellulose | 22.8 | 3.8 |
| Ethylcellulose, Ethocel 10 FP | 23.4 | 3.9 |
| Sodium stearyl fumarate, Pruv | 0.6 | 0.1 |
| Sub-total: | 58.5 | 9.8 |
| $DR_{DC}$-$PR_{GASTRIC}$ Granules (G3) | | |
| Orlistat | 16.7 | 2.8 |
| Polysorbate 80, Tween 80 | 5.8 | 1.0 |
| Microcrystalline cellulose | 7.5 | 1.3 |
| Sub-total: | 30.0 | 5.0 |
| Extragranular ingredients, $DR_{DC}$-PR layer (G1, G3-layer) | | |
| Isomalt | 60.0 | 10 |
| Hydroxyethylcellulose | 12.0 | 2.0 |
| Silica, colloidal anhydrous | 1.3 | 0.3 |
| Magnesium stearate | 1.3 | 0.3 |
| $DR_{EC}$-$RR_{PROX\ SI}$ Granules (G2) | | |
| Orlistat | 43.3 | 7.2 |
| Acarbose | 8.3 | 1.4 |
| Hydroxypropyl cellulose, Klucel | 15.4 | 2.6 |
| Microcrystalline cellulose, Celphere CP 203 | 109 | 18.2 |
| Polysorbate 80, Tween 80 | 5.6 | 0.9 |
| Opadry (HPMC low viscosity grade, 6 cps, triacetin, and talc) | 9.4 | 1.6 |
| Eudragit L 100-55 (methacrylic acid-ethyl acrylate copolymer (1:1) Type A) | 99.4 | 16.6 |
| Triethyl citrate | 10.1 | 1.7 |
| Talc | 74.6 | 12.4 |
| Sub-total: | 375 | 62.5 |
| Extragranular ingredients, $DR_{EC}$-$RR_{PROX\ SI}$ layer (G2-layer) | | |
| Isomalt | 54.8 | 9.1 |
| Sodium croscarmellose | 4.5 | 0.7 |
| Silica, colloidal anhydrous | 1.3 | 0.3 |
| Magnesium stearate | 1.3 | 0.3 |
| Total: | 600 | 100 |

Example 2J, Orlistat 60 mg/Acarbose 20 mg

G1 is extruded and spheronized with ethylcellulose/hydroxypropylmethylcellulose. G2 extruded and spheronized pellet cores.

| Ingredient | mg/tablet | % w/w |
|---|---|---|
| $DR_{DC}$-$PR_{GASTRIC}$ Granules (G1) | | |
| Acarbose | 11.7 | 2.9 |
| Hydroxypropyl methylcellulose | 22.8 | 5.7 |
| Ethylcellulose, Ethocel 10 FP | 23.4 | 5.9 |
| Sodium stearyl fumarate, Pruv | 0.6 | 0.2 |
| Sub-total: | 58.5 | 14.6 |
| $DR_{DC}$-$PR_{GASTRIC}$ Granules (G3) | | |
| Orlistat | 16.7 | 4.2 |
| Polysorbate 80, Tween 80 | 5.8 | 1.5 |
| Microcrystalline cellulose | 7.5 | 1.9 |
| Sub-total: | 30.0 | 7.5 |
| Extragranular ingredients, $DR_{DC}$-PR layer (G1, G3-layer) | | |
| Isomalt | 43.9 | 11.0 |
| Hydroxyethylcellulose | 8.0 | 2.0 |
| Silica, colloidal anhydrous | 1.2 | 0.3 |
| Magnesium stearate | 1.2 | 0.3 |

-continued

| Ingredient | mg/tablet | % w/w |
|---|---|---|
| $DR_{EC}$-$RR_{PROX\,SI}$ Granules (G2) | | |
| Orlistat | 43.3 | 10.8 |
| Acarbose | 8.3 | 2.1 |
| Microcrystalline cellulose | 65.8 | 16.5 |
| Polysorbate 80, Tween 80 | 13.4 | 3.4 |
| Mannitol | 9.8 | 2.5 |
| Croscarmellose sodium | 5.9 | 1.5 |
| Sodium stearyl fumarate, Pruv | 2.1 | 0.5 |
| Opadry (HPMC low viscosity grade, 6 cps, triacetin, and talc) | 4.5 | 1.1 |
| Acryl-EZE (methacrylic acid copolymer Type C, sodium lauryl sulphate, macrogol, talc, sodium bicarbonate and colloidal silica, anhydrous) | 59.5 | 14.9 |
| Sub-total: | 212 | 53.0 |
| Extragranular ingredients, $DR_{EC}$-$RR_{PROX\,SI}$ layer (G2-layer) | | |
| Isomalt | 40.0 | 10.0 |
| Sodium croscarmellose | 2.8 | 0.7 |
| Silica, colloidal anhydrous | 1.2 | 0.3 |
| Magnesium stearate | 1.2 | 0.3 |
| Total: | 400 | 100 |

Example 2K, Orlistat 60 mg/Acarbose 20 mg

G1 extruded and spheronized with hard fat.

| Ingredient | % w/w |
|---|---|
| $DR_{DC}$-$PR_{GASTRIC}$ Granules (G1) | |
| Acarbose | 2.0 |
| Wax, water-soluble | 1-10 |
| Hard fat | 1-10 |
| Filler | 0-5 |
| Sub-total: | 5-20 |
| $DR_{DC}$-$PR_{GASTRIC}$ Granules (G3) | |
| Orlistat | 2.8 |
| Surface active agent | 0-2 |
| Filler | 1-5 |
| Sub-total: | 3-10 |
| Extragranular ingredients, $DR_{DC}$-PR layer (G1, G3-layer) | |
| Filler | 0-50 |
| Prolonged release polymer | 0-10 |
| Glidant | 0-2 |
| Lubricant | 0-2 |
| $DR_{EC}$-$RR_{PROX\,SI}$ Granules (G2) | |
| Orlistat | 7.2 |
| Acarbose | 1.4 |
| Film-coating polymer | 2-6 |
| Coating sphere, filler | 10-30 |
| Surface active agent | 0-10 |
| Enteric coating film based on methacrylic acid copolymer | 20-40 |
| Sub-total: | 45-85 |
| Extragranular ingredients, $DR_{EC}$-$RR_{PROX\,SI}$ layer (G2-layer) | |
| Filler | 0-50 |
| Disintegrant | 0-2 |
| Glidant | 0-2 |
| Lubricant | 0-2 |
| Total: | 100 |

Example 2L, Orlistat 60 mg/Acarbose 20 mg

G1 extruded and spheronized with hard fat.

| Ingredient | mg/tablet | % w/w |
|---|---|---|
| $DR_{DC}$-$PR_{GASTRIC}$ Granules (G1) | | |
| Acarbose | 11.7 | 2.0 |
| Glyceryl monostearate | 18.7 | 3.1 |
| Hydrogenated vegetable oil type II, Dynasan P60 | 14.6 | 2.4 |
| Mannitol | 13.5 | 2.2 |
| Sub-total: | 58.5 | 9.8 |
| $DR_{DC}$-$PR_{GASTRIC}$ Granules (G3) | | |
| Orlistat | 16.7 | 2.8 |
| Polysorbate 80, Tween 80 | 5.8 | 1.0 |
| Microcrystalline cellulose | 7.5 | 1.3 |
| Sub-total: | 30.0 | 5.0 |
| Extragranular ingredients, $DR_{DC}$-PR layer (G1,G3-layer) | | |
| Isomalt | 60.0 | 10.0 |
| Hydroxyethylcellulose | 12.0 | 2.0 |
| Silica, colloidal anhydrous | 1.3 | 0.3 |
| Magnesium stearate | 1.3 | 0.3 |
| $DR_{EC}$-$RR_{PROX\,SI}$ Granules (G2) | | |
| Orlistat | 43.3 | 7.2 |
| Acarbose | 8.3 | 1.4 |
| Hydroxypropyl cellulose, Klucel | 15.4 | 2.6 |
| Microcrystalline cellulose, Celphere CP 203 | 109 | 18.2 |
| Polysorbate 80, Tween 80 | 5.6 | 0.9 |
| Opadry (HPMC low viscosity grade, 6 cps, triacetin, and talc) | 9.4 | 1.6 |
| Eudragit L 100-55 (methacrylic acid-ethyl acrylate co-polymer (1:1) Type A) | 99.4 | 16.6 |
| Triethyl citrate | 10.1 | 1.7 |
| Talc | 74.6 | 12.4 |
| Sub-total: | 375 | 62.5 |
| Extragranular ingredients, $DR_{EC}$-$RR_{PROX\,SI}$ layer (G2-layer) | | |
| Isomalt | 54.8 | 9.1 |
| Sodium croscarmellose | 4.5 | 0.7 |
| Silica, colloidal anhydrous | 1.3 | 0.3 |
| Magnesium stearate | 1.3 | 0.3 |
| Total: | 600 | 100 |

Example 2M, Orlistat 60 mg/Acarbose 20 mg

G1 extruded and spheronized with hard fat. G2 extruded and spheronized pellet cores.

| Ingredient | mg/tablet | % w/w |
|---|---|---|
| $DR_{DC}$-$PR_{GASTRIC}$ Granules (G1) | | |
| Acarbose | 11.7 | 2.9 |
| Glyceryl monostearate | 18.7 | 4.7 |

| Ingredient | mg/tablet | % w/w |
|---|---|---|
| Hydrogenated vegetable oil type II, Dynasan P60 | 14.6 | 3.7 |
| Mannitol | 13.5 | 3.4 |
| Sub-total: | 58.5 | 14.6 |
| $DR_{DC}$-$PR_{GASTRIC}$ Granules (G3) | | |
| Orlistat | 16.7 | 4.2 |
| Polysorbate 80, Tween 80 | 5.8 | 1.5 |
| Microcrystalline cellulose | 7.5 | 1.9 |
| Sub-total: | 30.0 | 7.5 |
| Extragranular ingredients, $DR_{DC}$-PR layer (G1,G3-layer) | | |
| Isomalt | 43.9 | 11.0 |
| Hydroxyethylcellulose | 8.0 | 2.0 |
| Silica, colloidal anhydrous | 1.2 | 0.3 |
| Magnesium stearate | 1.2 | 0.3 |
| $DR_{EC}$-$RR_{PROX\,SI}$ Granules (G2) | | |
| Orlistat | 43.3 | 10.8 |
| Acarbose | 8.3 | 2.1 |
| Microcrystalline cellulose | 65.8 | 16.5 |
| Polysorbate 80, Tween 80 | 13.4 | 3.4 |
| Mannitol | 9.8 | 2.5 |
| Croscarmellose sodium | 5.9 | 1.5 |
| Sodium stearyl fumarate, Pruv | 2.1 | 0.5 |
| Opadry (HPMC low viscosity grade, 6 cps, triacetin, and talc) | 4.5 | 1.1 |
| Acryl-EZE (methacrylic acid copolymer Type C, sodium lauryl sulphate, macrogol, talc, sodium bicarbonate and colloidal silica, anhydrous) | 59.5 | 14.9 |
| Sub-total: | 212 | 53.0 |
| Extragranular ingredients, $DR_{EC}$-$RR_{PROX\,SI}$ layer (G2-layer) | | |
| Isomalt | 40.0 | 10.0 |
| Sodium croscarmellose | 2.8 | 0.7 |
| Silica, colloidal anhydrous | 1.2 | 0.3 |
| Magnesium stearate | 1.2 | 0.3 |
| Total: | 400 | 100 |

The bi-layer multiple-unit tablets of Example 2D-M are prepared as follows:

The powder blends including granular (G1, G2, G3) and extragranular ingredients are prepared as described in Example 1 above but in two separate blenders—one for each layer. Transfer the blends to a rotary tablet machine with two filling stations adjusted for bi-layer tabletting in two steps; first the $DR_{DC}$-PR layer (G1,G3-layer) and then additionally the $DR_{EC}$-$RR_{PROX\,SI}$ layer (G2-layer) with a total tablet weight of either 400 mg, 600 mg or 800 mg.

Especially compositions of Examples 2D-F gave excellent results. The other compositions had good/acceptable properties.

Example 3. Coated Tablet

Example 3A, Orlistat 90 mg/Acarbose 30 mg

| Ingredient | % w/w |
|---|---|
| PR Tablet core | |
| Orlistat | 1-5 |
| Acarbose | 0-3 |
| Prolonged release polymer | 0-5 |
| Filler | 0-60 |
| Disintegrant | 0-5 |
| Glidant | 0-5 |
| Lubricant | 0-5 |
| Sub-total: | 1-88 |
| Coating ingredients | |
| Seal coating polymer | 0-5 |
| Orlistat | 6-18 |
| Acarbose | 0-5 |
| Film forming polymer | 1-25 |
| Seal coating polymer | 0-5 |
| Enteric coating polymer | 1-20 |
| Seal coating polymer | 0-5 |
| Acarbose | 0-5 |
| Coating polymer, 30-60 min delay | 0-5 |
| Seal coating polymer | 0-5 |
| Total: | 100 |

Example 3B, Orlistat 90 mg/Acarbose 30 mg

| Ingredient | mg/tablet | % w/w |
|---|---|---|
| PR Tablet core | | |
| Orlistat | 20 | 3.3 |
| Acarbose | 10 | 1.7 |
| Prolonged release polymer | 5 | 0.8 |
| Filler | 236 | 39.3 |
| Disintegrant | 25 | 4.2 |
| Glidant | 2 | 0.3 |
| Lubricant | 2 | 0.3 |
| Sub-total: | 300 | 50.0 |
| Coating ingredients | | |
| Seal coating polymer | 12 | 2.0 |
| Orlistat | 70 | 11.7 |
| Acarbose | 10 | 1.7 |
| Film forming polymer | 20 | 3.3 |
| Seal coating polymer | 12 | 2.0 |
| Enteric coating polymer | 97 | 16.2 |
| Seal coating polymer | 12 | 2.0 |
| Acarbose | 10 | 1.7 |
| Coating polymer, 30-60 min delay | 50 | 8.3 |
| Seal coating polymer | 7 | 1.2 |
| Total: | 600 | 100 |

Example 3C, Orlistat 90 mg/Acarbose 30 mg

| Ingredient | mg/tablet | % w/w |
|---|---|---|
| PR Tablet core | | |
| Orlistat | 20 | 3.3 |
| Acarbose | 10 | 1.7 |
| Ethyl cellulose, Ethocel std 7FP | 5 | 0.8 |
| Microcrystalline cellulose | 150 | 25.0 |
| Lactose | 86 | 14.3 |
| Croscarmellose sodium | 25 | 4.2 |
| Silica colloidal, anhydrous | 2 | 0.3 |
| Magnesium stearate | 2 | 0.3 |
| Sub-total: | 300 | 50.0 |

-continued

| Ingredient | mg/tablet | % w/w |
|---|---|---|
| Coating ingredients | | |
| Opadry II Clear (macrogol 3350, polysorbate 80, polyvinyl alcohol and talc) - Seal coat | 12 | 2.0 |
| Orlistat | 70 | 11.7 |
| Acarbose | 10 | 1.7 |
| Opadry II Clear - Film former | 20 | 3.3 |
| Opadry II Clear - Seal coat | 12 | 2.0 |
| Acryl-EZE Clear (methacrylic acid copolymer type C, sodium lauryl sulphate, macrogol, talc, sodium bicarbonate and colloidal silica, anhydrous) - Enteric coat | 97 | 16.2 |
| Opadry II Clear - Seal coat | 12 | 2.0 |
| Acarbose - RR drug | 10 | 1.7 |
| Eudragit L30 D-55 (methacrylic acid-ethyl acetate copolymer (1:1) dispersion 30 percent) - Film former | 50 | 8.3 |
| Opadry II Clear - Top coat | 7 | 1.2 |
| Total: | 600 | 100 |

Example 3D, Orlistat 60 mg/Acarbose 20 mg

| Ingredient | mg/tablet | % w/w |
|---|---|---|
| PR Tablet core | | |
| Orlistat | 13.3 | 3.3 |
| Acarbose | 6.7 | 1.7 |
| Ethyl cellulose, Ethocel std 7FP | 3.3 | 0.8 |
| Microcrystalline cellulose | 100 | 25.0 |
| Mannitol | 57.3 | 14.3 |
| Croscarmellose sodium | 16.7 | 4.2 |
| Silica colloidal, anhydrous | 1.3 | 0.3 |
| Magnesium stearate | 1.3 | 0.3 |
| Sub-total: | 200 | 50.0 |
| Coating ingredients | | |
| Opadry II Clear (macrogol 3350, polysorbate 80, polyvinyl alcohol and talc) - Seal coat | 8.0 | 2.0 |
| Orlistat | 46.7 | 11.7 |
| Acarbose | 6.7 | 1.7 |
| Opadry II Clear - Film former | 13.3 | 3.3 |
| Opadry II Clear - Seal coat | 8.0 | 2.0 |
| Acryl-EZE Clear (methacrylic acid copolymer type C, sodium lauryl sulphate, macrogol, talc, sodium bicarbonate and colloidal silica, anhydrous) - Enteric coat | 64.8 | 16.2 |
| Opadry II Clear - Seal coat | 8.0 | 2.0 |
| Acarbose - RR drug | 6.7 | 1.7 |
| Eudragit L30 D-55 (methacrylic acid-ethyl acetate copolymer (1:1) dispersion 30 percent) - Film former | 33.3 | 8.3 |
| Opadry II Clear - Top coat | 4.8 | 1.2 |
| Total: | 400 | 100 |

The coated tablets of Example 3 are prepared as follows:
Orlistat and acarbose is premixed with ethyl cellulose and sugar alcohol, such as lactose or mannitol, in a tumbling blender during approximately 10-30 minutes. The powder mix is dry granulated (roller compacted) and screen sieved through a 2 mm screen. Microcrystalline cellulose, croscarmellose sodium and silica colloidal, anhydrous is added and mixed for additionally 10-30 minutes depending on mixer. Sieve magnesium stearate through a 100-250-μm sieve, add to the tumbling mixer and mix for additional approximately 2 minutes, depending on mixer. The powder mix is transferred to a rotary tablet press to compress tablet cores of 200 mg or 300 mg. The coating dispersions are prepared layer by layer in a fluidized bed coater with bottom spray or similar to a final target average dry weight per tablet of 400 mg or 600 mg.

Especially the composition of Example 3D had excellent properties. The other composition had good/acceptable properties.

Example 4. Multiple-Unit Capsule

Example 4A, Orlistat 90 mg/Acarbose 30 mg

| Ingredient | % w/w |
|---|---|
| $DR_{DC}$-$PR_{GASTRIC}$ Granules (G1) | |
| Acarbose | 0.4-1.2 |
| Filler | 0-20 |
| Disintegrant | 0-5 |
| Binder | 0-5 |
| Prolonged release polymer | 0-10 |
| Coating polymer, 30-60 min delay | 1-10 |
| Sub-total: | 1.4-51 |
| $DR_{EC}$-$RR_{PROX\,SI}$ Granules (G2) | |
| Orlistat | 6-16 |
| Acarbose | 3-6 |
| Filler | 0-10 |
| Binder | 0-10 |
| Disintegrant | 0-10 |
| Solubilizer | 0-5 |
| Sub-coating polymer | 0-5 |
| Enteric coating polymer | 1-11 |
| Sub-total: | 10-73 |
| $DR_{DC}$-$PR_{GASTRIC}$ Granules (G3) | |
| Orlistat | 3-6 |
| Prolonged release polymer | 10-60 |
| Coating polymer, 30-60 min delay | 0-10 |
| Sub-total: | 13-76 |
| Extragranular ingredients | |
| Glidant | 0-2 |
| Lubricant | 0-5 |
| Total: | 100 |

Example 4B, Orlistat 90 mg/Acarbose 30 mg

| Ingredient | mg/capsule | % w/w |
|---|---|---|
| $DR_{DC}$-$PR_{GASTRIC}$ Granules | | |
| Acarbose | 5 | 0.8 |
| Filler | 47 | 7.8 |
| Disintegrant | 5 | 0.8 |
| Binder | 3 | 0.5 |
| Prolonged release polymer | 30 | 5.0 |
| Coating polymer, 30-60 min delay | 10 | 1.7 |
| Sub-total: | 100 | 17 |
| $DR_{EC}$-$RR_{PROX\,SI}$ Granules | | |
| Orlistat | 65 | 11 |
| Acarbose | 25 | 4.2 |
| Filler | 30 | 5.0 |
| Binder | 25 | 4.2 |
| Disintegrant | 30 | 5.0 |
| Solubilizer | 5 | 0.8 |

-continued

| Ingredient | mg/capsule | % w/w |
|---|---|---|
| Sub-coating polymer | 12 | 2.0 |
| Enteric coating polymer | 48 | 8.0 |
| Sub-total: | 230 | 38 |
| DR$_{DC}$-PR$_{GASTRIC}$ Granules | | |
| Orlistat | 25 | 4.2 |
| Prolonged release polymer | 215 | 36 |
| Coating polymer, 30-60 min delay | 10 | 1.7 |
| Sub-total: | 250 | 42 |
| Extragranular ingredients | | |
| Glidant | 5 | 0.8 |
| Lubricant | 15 | 2.5 |
| Total: | 600 | 100 |

Example 4C (Size 0, HPMC), Orlistat 90 mg/Acarbose 30 mg

| Ingredient | mg/capsule | % w/w |
|---|---|---|
| DR$_{DC}$-PR$_{GASTRIC}$ Granules | | |
| Acarbose | 5 | 0.8 |
| Mannitol | 47 | 7.8 |
| Croscarmellose sodium | 5 | 0.8 |
| Polyvinylpyrrolidone | 3 | 0.5 |
| Ethylcellulose | 30 | 5.0 |
| Eudragit L30 D-55 (methacrylic acid-ethyl acetate copolymer (1:1) dispersion 30 percent) | 10 | 1.7 |
| Sub-total: | 100 | 17 |
| DR$_{EC}$-RR$_{PROX\ SI}$ Granules | | |
| Orlistat | 65 | 11 |
| Acarbose | 25 | 4.2 |
| Microcrystalline cellulose | 30 | 5.0 |
| Polyvinylpyrrolidone, Povidone | 25 | 4.2 |
| Sodium starch glycolate, Primojel | 30 | 5.0 |
| Sodium lauryl sulphate, SDS | 5 | 0.8 |
| Opadry II Clear (macrogol 3350, polysorbate 80, polyvinyl alcohol and talc) | 12 | 2.0 |
| Acryl-EZE Clear (methacrylic acid copolymer type C, sodium lauryl sulphate, macrogol, talc, sodium bicarbonate and colloidal silica, anhydrous) | 48 | 8.0 |
| Sub-total: | 230 | 38 |
| DR$_{DC}$-PR$_{GASTRIC}$ Granules | | |
| Orlistat | 25 | 4.2 |
| Hypromellose, HPMC K100 | 215 | 36 |
| Eudragit L30 D-55 (methacrylic acid-ethyl acetate copolymer (1:1) dispersion 30 percent) | 10 | 1.7 |
| Sub-total: | 250 | 42 |
| Extragranular ingredients | | |
| Silica, colloidal anhydrous | 5 | 0.8 |
| Sodium stearyl fumarate | 15 | 2.5 |
| Total: | 600 | 100 |

Example 4D (Size 0, HPMC), Orlistat 90 mg/Acarbose 30 mg

| Ingredient | mg/capsule | % w/w |
|---|---|---|
| DR$_{DC}$-PR$_{GASTRIC}$ Granules | | |
| Acarbose | 5 | 0.8 |
| Mannitol | 47 | 7.8 |
| Croscarmellose sodium | 5 | 0.8 |
| Polyvinylpyrrolidone | 3 | 0.5 |
| Ethylcellulose | 30 | 5.0 |
| Eudragit L30 D-55 (methacrylic acid-ethyl acetate copolymer (1:1) dispersion 30 percent) | 10 | 1.7 |
| Sub-total: | 100 | 17 |
| DR$_{EC}$-RR$_{PROX\ SI}$ Granules | | |
| Orlistat | 65 | 11 |
| Acarbose | 25 | 4.2 |
| Microcrystalline cellulose | 30 | 5.0 |
| Polyvinylpyrrolidone, Povidone | 25 | 4.2 |
| Sodium starch glycolate, Primojel | 30 | 5.0 |
| Sodium lauryl sulphate, SDS | 5 | 0.8 |
| Opadry II Clear (macrogol 3350, polysorbate 80, polyvinyl alcohol and talc) | 12 | 2.0 |
| Acryl-EZE Clear (methacrylic acid copolymer type C, sodium lauryl sulphate, macrogol, talc, sodium bicarbonate and colloidal silica, anhydrous) | 48 | 8.0 |
| Sub-total: | 230 | 38 |
| DR$_{DC}$-PR$_{GASTRIC}$ Granules | | |
| Orlistat | 25 | 4.2 |
| Hypromellose, HPMC K100 | 215 | 36 |
| Eudragit L30 D-55 (methacrylic acid-ethyl acetate copolymer (1:1) dispersion 30 percent) | 10 | 1.7 |
| Sub-total: | 250 | 42 |
| Extragranular ingredients | | |
| Silica, colloidal anhydrous | 5 | 0.8 |
| Sodium stearyl fumarate | 15 | 2.5 |
| Total: | 600 | 100 |

Example 4E (Size 1, HPMC), Orlistat 60 mg/Acarbose 20 mg

| Ingredient | mg/capsule | % w/w |
|---|---|---|
| DR$_{DC}$-PR$_{GASTRIC}$ Granules | | |
| Acarbose | 3.3 | 0.8 |
| Mannitol | 31.3 | 7.8 |
| Croscarmellose sodium | 3.3 | 0.8 |
| Polyvinylpyrrolidone | 2.0 | 0.5 |
| Ethylcellulose | 20.0 | 5.0 |
| Eudragit L30 D-55 (methacrylic acid-ethyl acetate copolymer (1:1) dispersion 30 percent) | 6.7 | 1.7 |
| Sub-total: | 66.7 | 16.7 |
| DR$_{EC}$-RR$_{PROX\ SI}$ Granules | | |
| Orlistat | 43.3 | 10.8 |
| Acarbose | 16.7 | 4.2 |
| Microcrystalline cellulose | 20.0 | 5.0 |
| Polyvinylpyrrolidone, Povidone | 16.7 | 4.2 |
| Sodium starch glycolate, Primojel | 20.0 | 5.0 |
| Sodium lauryl sulphate, SDS | 3.3 | 0.8 |

| Ingredient | mg/capsule | % w/w |
|---|---|---|
| Opadry II Clear (macrogol 3350, polysorbate 80, polyvinyl alcohol and talc) | 8.0 | 2.0 |
| Acryl-EZE Clear (methacrylic acid copolymer type C, sodium lauryl sulphate, macrogol, talc, sodium bicarbonate and colloidal silica, anhydrous) | 32.0 | 8.0 |
| Sub-total: | 160 | 40.0 |
| DR$_{DC}$-PR$_{GASTRIC}$ Granules | | |
| Orlistat | 16.7 | 4.2 |
| Hypromellose, HPMC K100 | 143 | 35.8 |
| Eudragit L30 D-55 (methacrylic acid-ethyl acetate copolymer (1:1) dispersion 30 percent) | 6.7 | 1.7 |
| Sub-total: | 167 | 41.7 |
| Extragranular ingredients | | |
| Silica, colloidal anhydrous | 3.3 | 0.8 |
| Sodium stearyl fumarate | 10 | 2.5 |
| Total: | 400 | 100 |

Example 4F (Size 00, Hard Gelatin), Orlistat 60 mg/Acarbose 20 mg

| Ingredient | % w/w |
|---|---|
| DR$_{DC}$-PR$_{GASTRIC}$ Granules (G1) | |
| Acarbose | 1-5 |
| Film-coating polymer, water-soluble | 1-10 |
| Delayed release coating polymer, poorly water-soluble | 1-5 |
| Coating sphere, filler | 1-5 |
| Sub-total: | 5-20 |
| DR$_{EC}$-RR$_{PROX SI}$ Granules (G2) | |
| Orlistat | 5-10 |
| Acarbose | 0-5 |
| Film-coating polymer | 2-6 |
| Coating sphere, filler | 10-30 |
| Surface active agent | 0-10 |
| Enteric coating film based on methacrylic acid copolymer | 20-40 |
| Sub-total: | 45-95 |
| DR$_{DC}$-PR$_{GASTRIC}$ Granules (G3) | |
| Orlistat | 0-5 |
| Surface active agent | 0-2 |
| Filler | 0-5 |
| Sub-total: | 0-10 |
| Extragranular ingredients | |
| Glidant | 0-2 |
| Lubricant | 0-5 |
| Total: | 100 |

Example 4G (Size 00, Hard Gelatin), Orlistat 60 mg/Acarbose 20 mg

| Ingredient | mg/tablet | % w/w |
|---|---|---|
| DR$_{DC}$-PR$_{GASTRIC}$ Granules (G1) | | |
| Acarbose | 11.7 | 2.7 |
| Hydroxypropyl methylcellulose | 1.6 | 0.4 |
| Ethylcellulose, Surelease | 6.8 | 1.6 |
| Microcrystalline cellulose, Celphere CP 203 | 9.9 | 2.3 |
| Sub-total: | 30.0 | 6.9 |
| DR$_{EC}$-RR$_{PROX SI}$ Granules (G2) | | |
| Orlistat | 43.3 | 9.9 |
| Acarbose | 8.3 | 1.9 |
| Hydroxypropyl cellulose, Klucel | 15.4 | 3.5 |
| Microcrystalline cellulose, Celphere CP 203 | 109 | 24.9 |
| Polysorbate 80, Tween 80 | 5.6 | 1.3 |
| Opadry (HPMC low viscosity grade, 6 cps, tri-acetin, and talc) | 9.4 | 2.2 |
| Eudragit L 100-55 (methacrylic acid-ethyl acrylate copolymer (1:1) Type A) | 99.4 | 22.7 |
| Triethyl citrate | 10.1 | 2.3 |
| Talc | 74.6 | 17.1 |
| Sub-total: | 375 | 85.8 |
| DR$_{DC}$-PR$_{GASTRIC}$ Granules (G3) | | |
| Orlistat | 16.7 | 3.8 |
| Polysorbate 80, Tween 80 | 5.8 | 1.3 |
| Microcrystalline cellulose | 7.5 | 1.7 |
| Sub-total: | 30.0 | 6.9 |
| Extragranular ingredients | | |
| Magnesium stearate | 2.2 | 0.5 |
| Total: | 437 | 100 |

Example 4H (Size 00, Hard Gelatin), Orlistat 90 mg/Acarbose 30 mg

| Ingredient | mg/tablet | % w/w |
|---|---|---|
| DR$_{DC}$-PR$_{GASTRIC}$ Granules (G1) | | |
| Acarbose | 18.0 | 2.7 |
| Hydroxypropyl methylcellulose | 2.4 | 0.4 |
| Ethylcellulose, Surelease | 10.2 | 1.5 |
| Microcrystalline cellulose, Celphere CP 203 | 14.9 | 2.2 |
| Sub-total: | 45.5 | 6.8 |
| DR$_{EC}$-RR$_{PROX SI}$ Granules (G2) | | |
| Orlistat | 65.0 | 9.7 |
| Acarbose | 12.0 | 1.8 |
| Hydroxypropyl cellulose, Klucel | 23.0 | 3.4 |
| Microcrystalline cellulose, Celphere CP 203 | 163 | 24.3 |
| Polysorbate 80, Tween 80 | 8.3 | 1.2 |
| Eudragit L 100-55 (methacrylic acid - ethyl acrylate copolymer (1:1) Type A) | 199 | 29.6 |
| Triethyl citrate | 20.1 | 3.0 |
| Talc | 99.9 | 14.9 |
| Sub-total: | 591 | 87.9 |
| DR$_{DC}$-PR$_{GASTRIC}$ Granules (G3) | | |
| Orlistat | 25.0 | 3.7 |
| Polysorbate 80, Tween 80 | 1.4 | 0.2 |
| Microcrystalline cellulose | 9.3 | 1.4 |
| Sub-total: | 35.7 | 5.3 |
| Total: | 672 | 100 |

The in vitro dissolution behaviour appears from FIGS. 11-16. From these figures it is seen that the desired dissolution profiles are obtained for the individual granules G1, G2 and G3 as well as for the final composition, wherein G1, G2 and G3 are combined.

Example 4I (Size 00, Hard Gelatin), Orlistat 60 mg/Acarbose 20 mg

As 4G, but G2 extruded and spheronized pellet core.

| Ingredient | mg/tablet | % w/w |
|---|---|---|
| DR$_{DC}$-PR$_{GASTRIC}$ Granules (G1) | | |
| Acarbose | 11.7 | 4.3 |
| Hydroxypropyl methylcellulose | 1.6 | 0.6 |
| Ethylcellulose, Surelease | 6.8 | 2.5 |
| Microcrystalline cellulose, Celphere CP 203 | 9.9 | 3.6 |
| Sub-total: | 30.0 | 11.0 |
| DR$_{EC}$-RR$_{PROX\,SI}$ Granules (G2) | | |
| Orlistat | 43.3 | 15.9 |
| Acarbose | 8.3 | 3.0 |
| Microcrystalline cellulose | 65.8 | 24.1 |
| Polysorbate 80, Tween 80 | 13.4 | 4.9 |
| Mannitol | 9.8 | 3.6 |
| Croscarmellose sodium | 5.9 | 2.2 |
| Sodium stearyl fumarate, Pruv | 2.1 | 0.8 |
| Opadry (HPMC low viscosity grade, 6 cps, triacetin, and talc) | 4.5 | 1.6 |
| Acryl-EZE (methacrylic acid copolymer Type C, sodium lauryl sulphate, macrogol, talc, sodium bicarbonate and colloidal silica, anhydrous) | 59.5 | 21.8 |
| Sub-total: | 212 | 77.7 |
| DR$_{DC}$-PR$_{GASTRIC}$ Granules (G3) | | |
| Orlistat | 16.7 | 6.1 |
| Polysorbate 80, Tween 80 | 5.8 | 2.1 |
| Microcrystalline cellulose | 7.5 | 2.7 |
| Sub-total: | 30.0 | 11.0 |
| Extragranular ingredients | | |
| Magnesium stearate | 1.4 | 0.5 |
| Total: | 273 | 100 |

Example 4J (Size 00, Hard Gelatin), Orlistat 60 mg/Acarbose 20 mg

G1 extruded and spheronized with ethylcellulose/hydroxypropylmethylcellulose.

| Ingredient | % w/w |
|---|---|
| DR$_{DC}$-PR$_{GASTRIC}$ Granules (G1) | |
| Acarbose | 1-5 |
| Cellulose-based polymer, water-soluble | 1-10 |
| Delayed release polymer, poorly water-soluble | 1-10 |
| Lubricant | 0-5 |
| Sub-total: | 5-20 |
| DR$_{EC}$-RR$_{PROX\,SI}$ Granules (G2) | |
| Orlistat | 5-10 |
| Acarbose | 0-5 |
| Film-coating polymer | 2-6 |
| Coating sphere, filler | 10-30 |
| Surface active agent | 0-10 |
| Enteric coating film based on methacrylic acid copolymer | 20-40 |
| Sub-total: | 45-95 |
| DR$_{DC}$-PR$_{GASTRIC}$ Granules (G3) | |
| Orlistat | 0-5 |
| Surface active agent | 0-2 |
| Filler | 0-5 |
| Sub-total: | 0-10 |
| Extragranular ingredients | |
| Glidant | 0-2 |
| Lubricant | 0-5 |
| Total: | 100 |

Example 4K (Size 00, Hard Gelatin), Orlistat 60 mg/Acarbose 20 mg

G1 extruded and spheronized with ethylcellulose/hydroxypropylmethylcellulose.

| Ingredient | mg/tablet | % w/w |
|---|---|---|
| DR$_{DC}$-PR$_{GASTRIC}$ Granules (G1) | | |
| Acarbose | 11.7 | 2.5 |
| Hydroxypropyl methylcellulose | 22.8 | 4.9 |
| Ethylcellulose, Ethocel 10 FP | 23.4 | 5.0 |
| Sodium stearyl fumarate, Pruv | 0.6 | 0.1 |
| Sub-total: | 58.5 | 12.6 |
| DR$_{EC}$-RR$_{PROX\,SI}$ Granules (G2) | | |
| Orlistat | 43.3 | 9.3 |
| Acarbose | 8.3 | 1.8 |
| Hydroxypropyl cellulose, Klucel | 15.4 | 3.3 |
| Microcrystalline cellulose, Celphere CP 203 | 109 | 23.4 |
| Polysorbate 80, Tween 80 | 5.6 | 1.2 |
| Opadry (HPMC low viscosity grade, 6 cps, triacetin, and talc) | 9.4 | 2.0 |
| Eudragit L 100-55 (methacrylic acid - ethyl acrylate copolymer (1:1) Type A) | 99.4 | 21.3 |
| Triethyl citrate | 10.1 | 2.2 |
| Talc | 74.6 | 16.0 |
| Sub-total: | 375 | 80.5 |
| DR$_{DC}$-PR$_{GASTRIC}$ Granules (G3) | | |
| Orlistat | 16.7 | 3.6 |
| Polysorbate 80, Tween 80 | 5.8 | 1.2 |
| Microcrystalline cellulose | 7.5 | 1.6 |
| Sub-total: | 30.0 | 6.4 |
| Extragranular ingredients | | |
| Magnesium stearate | 2.3 | 0.5 |
| Total: | 466 | 100 |

Example 4L (Size 00, Hard Gelatin), Orlistat 60 mg/Acarbose 20 mg

G1 extruded and spheronized with ethylcellulose/hydroxypropylmethylcellulose. G2 extruded and spheronizes pellet cores.

| Ingredient | mg/tablet | % w/w |
|---|---|---|
| DR$_{DC}$-PR$_{GASTRIC}$ Granules (G1) | | |
| Acarbose | 11.7 | 3.9 |
| Hydroxypropyl methylcellulose | 22.8 | 7.5 |
| Ethylcellulose, Ethocel 10 FP | 23.4 | 7.7 |
| Sodium stearyl fumarate, Pruv | 0.6 | 0.2 |
| Sub-total: | 58.5 | 19.4 |
| DR$_{EC}$-RR$_{PROX\,SI}$ Granules (G2) | | |
| Orlistat | 43.3 | 14.3 |
| Acarbose | 8.3 | 2.7 |
| Microcrystalline cellulose | 65.8 | 21.8 |
| Polysorbate 80, Tween 80 | 13.4 | 4.4 |
| Mannitol | 9.8 | 3.2 |
| Croscarmellose sodium | 5.9 | 2.0 |
| Sodium stearyl fumarate, Pruv | 2.1 | 0.7 |
| Opadry (HPMC low viscosity grade, 6 cps, triacetin, and talc) | 4.5 | 1.5 |
| Acryl-EZE (methacrylic acid copolymer Type C, sodium lauryl sulphate, macrogol, talc, sodium bicarbonate and colloidal silica, anhydrous) | 59.5 | 19.7 |
| Sub-total: | 212 | 70.2 |
| DR$_{DC}$-PR$_{GASTRIC}$ Granules (G3) | | |
| Orlistat | 16.7 | 5.5 |
| Polysorbate 80, Tween 80 | 5.8 | 1.9 |
| Microcrystalline cellulose | 7.5 | 2.5 |
| Sub-total: | 30.0 | 9.9 |
| Extragranular ingredients | | |
| Magnesium stearate | 1.5 | 0.5 |
| Total: | 302 | 100 |

Example 4M (Size 00, Hard Gelatin), Orlistat 60 mg/Acarbose 20 mg

G1 extruded and spheronized with hard fat.

| Ingredient | % w/w |
|---|---|
| DR$_{DC}$-PR$_{GASTRIC}$ Granules (G1) | |
| Acarbose | 1-5 |
| Wax, water-soluble | 1-10 |
| Hard fat | 1-10 |
| Filler | 0-5 |
| Sub-total: | 5-20 |
| DR$_{EC}$-RR$_{PROX\,SI}$ Granules (G2) | |
| Orlistat | 5-10 |
| Acarbose | 0-5 |
| Film-coating polymer | 2-6 |
| Coating sphere, filler | 10-30 |
| Surface active agent | 0-10 |
| Enteric coating film based on methacrylic acid copolymer | 20-40 |
| Sub-total: | 45-95 |
| DR$_{DC}$-PR$_{GASTRIC}$ Granules (G3) | |
| Orlistat | 0-5 |
| Surface active agent | 0-2 |
| Filler | 0-5 |
| Sub-total: | 0-10 |
| Extragranular ingredients | |
| Glidant | 0-2 |
| Lubricant | 0-5 |
| Total: | 100 |

Example 4N (Size 00, Hard Gelatin), Orlistat 60 mg/Acarbose 20 mg

G1 extruded and spheronized with hard fat.

| Ingredient | mg/tablet | % w/w |
|---|---|---|
| DR$_{DC}$-PR$_{GASTRIC}$ Granules (G1) | | |
| Acarbose | 11.7 | 2.5 |
| Glyceryl monostearate | 18.7 | 4.0 |
| Hydrogenated vegetable oil type II, Dynasan P60 | 14.6 | 3.1 |
| Mannitol | 13.5 | 2.9 |
| Sub-total: | 58.5 | 12.6 |
| DR$_{EC}$-RR$_{PROX\,SI}$ Granules (G2) | | |
| Orlistat | 43.3 | 9.3 |
| Acarbose | 8.3 | 1.8 |
| Hydroxypropyl cellulose, Klucel | 15.4 | 3.3 |
| Microcrystalline cellulose, Celphere CP 203 | 109 | 23.4 |
| Polysorbate 80, Tween 80 | 5.6 | 1.2 |
| Opadry (HPMC low viscosity grade, 6 cps, triacetin, and talc) | 9.4 | 2.0 |
| Eudragit L 100-55 (methacrylic acid - ethyl acrylate copolymer (1:1) Type A) | 99.4 | 21.3 |
| Triethyl citrate | 10.1 | 2.2 |
| Talc | 74.6 | 16.0 |
| Sub-total: | 375 | 80.5 |
| DR$_{DC}$-PR$_{GASTRIC}$ Granules (G3) | | |
| Orlistat | 16.7 | 3.6 |
| Polysorbate 80, Tween 80 | 5.8 | 1.2 |
| Microcrystalline cellulose | 7.5 | 1.6 |
| Sub-total: | 30.0 | 6.4 |
| Extragranular ingredients | | |
| Magnesium stearate | 2.3 | 0.5 |
| Total: | 466 | 100 |

Example 4O (Size 00, Hard Gelatin), Orlistat 60 mg/Acarbose 20 mg

G1 extruded and spheronized with hard fat. G2 extruded and spheronized pellet cores.

| Ingredient | mg/tablet | % w/w |
|---|---|---|
| DR$_{DC}$-PR$_{GASTRIC}$ Granules (G1) | | |
| Acarbose | 11.7 | 3.9 |
| Glyceryl monostearate | 18.7 | 6.2 |
| Hydrogenated vegetable oil type II, Dynasan P60 | 14.6 | 4.8 |
| Mannitol | 13.5 | 4.5 |
| Sub-total: | 58.5 | 19.4 |

-continued

| Ingredient | mg/tablet | % w/w |
|---|---|---|
| DR$_{EC}$-RR$_{PROX\,SI}$ Granules (G2) | | |
| Orlistat | 43.3 | 14.3 |
| Acarbose | 8.3 | 2.7 |
| Microcrystalline cellulose | 65.8 | 21.8 |
| Polysorbate 80, Tween 80 | 13.4 | 4.4 |
| Mannitol | 9.8 | 3.2 |
| Croscarmellose sodium | 5.9 | 2.0 |
| Sodium stearyl fumarate, Pruv | 2.1 | 0.7 |
| Opadry (HPMC low viscosity grade, 6 cps, triacetin, and talc) | 4.5 | 1.5 |
| Acryl-EZE (methacrylic acid copolymer Type C, sodium lauryl sulphate, macrogol, talc, sodium bicarbonate and colloidal silica, anhydrous) | 59.5 | 19.7 |
| Sub-total: | 212 | 70.2 |
| DR$_{DC}$-PR$_{GASTRIC}$ Granules (G3) | | |
| Orlistat | 16.7 | 5.5 |
| Polysorbate 80, Tween 80 | 5.8 | 1.9 |
| Microcrystalline cellulose | 7.5 | 2.5 |
| Sub-total: | 30.0 | 9.9 |
| Extragranular ingredients | | |
| Magnesium stearate | 1.5 | 0.5 |
| Total: | 302 | 100 |

Example 4P (Size 00, Hard Gelatin), Orlistat 60 mg/Acarbose 20 mg

As 4G, but G3 is coated in fluidized bed.

| Ingredient | mg/tablet | % w/w |
|---|---|---|
| DR$_{DC}$-PR$_{GASTRIC}$ Granules (G1) | | |
| Acarbose | 11.7 | 2.7 |
| Hydroxypropyl methylcellulose | 1.6 | 0.4 |
| Ethylcellulose, Surelease | 6.8 | 1.6 |
| Microcrystalline cellulose, Celphere CP 203 | 9.9 | 2.3 |
| Sub-total: | 30.0 | 6.9 |
| DR$_{EC}$-RR$_{PROX\,SI}$ Granules (G2) | | |
| Orlistat | 43.3 | 9.9 |
| Acarbose | 8.3 | 1.9 |
| Hydroxypropyl cellulose, Klucel | 15.4 | 3.5 |
| Microcrystalline cellulose, Celphere CP 203 | 109 | 24.9 |
| Polysorbate 80, Tween 80 | 5.6 | 1.3 |
| Opadry (HPMC low viscosity grade, 6 cps, triacetin, and talc) | 9.4 | 2.2 |
| Eudragit L 100-55 (methacrylic acid - ethyl acrylate copolymer (1:1) Type A) | 99.4 | 22.7 |
| Triethyl citrate | 10.1 | 2.3 |
| Talc | 74.6 | 17.1 |
| Sub-total: | 375 | 85.8 |
| DR$_{DC}$-PR$_{GASTRIC}$ Granules (G3) | | |
| Orlistat | 16.7 | 3.8 |
| Hydroxypropyl cellulose, Klucel | 5.8 | 1.3 |
| Microcrystalline cellulose, Celphere CP 203 | 7.5 | 1.7 |
| Sub-total: | 30.0 | 6.9 |
| Extragranular ingredients | | |
| Magnesium stearate | 2.2 | 0.5 |
| Total: | 437 | 100 |

Example 4Q (Size 00, Hard Gelatin), Orlistat 60 mg or Acarbose 20 mg

Composition only containing acarbose (G1 and G2 without orlistat), or composition only containing orlistat (G2 without acarbose) and G3.

| Ingredient | % w/w |
|---|---|
| DR$_{DC}$-PR$_{GASTRIC}$ Granules (G1) | |
| Acarbose | 0-5 |
| Film-coating polymer, water-soluble | 0-10 |
| Delayed release coating polymer, poorly water-soluble | 0-5 |
| Coating sphere, filler | 0-5 |
| Sub-total: | 0-25 |
| DR$_{EC}$-RR$_{PROX\,SI}$ Granules (G2) | |
| Orlistat | 0-10 |
| Acarbose | 0-5 |
| Film-coating polymer | 2-6 |
| Coating sphere, filler | 10-30 |
| Surface active agent | 0-10 |
| Enteric coating film based on methacrylic acid copolymer | 20-40 |
| Sub-total: | 45-95 |
| DR$_{DC}$-PR$_{GASTRIC}$ Granules (G3) | |
| Orlistat | 0-5 |
| Surface active agent | 0-2 |
| Filler | 0-8 |
| Sub-total: | 0-15 |
| Extragranular ingredients | |
| Filler | 0-50 |
| Glidant | 0-2 |
| Lubricant | 0-5 |
| Total: | 100 |

Example 4R (Size 00, Hard Gelatin), Acarbose 20 mg

| Ingredient | mg/tablet | % w/w |
|---|---|---|
| DR$_{DC}$-PR$_{GASTRIC}$ Granules (G1) | | |
| Acarbose | 11.7 | 2.9 |
| Hydroxypropyl methylcellulose | 1.6 | 0.4 |
| Ethylcellulose, Surelease | 6.8 | 1.7 |
| Microcrystalline cellulose, Celphere CP 203 | 9.9 | 2.4 |
| Sub-total: | 30.0 | 7.4 |
| DR$_{EC}$-RR$_{PROX\,SI}$ Granules (G2) | | |
| Acarbose | 8.3 | 2.0 |
| Hydroxypropyl cellulose, Klucel | 15.4 | 3.8 |
| Microcrystalline cellulose, Celphere CP 203 | 152 | 37.3 |
| Polysorbate 80, Tween 80 | 5.6 | 1.4 |
| Opadry (HPMC low viscosity grade, 6 cps, triacetin, and talc) | 9.4 | 2.3 |
| Eudragit L 100-55 (methacrylic acid - ethyl acrylate copolymer (1:1) Type A) | 99.4 | 24.4 |
| Triethyl citrate | 10.1 | 2.5 |
| Talc | 74.6 | 18.3 |
| Sub-total: | 375 | 92.1 |

-continued

| Ingredient | mg/tablet | % w/w |
|---|---|---|
| Extragranular ingredients | | |
| Magnesium stearate | 2.0 | 0.5 |
| Total: | 407 | 100 |

Example 4S (Size 00, Hard Gelatin), Orlistat 60 mg

| Ingredient | mg/tablet | % w/w |
|---|---|---|
| $DR_{EC}$-$RR_{PROX\,SI}$ Granules (G2) | | |
| Orlistat | 43.3 | 10.6 |
| Hydroxypropyl cellulose, Klucel | 15.4 | 3.8 |
| Microcrystalline cellulose, Celphere CP 203 | 121 | 29.7 |
| Polysorbate 80, Tween 80 | 5.6 | 1.4 |
| Opadry (HPMC low viscosity grade, 6 cps, triacetin, and talc) | 9.4 | 2.3 |
| Eudragit L 100-55 (methacrylic acid - ethyl acrylate copolymer (1:1) Type A) | 99.4 | 24.4 |
| Triethyl citrate | 10.1 | 2.5 |
| Talc | 74.6 | 18.3 |
| Sub-total: | 375 | 92.1 |
| $DR_{DC}$-$PR_{GASTRIC}$ Granules (G3) | | |
| Orlistat | 16.7 | 4.1 |
| Polysorbate 80, Tween 80 | 5.8 | 1.4 |
| Microcrystalline cellulose | 7.5 | 1.8 |
| Sub-total: | 30.0 | 7.4 |
| Extragranular ingredients | | |
| Magnesium stearate | 2.0 | 0.5 |
| Total: | 407 | 100 |

The multiple-unit capsules of Example 4 are prepared as follows:

The granules are prepared as described in Example 1 above except for the G3 granules in Example 4P, where the G3 granules are not prepared by wet granulation but by coating in a fluidized bed coater. When the granules are dry; add all components into a tumbling mixer. Mix them during approximately 45 minutes, depending on mixer, or add the granules to the hopper/s of a capsule filling machine separately by the use of multiple filling stations. When magnesium stearate is used as lubricant, add it after sieving during the last 2 minutes of blending. Transfer the final blend or separate granules to a standard capsule filling machine and fill HPMC-based or hard gelatin capsules of appropriate sizes in accordance with a powder content adjusted for the powder density and for the filling weight per capsule.

The composition of examples 4G, 4H, 4Q, 4R and 4S have excellent properties.

Example 5. Multiple-Unit Oral Powder

Example 5A (Filled in Sachets), Orlistat 90 mg/Acarbose 30 mg

| Ingredient | % w/w |
|---|---|
| $DR_{DC}$-$PR_{GASTRIC}$ Granules | |
| Acarbose | 0.4-1.2 |
| Filler | 0-20 |

| Ingredient | % w/w |
|---|---|
| Disintegrant | 0-5 |
| Binder | 0-5 |
| Prolonged release polymer | 0-10 |
| Coating polymer, 30-60 min delay | 1-10 |
| Sub-total: | 1.4-51 |
| $DR_{EC}$-$RR_{PROX\,SI}$ Granules | |
| Orlistat | 6-16 |
| Acarbose | 3-6 |
| Filler | 0-10 |
| Binder | 0-10 |
| Disintegrant | 0-10 |
| Solubilizer | 0-5 |
| Sub-coating polymer | 0-5 |
| Enteric coating polymer | 1-11 |
| Sub-total: | 10-73 |
| $DR_{DC}$-$PR_{GASTRIC}$ Granules | |
| Orlistat | 3-6 |
| Prolonged release polymer | 10-60 |
| Coating polymer, 30-60 min delay | 0-10 |
| Sub-total: | 13-76 |
| Extragranular ingredients | |
| Glidant | 0-2 |
| Lubricant | 0-5 |
| Total: | 100 |

Example 5B (Filled in Sachets), Orlistat 90 mg/Acarbose 30 mg

| Ingredient | mg/sachet | % w/w |
|---|---|---|
| $DR_{DC}$-$PR_{GASTRIC}$ Granules | | |
| Acarbose | 5 | 0.8 |
| Filler | 47 | 7.8 |
| Disintegrant | 5 | 0.8 |
| Binder | 3 | 0.5 |
| Prolonged release polymer | 30 | 5.0 |
| Coating polymer, 30-60 min delay | 10 | 1.7 |
| Sub-total: | 100 | 17 |
| $DR_{EC}$-$RR_{PROX\,SI}$ Granules | | |
| Orlistat | 65 | 11 |
| Acarbose | 25 | 4.2 |
| Filler | 30 | 5.0 |
| Binder | 25 | 4.2 |
| Disintegrant | 30 | 5.0 |
| Solubilizer | 5 | 0.8 |
| Sub-coating polymer | 12 | 2.0 |
| Enteric coating polymer | 48 | 8.0 |
| Sub-total: | 230 | 38 |
| $DR_{DC}$-$PR_{GASTRIC}$ Granules | | |
| Orlistat | 25 | 4.2 |
| Prolonged release polymer | 215 | 36 |
| Coating polymer, 30-60 min delay | 10 | 1.7 |
| Sub-total: | 250 | 42 |
| Extragranular ingredients | | |
| Glidant | 5 | 0.8 |
| Lubricant | 15 | 2.5 |
| Total: | 600 | 100 |

Example 5C (Filled in Sachets), Orlistat 90 mg/Acarbose 30 mg

| Ingredient | mg/sachet | % w/w |
|---|---|---|
| $DR_{DC}$-$PR_{GASTRIC}$ Granules | | |
| Acarbose | 5 | 0.8 |
| Mannitol | 47 | 7.8 |
| Croscarmellose sodium | 5 | 0.8 |
| Polyvinylpyrrolidone | 3 | 0.5 |
| Ethylcellulose | 30 | 5.0 |
| Eudragit L30 D-55 (methacrylic acid - ethyl acetate copolymer (1:1) dispersion 30 percent) | 10 | 1.7 |
| Sub-total: | 100 | 17 |
| $DR_{EC}$-$RR_{PROX\,SI}$ Granules | | |
| Orlistat | 65 | 11 |
| Acarbose | 25 | 4.2 |
| Microcrystalline cellulose | 30 | 5.0 |
| Polyvinylpyrrolidone, Povidone | 25 | 4.2 |
| Sodium starch glycolate, Primojel | 30 | 5.0 |
| Sodium lauryl sulphate, SDS | 5 | 0.8 |
| Opadry II Clear (macrogol 3350, polysorbate 80, polyvinyl alcohol and talc) | 12 | 2.0 |
| Acryl-EZE Clear (methacrylic acid copolymer type C, sodium lauryl sulphate, macrogol, talc, sodium bicarbonate and colloidal silica, anhydrous) | 48 | 8.0 |
| Sub-total: | 230 | 38 |
| $DR_{DC}$-$PR_{GASTRIC}$ Granules | | |
| Orlistat | 25 | 4.2 |
| Hypromellose, HPMC K100 | 215 | 36 |
| Eudragit L30 D-55 (methacrylic acid - ethyl acetate copolymer (1:1) dispersion 30 percent) | 10 | 1.7 |
| Sub-total: | 250 | 42 |
| Extragranular ingredients | | |
| Silica, colloidal anhydrous | 5 | 0.8 |
| Sodium stearyl fumarate | 15 | 2.5 |
| Total: | 600 | 100 |

The multiple-unit oral powders of Example 5A-C are prepared as follows:

The granules are prepared as described in Example 1 above. When the granules are dry; add all components into a tumbling mixer. Mix for approximately 45 minutes, depending on mixer. Transfer the final blend to a sachet filling and sealing machine and fill sachets with a powder content of 600 mg per sachet.

Example 5D (Filled in Sachets), Orlistat 60 mg/Acarbose 20 mg

| Ingredient | % w/w |
|---|---|
| $DR_{DC}$-$PR_{GASTRIC}$ Granules (G1) | |
| Acarbose | 1-5 |
| Film-coating polymer, water-soluble | 1-10 |
| Delayed release coating polymer, poorly water-soluble | 1-5 |
| Coating sphere, filler | 1-5 |
| Sub-total: | 5-20 |
| $DR_{EC}$-$RR_{PROX\,SI}$ Granules (G2) | |
| Orlistat | 5-10 |
| Acarbose | 0-5 |
| Film-coating polymer | 2-6 |
| Coating sphere, filler | 10-30 |
| Surface active agent | 0-10 |
| Enteric coating film based on methacrylic acid copolymer | 20-40 |
| Sub-total: | 45-95 |
| $DR_{DC}$-$PR_{GASTRIC}$ Granules (G3) | |
| Orlistat | 0-5 |
| Surface active agent | 0-2 |
| Filler | 0-5 |
| Sub-total: | 0-10 |
| Extragranular ingredients | |
| Glidant | 0-2 |
| Lubricant | 0-5 |
| Total: | 100 |

Example 5E (Filled in Sachets), Orlistat 60 mg/Acarbose 20 mg

| Ingredient | mg/tablet | % w/w |
|---|---|---|
| $DR_{DC}$-$PR_{GASTRIC}$ Granules (G1) | | |
| Acarbose | 11.7 | 2.7 |
| Hydroxypropyl methylcellulose | 1.6 | 0.4 |
| Ethylcellulose, Surelease | 6.8 | 1.6 |
| Microcrystalline cellulose, Celphere CP 203 | 9.9 | 2.3 |
| Sub-total: | 30.0 | 6.9 |
| $DR_{EC}$-$RR_{PROX\,SI}$ Granules (G2) | | |
| Orlistat | 43.3 | 9.9 |
| Acarbose | 8.3 | 1.9 |
| Hydroxypropyl cellulose, Klucel | 15.4 | 3.5 |
| Microcrystalline cellulose, Celphere CP 203 | 109 | 24.9 |
| Polysorbate 80, Tween 80 | 5.6 | 1.3 |
| Opadry (HPMC low viscosity grade, 6 cps, triacetin, and talc) | 9.4 | 2.2 |
| Eudragit L 100-55 (methacrylic acid - ethyl acrylate copolymer (1:1) Type A) | 99.4 | 22.7 |
| Triethyl citrate | 10.1 | 2.3 |
| Talc | 74.6 | 17.1 |
| Sub-total: | 375 | 85.8 |
| $DR_{DC}$-$PR_{GASTRIC}$ Granules (G3) | | |
| Orlistat | 16.7 | 3.8 |
| Polysorbate 80, Tween 80 | 5.8 | 1.3 |
| Microcrystalline cellulose | 7.5 | 1.7 |
| Sub-total: | 30.0 | 6.9 |
| Extragranular ingredients | | |
| Magnesium stearate | 2.2 | 0.5 |
| Total: | 437 | 100 |

Example 5F (Filled in Sachets), Orlistat 90 mg/Acarbose 30 mg

| Ingredient | mg/tablet | % w/w |
|---|---|---|
| $DR_{DC}$-$PR_{GASTRIC}$ Granules (G1) | | |
| Acarbose | 18.0 | 2.7 |
| Hydroxypropyl methylcellulose | 2.4 | 0.4 |

-continued

| Ingredient | mg/tablet | % w/w |
|---|---|---|
| Ethylcellulose, Surelease | 10.2 | 1.5 |
| Microcrystalline cellulose, Celphere CP 203 | 14.9 | 2.2 |
| Sub-total: | 45.5 | 6.8 |
| $DR_{EC}$-$RR_{PROX\,SI}$ Granules (G2) | | |
| Orlistat | 65.0 | 9.7 |
| Acarbose | 12.0 | 1.8 |
| Hydroxypropyl cellulose, Klucel | 23.0 | 3.4 |
| Microcrystalline cellulose, Celphere CP 203 | 163 | 24.3 |
| Polysorbate 80, Tween 80 | 8.3 | 1.2 |
| Eudragit L 100-55 (methacrylic acid - ethyl acrylate copolymer (1:1) Type A) | 199 | 29.6 |
| Triethyl citrate | 20.1 | 3.0 |
| Talc | 99.9 | 14.9 |
| Sub-total: | 591 | 87.9 |
| $DR_{DC}$-$PR_{GASTRIC}$ Granules (G3) | | |
| Orlistat | 25.0 | 3.7 |
| Polysorbate 80, Tween 80 | 1.4 | 0.2 |
| Microcrystalline cellulose | 9.3 | 1.4 |
| Sub-total: | 35.7 | 5.3 |
| Total: | 672 | 100 |

Example 5G (Filled in Sachets), Orlistat 60 mg/Acarbose 20 mg

As 5E, but G2 is extruded and spheronized pellet cores.

| Ingredient | mg/tablet | % w/w |
|---|---|---|
| $DR_{DC}$-$PR_{GASTRIC}$ Granules (G1) | | |
| Acarbose | 11.7 | 4.3 |
| Hydroxypropyl methylcellulose | 1.6 | 0.6 |
| Ethylcellulose, Surelease | 6.8 | 2.5 |
| Microcrystalline cellulose, Celphere CP 203 | 9.9 | 3.6 |
| Sub-total: | 30.0 | 11.0 |
| $DR_{EC}$-$RR_{PROX\,SI}$ Granules (G2) | | |
| Orlistat | 43.3 | 15.9 |
| Acarbose | 8.3 | 3.0 |
| Microcrystalline cellulose | 65.8 | 24.1 |
| Polysorbate 80, Tween 80 | 13.4 | 4.9 |
| Mannitol | 9.8 | 3.6 |
| Croscarmellose sodium | 5.9 | 2.2 |
| Sodium stearyl fumarate, Pruv | 2.1 | 0.8 |
| Opadry (HPMC low viscosity grade, 6 cps, tri-acetin, and talc) | 4.5 | 1.6 |
| Acryl-EZE (methacrylic acid copolymer Type C, sodium lauryl sulphate, macrogol, talc, sodium bicarbonate and colloidal silica, anhydrous) | 59.5 | 21.8 |
| Sub-total: | 212 | 77.7 |
| $DR_{DC}$-$PR_{GASTRIC}$ Granules (G3) | | |
| Orlistat | 16.7 | 6.1 |
| Polysorbate 80, Tween 80 | 5.8 | 2.1 |
| Microcrystalline cellulose | 7.5 | 2.7 |
| Sub-total: | 30.0 | 11.0 |
| Extragranular ingredients | | |
| Magnesium stearate | 1.4 | 0.5 |
| Total: | 273 | 100 |

Example 5H (Filled in Sachets), Orlistat 60 mg/Acarbose 20 mg

G1 is extruded and spheronized with ethylcellulose/hydroxypropylmethylcellulose.

| Ingredient | % w/w |
|---|---|
| $DR_{DC}$-$PR_{GASTRIC}$ Granules (G1) | |
| Acarbose | 1-5 |
| Cellulose-based polymer, water-soluble | 1-10 |
| Delayed release polymer, poorly water-soluble | 1-10 |
| Lubricant | 0-5 |
| Sub-total: | 5-20 |
| $DR_{EC}$-$RR_{PROX\,SI}$ Granules (G2) | |
| Orlistat | 5-10 |
| Acarbose | 0-5 |
| Film-coating polymer | 2-6 |
| Coating sphere, filler | 10-30 |
| Surface active agent | 0-10 |
| Enteric coating film based on methacrylic acid copolymer | 20-40 |
| Sub-total: | 45-95 |
| $DR_{DC}$-$PR_{GASTRIC}$ Granules (G3) | |
| Orlistat | 0-5 |
| Surface active agent | 0-2 |
| Filler | 0-5 |
| Sub-total: | 0-10 |
| Extragranular ingredients | |
| Glidant | 0-2 |
| Lubricant | 0-5 |
| Total: | 100 |

Example 5I (Filled in Sachets), Orlistat 60 mg/Acarbose 20 mg

G1 is extruded and spheronized with ethylcellulose/hydroxypropylmethylcellulose.

| Ingredient | mg/tablet | % w/w |
|---|---|---|
| $DR_{DC}$-$PR_{GASTRIC}$ Granules (G1) | | |
| Acarbose | 11.7 | 2.5 |
| Hydroxypropyl methylcellulose | 22.8 | 4.9 |
| Ethylcellulose, Ethocel 10 FP | 23.4 | 5.0 |
| Sodium stearyl fumarate, Pruv | 0.6 | 0.1 |
| Sub-total: | 58.5 | 12.6 |
| $DR_{EC}$-$RR_{PROX\,SI}$ Granules (G2) | | |
| Orlistat | 43.3 | 9.3 |
| Acarbose | 8.3 | 1.8 |
| Hydroxypropyl cellulose, Klucel | 15.4 | 3.3 |
| Microcrystalline cellulose, Celphere CP 203 | 109 | 23.4 |
| Polysorbate 80, Tween 80 | 5.6 | 1.2 |
| Opadry (HPMC low viscosity grade, 6 cps, tri-acetin, and talc) | 9.4 | 2.0 |
| Eudragit L 100-55 (methacrylic acid - ethyl acrylate copolymer (1:1) Type A) | 99.4 | 21.3 |
| Triethyl citrate | 10.1 | 2.2 |
| Talc | 74.6 | 16.0 |
| Sub-total: | 375 | 80.5 |

-continued

| Ingredient | mg/tablet | % w/w |
|---|---|---|
| $DR_{DC}$-$PR_{GASTRIC}$ Granules (G3) | | |
| Orlistat | 16.7 | 3.6 |
| Polysorbate 80, Tween 80 | 5.8 | 1.2 |
| Microcrystalline cellulose | 7.5 | 1.6 |
| Sub-total: | 30.0 | 6.4 |
| Extragranular ingredients | | |
| Magnesium stearate | 2.3 | 0.5 |
| Total: | 466 | 100 |

Example 5J (Filled in Sachets), Orlistat 60 mg/Acarbose 20 mg

G1 is extruded and spheronized with ethylcellulose/hydroxypropylmethylcellulose. G2 is extruded and spheronized pellet cores.

| Ingredient | mg/tablet | % w/w |
|---|---|---|
| $DR_{DC}$-$PR_{GASTRIC}$ Granules (G1) | | |
| Acarbose | 11.7 | 3.9 |
| Hydroxypropyl methylcellulose | 22.8 | 7.5 |
| Ethylcellulose, Ethocel 10 FP | 23.4 | 7.7 |
| Sodium stearyl fumarate, Pruv | 0.6 | 0.2 |
| Sub-total: | 58.5 | 19.4 |
| $DR_{EC}$-$RR_{PROX SI}$ Granules (G2) | | |
| Orlistat | 43.3 | 14.3 |
| Acarbose | 8.3 | 2.7 |
| Microcrystalline cellulose | 65.8 | 21.8 |
| Polysorbate 80, Tween 80 | 13.4 | 4.4 |
| Mannitol | 9.8 | 3.2 |
| Croscarmellose sodium | 5.9 | 2.0 |
| Sodium stearyl fumarate, Pruv | 2.1 | 0.7 |
| Opadry (HPMC low viscosity grade, 6 cps, tri-acetin, and talc) | 4.5 | 1.5 |
| Acryl-EZE (methacrylic acid copolymer Type C, sodium lauryl sulphate, macrogol, talc, sodium bicarbonate and colloidal silica, anhydrous) | 59.5 | 19.7 |
| Sub-total: | 212 | 70.2 |
| $DR_{DC}$-$PR_{GASTRIC}$ Granules (G3) | | |
| Orlistat | 16.7 | 5.5 |
| Polysorbate 80, Tween 80 | 5.8 | 1.9 |
| Microcrystalline cellulose | 7.5 | 2.5 |
| Sub-total: | 30.0 | 9.9 |
| Extragranular ingredients | | |
| Magnesium stearate | 1.5 | 0.5 |
| Total: | 302 | 100 |

Example 5K (Filled in Sachets), Orlistat 60 mg/Acarbose 20 mg

G1 extruded and spheronized with hard fat.

| Ingredient | % w/w |
|---|---|
| $DR_{DC}$-$PR_{GASTRIC}$ Granules (G1) | |
| Acarbose | 1-5 |
| Wax, water-soluble | 1-10 |
| Hard fat | 1-10 |
| Filler | 0-5 |
| Sub-total: | 5-20 |
| $DR_{EC}$-$RR_{PROX SI}$ Granules (G2) | |
| Orlistat | 5-10 |
| Acarbose | 0-5 |
| Film-coating polymer | 2-6 |
| Coating sphere, filler | 10-30 |
| Surface active agent | 0-10 |
| Enteric coating film based on methacrylic acid copolymer | 20-40 |
| Sub-total: | 45-95 |
| $DR_{DC}$-$PR_{GASTRIC}$ Granules (G3) | |
| Orlistat | 0-5 |
| Surface active agent | 0-2 |
| Filler | 0-5 |
| Sub-total: | 0-10 |
| Extragranular ingredients | |
| Glidant | 0-2 |
| Lubricant | 0-5 |
| Total: | 100 |

Example 5L (Filled in Sachets), Orlistat 60 mg/Acarbose 20 mg

G1 extruded and spheronized with hard fat.

| Ingredient | mg/tablet | % w/w |
|---|---|---|
| $DR_{DC}$-$PR_{GASTRIC}$ Granules (G1) | | |
| Acarbose | 11.7 | 2.5 |
| Glyceryl monostearate | 18.7 | 4.0 |
| Hydrogenated vegetable oil type II, Dynasan P60 | 14.6 | 3.1 |
| Mannitol | 13.5 | 2.9 |
| Sub-total: | 58.5 | 12.6 |
| $DR_{EC}$-$RR_{PROX SI}$ Granules (G2) | | |
| Orlistat | 43.3 | 9.3 |
| Acarbose | 8.3 | 1.8 |
| Hydroxypropyl cellulose, Klucel | 15.4 | 3.3 |
| Microcrystalline cellulose, Celphere CP 203 | 109 | 23.4 |
| Polysorbate 80, Tween 80 | 5.6 | 1.2 |
| Opadry (HPMC low viscosity grade, 6 cps, tri-acetin, and talc) | 9.4 | 2.0 |
| Eudragit L 100-55 (methacrylic acid - ethyl acrylate copolymer (1:1) Type A) | 99.4 | 21.3 |
| Triethyl citrate | 10.1 | 2.2 |
| Talc | 74.6 | 16.0 |
| Sub-total: | 375 | 80.5 |
| $DR_{DC}$-$PR_{GASTRIC}$ Granules (G3) | | |
| Orlistat | 16.7 | 3.6 |
| Polysorbate 80, Tween 80 | 5.8 | 1.2 |
| Microcrystalline cellulose | 7.5 | 1.6 |
| Sub-total: | 30.0 | 6.4 |
| Extragranular ingredients | | |
| Magnesium stearate | 2.3 | 0.5 |
| Total: | 466 | 100 |

Example 5M (Filled in Sachets), Orlistat 60 mg/Acarbose 20 mg

G1 extruded and spheronized with hard fat. G2 extruded and spheronized pellet cores.

| Ingredient | mg/tablet | % w/w |
|---|---|---|
| $DR_{DC}$-$PR_{GASTRIC}$ Granules (G1) | | |
| Acarbose | 11.7 | 3.9 |
| Glyceryl monostearate | 18.7 | 6.2 |
| Hydrogenated vegetable oil type II, Dynasan P60 | 14.6 | 4.8 |
| Mannitol | 13.5 | 4.5 |
| Sub-total: | 58.5 | 19.4 |
| $DR_{EC}$-$RR_{PROX\,SI}$ Granules (G2) | | |
| Orlistat | 43.3 | 14.3 |
| Acarbose | 8.3 | 2.7 |
| Microcrystalline cellulose | 65.8 | 21.8 |
| Polysorbate 80, Tween 80 | 13.4 | 4.4 |
| Mannitol | 9.8 | 3.2 |
| Croscarmellose sodium | 5.9 | 2.0 |
| Sodium stearyl fumarate, Pruv | 2.1 | 0.7 |
| Opadry (HPMC low viscosity grade, 6 cps, tri-acetin, and talc) | 4.5 | 1.5 |
| Acryl-EZE (methacrylic acid copolymer Type C, sodium lauryl sulphate, macrogol, talc, sodium bicarbonate and colloidal silica, anhydrous) | 59.5 | 19.7 |
| Sub-total: | 212 | 70.2 |
| $DR_{DC}$-$PR_{GASTRIC}$ Granules (G3) | | |
| Orlistat | 16.7 | 5.5 |
| Polysorbate 80, Tween 80 | 5.8 | 1.9 |
| Microcrystalline cellulose | 7.5 | 2.5 |
| Sub-total: | 30.0 | 9.9 |
| Extragranular ingredients | | |
| Magnesium stearate | 1.5 | 0.5 |
| Total: | 302 | 100 |

The multiple-unit oral powders of Example 5D-M are prepared as follows:

The granules are prepared as described in Example 1 above. When the granules are dry; add all components into a tumbling mixer. Mix them during approximately 45 minutes, depending on mixer. When magnesium stearate is used as lubricant, add it after sieving during the last 2 minutes of blending. Transfer the final blend to a sachet filling and sealing machine and fill sachets of appropriate sizes in accordance with a powder content adjusted for the powder density and for the filling weight per sachet.

Example 6

Preliminary In Vivo Data (Clinical Investigation)

Preliminary in vivo data have been obtained from two male subjects who were investigated at two separate test days, where they either ingested a composition according to the invention (90 mg orlistat/30 mg acarbose, batch nr 326222) at breakfast and lunch, or just ingested the meals without any concomitant intake of the composition according to the invention. The composition was ingested 5 minutes after the meal was initiated to secure optimal mixing with the food. Blood samples were collected every 30 min until 300 min after onset of study (when the meal intake was initiated). Tolerability and appetite was monitored during the day using questionnaires. Subjects reported substantially higher feelings of satiety during the study day when the proposed product was taken together with food than without the proposed product (satiety scores around 8-7 out of 10 with product, and around 3 without product). This higher satiety seems to be related to the GI break mechanisms, which are the main target for invention. No side effects, apart from a temporary slight nausea and gastric distension, were noted. No orlistat could be observed in plasma using a detection method with a sensitivity of 0.05 ng/mL

Example 7. Patent Reference Examples

Example 7A, Coated Tablet, Orlistat 60 mg/Acarbose 50 mg

According to composition "Beispiel D" suggested in EP 0 638 317

| Ingredient | mg/tablet | % w/w |
|---|---|---|
| Tablet core | | |
| Acarbose | 50.0 | 19.6 |
| Orlistat | 60.0 | 23.5 |
| Lactose | 70.0 | 27.5 |
| Hydroxypropylmethylcellulose | 52.5 | 20.6 |
| Polyvinylpyrrolidone | 7.5 | 2.9 |
| Talc | 8.0 | 3.1 |
| Magnesium stearate | 1.0 | 0.4 |
| Silica, colloidal anhydrous | 1.0 | 0.4 |
| Sub-total: | 250 | 98.0 |
| HPMC-coating | | |
| Hydroxypropylmethylcellulose | 2.5 | 1.0 |
| Talc | 1.25 | 0.5 |
| Titandioxide | 1.25 | 0.5 |
| Total: | 255 | 100 |

Figure 21A:
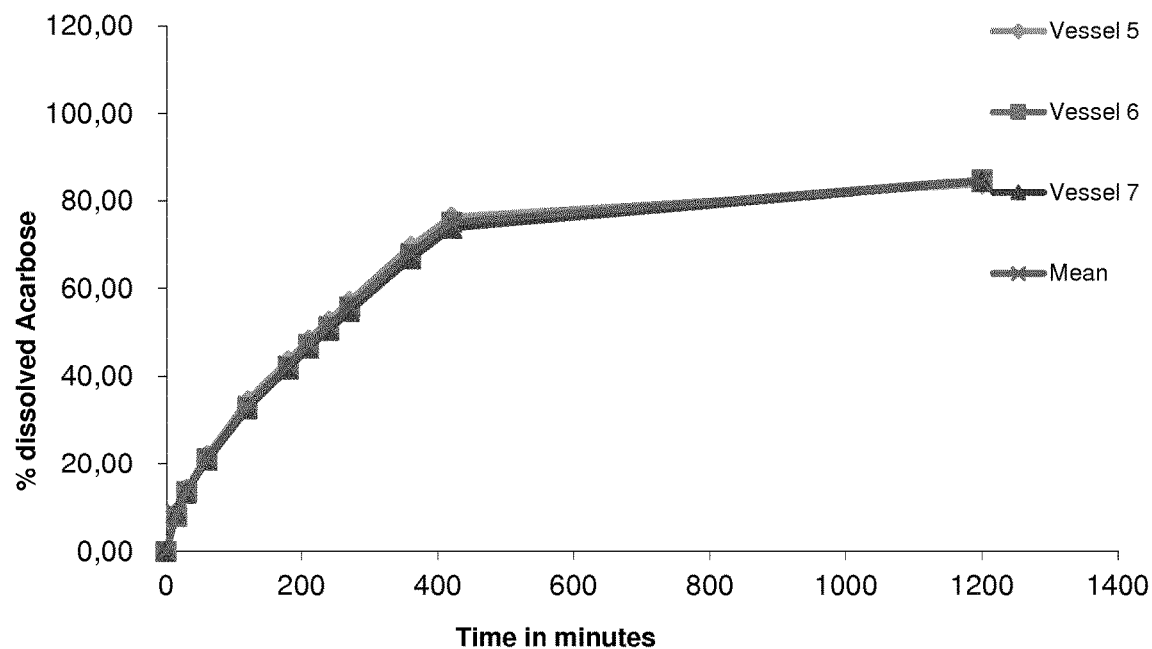
Figure 21B:
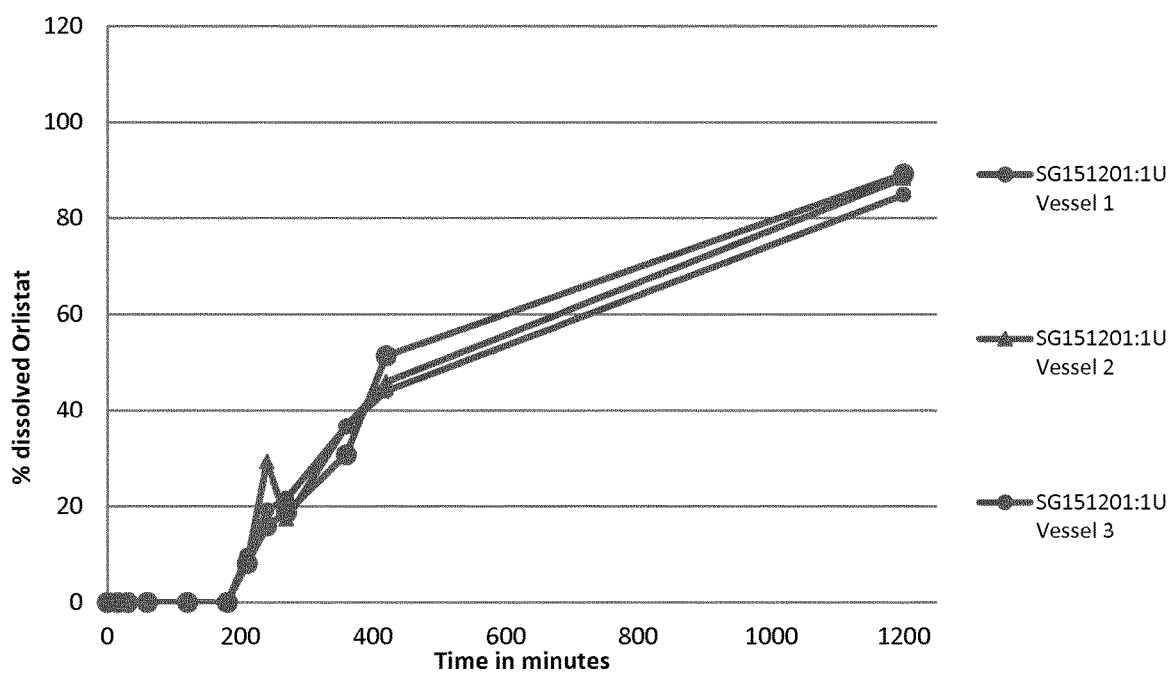

The in vitro release profile is shown in FIGS. 21*a* and 21*b*.

Example 7B, Two-Layer Tablet, Orlistat 60 mg/Acarbose 30 mg

According to composition "Example 3" suggested in CN 2011 1195582

| Ingredient | mg/tablet | % w/w |
|---|---|---|
| Orlistat layer | | |
| Orlistat | 60.0 | 6.3 |
| Hydroxypropylmethylcellulose, 4M | 40.0 | 5.9 |
| Microcrystalline cellulose | 20.0 | 0.6 |
| Polyvinylpyrrolidone | 0.8 | 0.4 |
| Magnesium stearate | 3.0 | 3.8 |
| Sub-total: | 123.8 | 13 |
| Acarbose layer | | |
| Acarbose | 30.0 | 3.1 |
| Sodium carboxymethylcellulose | 4.0 | 3.8 |
| Lactose | 3.0 | 3.1 |
| Polyvinylpyrrolidone | 0.3 | 3.8 |
| Magnesium stearate | 0.2 | 6.0 |
| Sub-total: | 37.5 | 29 |
| Total: | 161.3 | 100 |

Figure 22A:
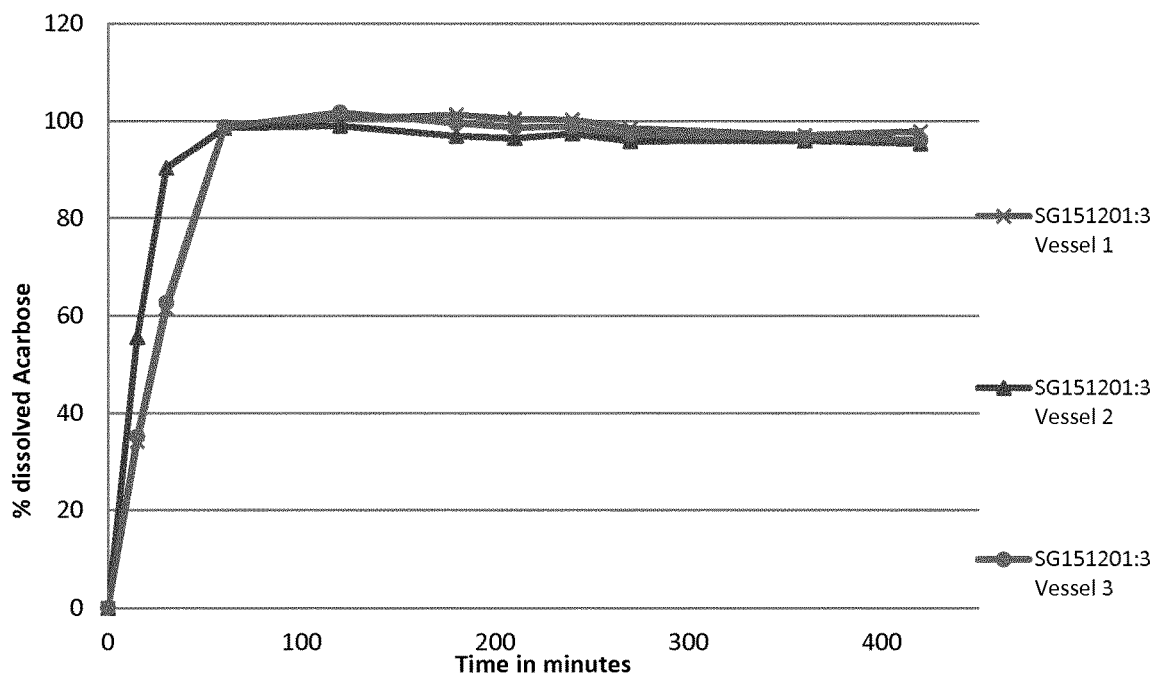
Figure 22B:
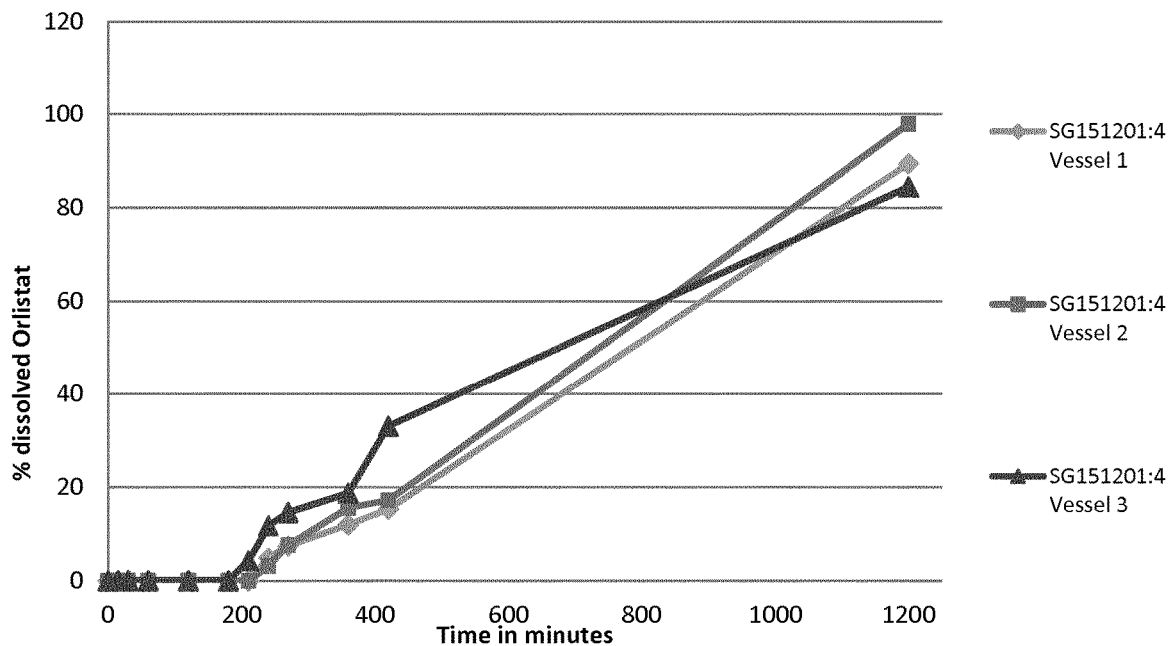
Figure 23A:
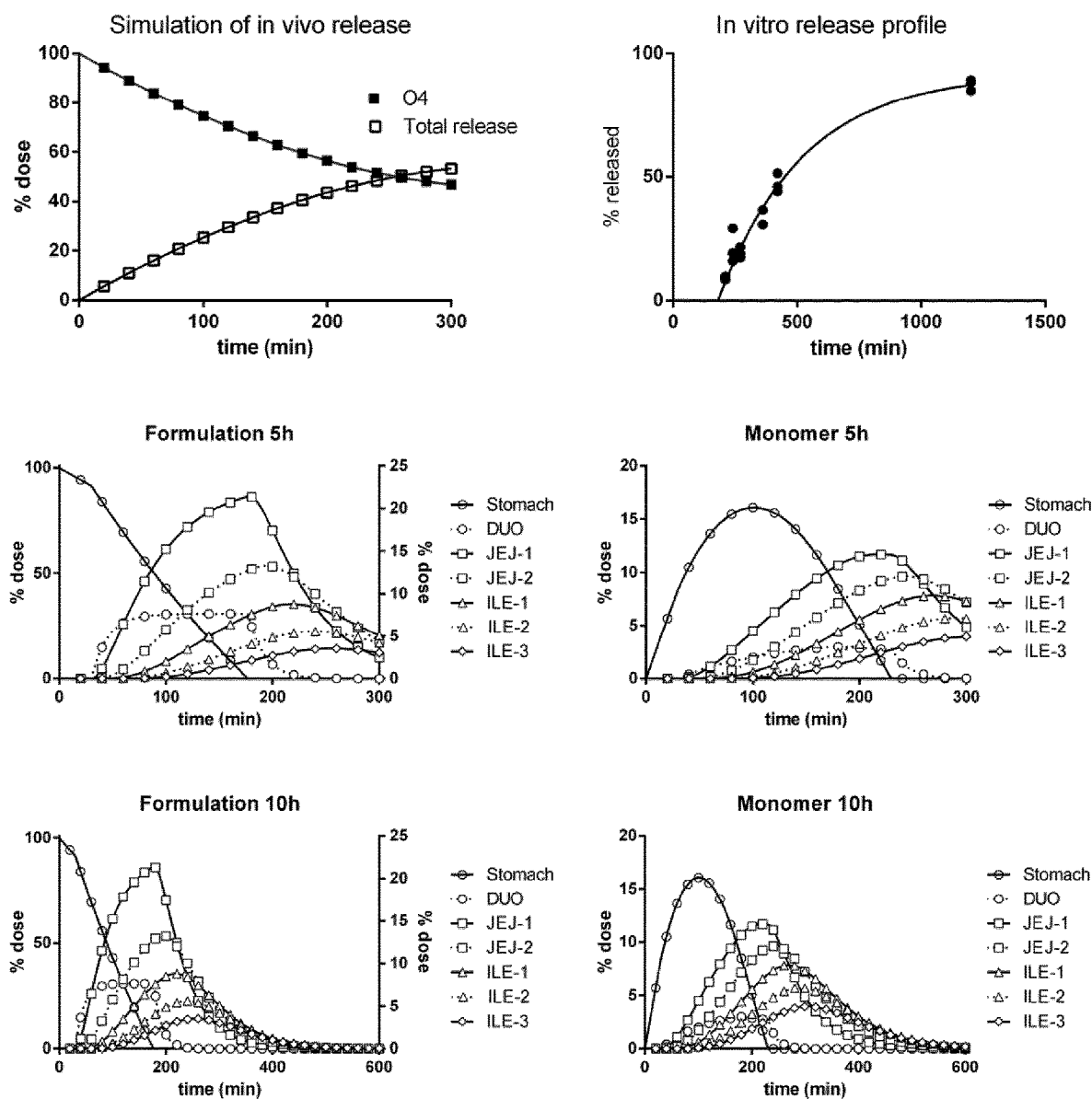
Figure 23B:
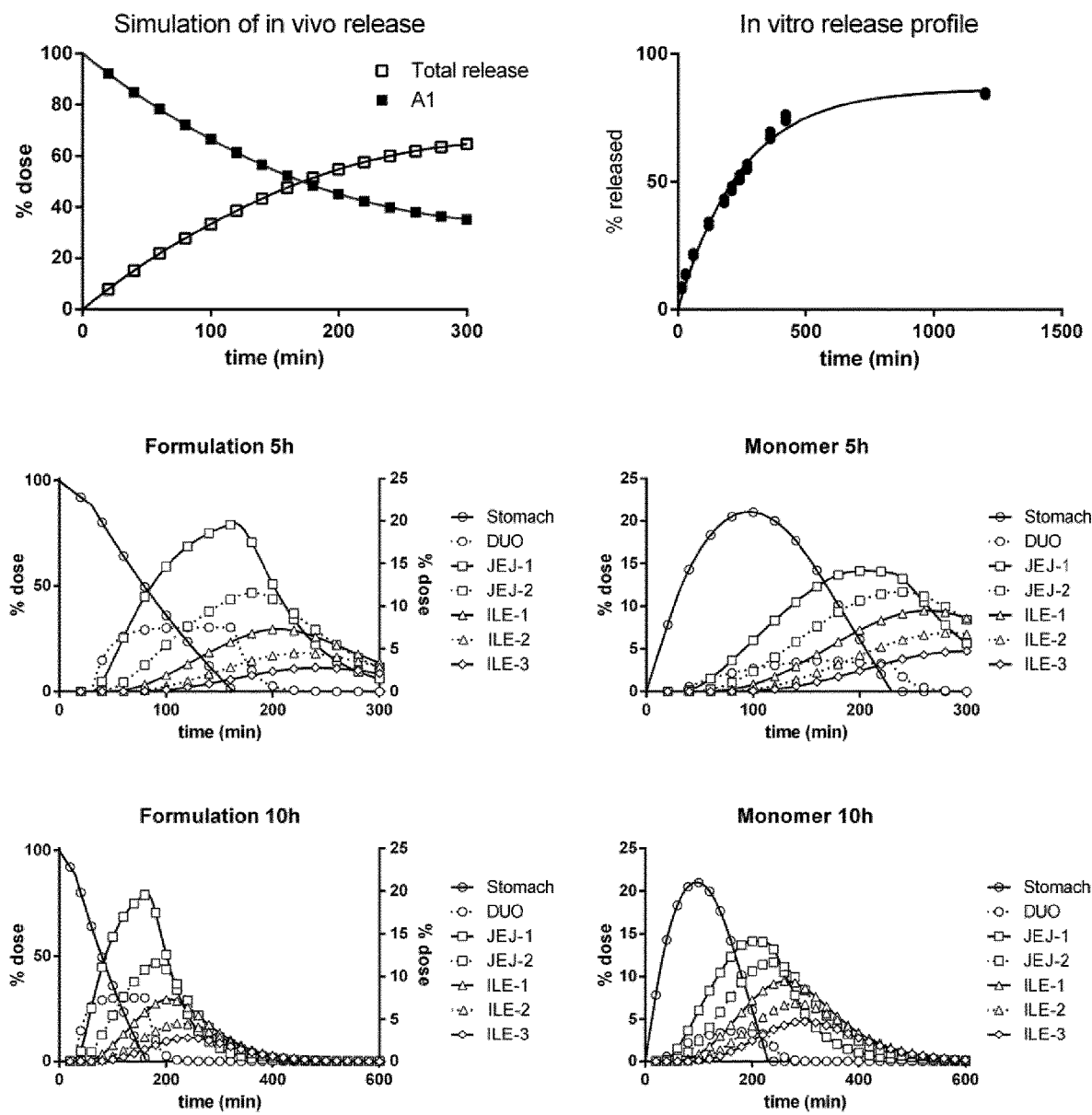
Figure 23C:
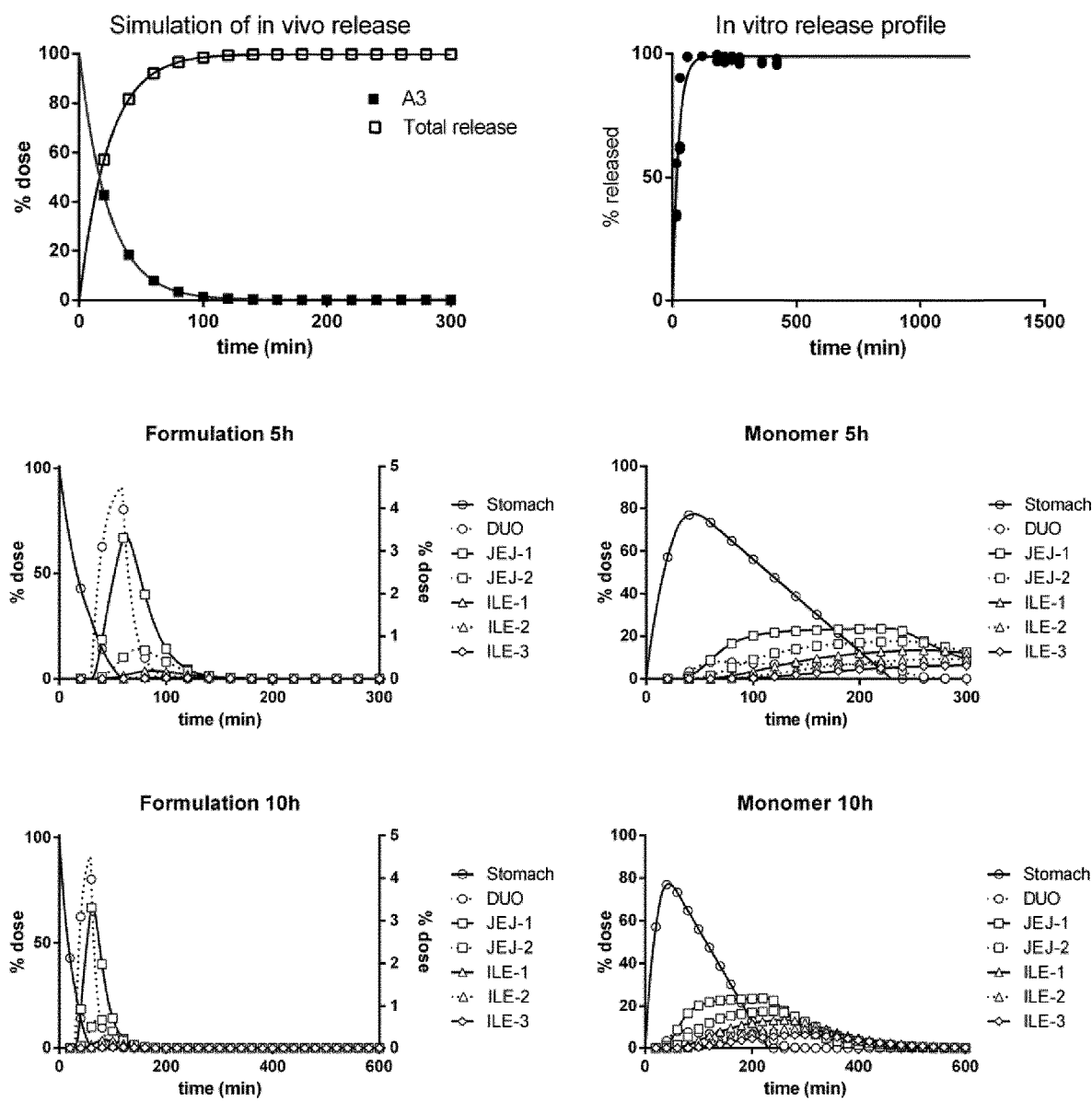
Figure 23D:
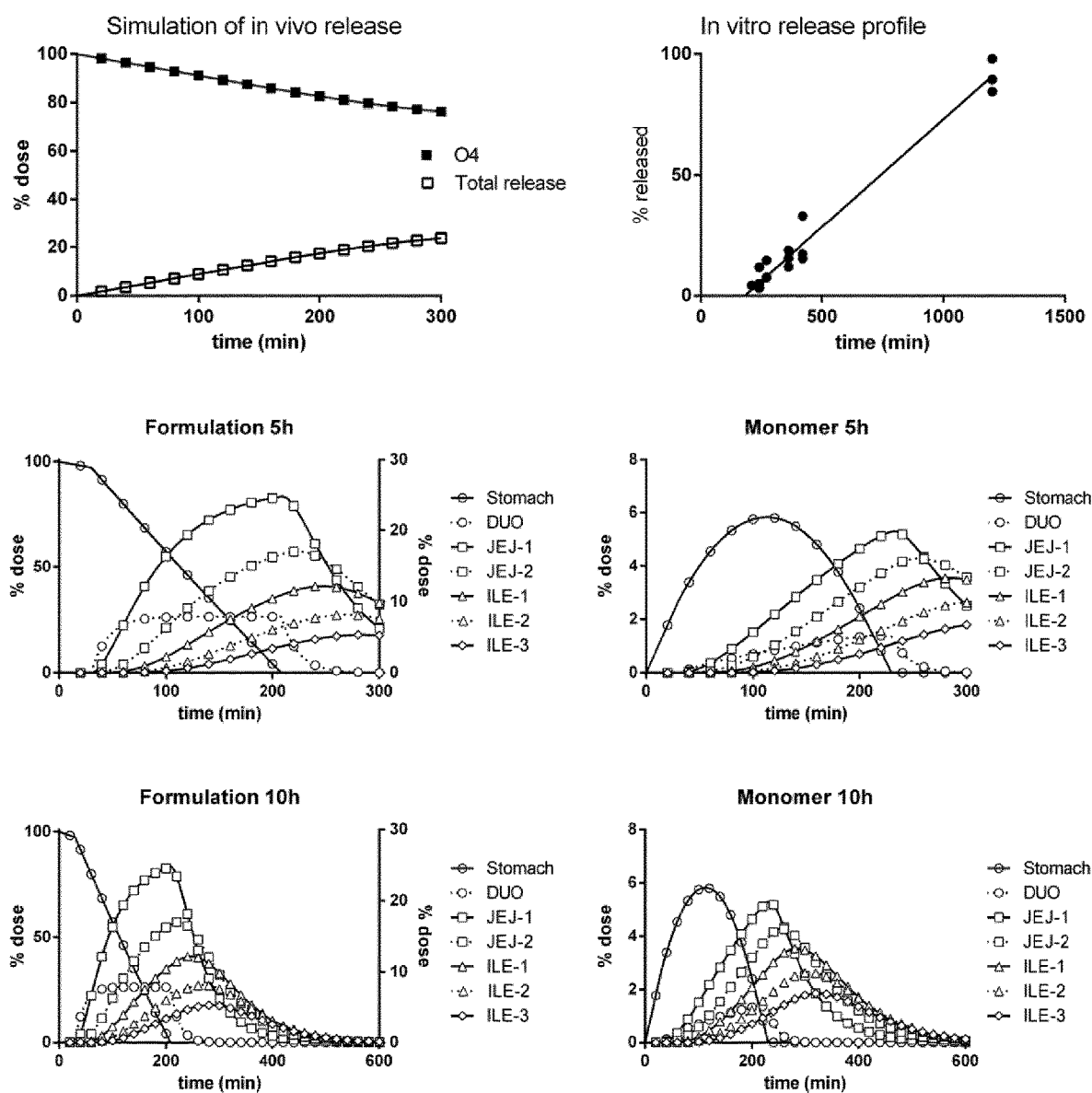

The in vitro dissolution profile is shown in FIGS. 22a and 22b.

The patent reference example of tablets are produced by using standard pharmaceutical manufacturing equipment in accordance with what is described in the patents.

REFERENCES

1. Wang, Y. C., McPherson, K., Marsh, T., Gortmaker, S. L. & Brown, M. Health and economic burden of the projected obesity trends in the USA and the UK. Lancet 378, 815-825 (2011).
2. WHO Obesity and overweight. (2014). at http://www.who.int/mediacentre/fact-sheets/fs311/en/
3. Malik, V. S., Willett, W. C. & Hu, F. B. Global obesity: trends, risk factors and policy implications. Nat. Rev. Endocrinol. 9, 13-27 (2013).
4. Must, A. et al. The disease burden associated with overweight and obesity. JAMA 282, 1523-1529 (1999).
5. AMA Adopts New Policies on Second Day of Voting at Annual Meeting. (2013). at <http://www.ama-assn.org/ama/pub/news/news/2013/2013-06-18-new-ama-policies-annual-meeting.page>
6. Atkinson, R. L. Current status of the field of obesity. Trends Endocrinol. Metab. 25, 283-284 (2014).
7. Kim, G. W., Lin, J. E., Blomain, E. S. & Waldman, S. A. Antiobesity pharma-cotherapy: new drugs and emerging targets. Clin. Pharmacol. Ther. 95, 53-66 (2014).
8. Alex, A. D. A. 1701 N. B. S., ria & 1-800-Diabetes, V. 22311. Diagnosing Diabe-tes and Learning About Prediabetes. American Diabetes Association at <http://www.diabetes.org/diabetes-basics/diagnosis/>
9. Solomon, C. G. The epidemiology of polycystic ovary syndrome. Prevalence and associated disease risks. Endocrinol. Metab. Clin. North Am. 28, 247-263 (1999).
10. Legro, R. S. et al. Diagnosis and Treatment of Polycystic Ovary Syndrome: An Endocrine Society Clinical Practice Guideline. J. Clin. Endocrinol. Metab. 98, 4565-4592 (2013).
11. Nonalcoholic Steatohepatitis. at <http://www.niddk.nih.gov/health-information/health-topics/liver-disease/nonalcoholic-steatohepatitis/Pages/facts.aspx>
12. Wong, D., Sullivan, K. & Heap, G. The pharmaceutical market for obesity therapies. Nat. Rev. Drug Discov. 11, 669-670 (2012).
13. Colman, E. Food and Drug Administration's Obesity Drug Guidance Document: a short history. Circulation 125, 2156-2164 (2012).
14. Yanovski, S. Z. & Yanovski, J. A. Long-term Drug Treatment for Obesity: A Sys-tematic and Clinical Review. JAMA 311, 74 (2014).
15. Connolly, H. M. et al. Valvular heart disease associated with fenfluramine-phentermine. N. Engl. J. Med. 337, 581-588 (1997).
16. O'Neil, P. M. et al. Randomized placebo-controlled clinical trial of lorcaserin for weight loss in type 2 diabetes mellitus: the BLOOM-DM study. Obes. Silver Spring Md. 20, 1426-1436 (2012).
17. Smith, S. R. et al. Multicenter, placebo-controlled trial of lorcaserin for weight management. N. Engl. J. Med. 363, 245-256 (2010).
18. Astrup, A. et al. Safety, tolerability and sustained weight loss over 2 years with the once-daily human GLP-1 analog, liraglutide. Int. J. Obes. 2005 36, 843-854 (2012).
19. Wadden, T. A. et al. Weight maintenance and additional weight loss with liraglutide after low-calorie-diet-induced weight loss: the SCALE Maintenance randomized study. Int. J. Obes. 2005 37, 1443-1451 (2013).
20. Drug Safety and Availability >FDA Drug Safety Communication: FDA investi-gating reports of possible increased risk of pancreatitis and pre-cancerous findings of the pancreas from incretin mimetic drugs for type 2 diabetes. at <http://www.fda.gov/Drugs/DrugSafety/ucm343187.htm>
21. Li, M.-F. & Cheung, B. M. Rise and fall of anti-obesity drugs. World J. Diabetes 2, 19-23 (2011).
22. McClendon, K. S., Riche, D. M. & Uwaifo, G. I. Orlistat: current status in clinical therapeutics. Expert Opin. Drug Saf. 8, 727-744 (2009).
23. Sjöström, L. et al. Randomised placebo-controlled trial of orlistat for weight loss and prevention of weight regain in obese patients. European Multicentre Orlistat Study Group. Lancet 352, 167-172 (1998).
24. FDA Response to Orlistat Petition Denial. at <http://www.citizen.org/documents/1942_FDA%20Response%20to%20Orlistat%20Petition_Denial.pdf>
25. Product Monograph Glucobay. at <http://www.bayer.ca/files/GLUCOBAY-PM-ENG10JUN2010-137275-rev1.pdf>
26. Kumar, R. V. & Sinha, V. R. Newer insights into the drug delivery approaches of α-glucosidase inhibitors. Expert Opin. Drug Deliv. 9, 403-416 (2012).
27. Dabhi, A. S., Bhatt, N. R. & Shah, M. J. Voglibose: an alpha glucosidase inhibi-tor. J. Clin. Diagn. Res. JCDR 7, 3023-3027 (2013).
28. Boath, A. S., Stewart, D. & McDougall, G. J. Berry components inhibit α-glucosidase in vitro: Synergies between acarbose and polyphenols from black currant and rowanberry. Food Chem. 135, 929-936 (2012).
29. Kopelman, P. et al. Weight Loss, HbA1c Reduction, and Tolerability of Cetilistat in a Randomized, Placebo-controlled Phase 2 Trial in Obese Diabetics: Comparison With Orlistat (Xenical). Obesity 18, 108-115 (2010).
30. Birari, R. B. & Bhutani, K. K. Pancreatic lipase inhibitors from natural sources: unexplored potential. Drug Discov. Today 12, 879-889 (2007).
31. Maljaars, P. W. J., Peters, H. P. F., Mela, D. J. & Masclee, A. A. M. Ileal brake: A sensible food target for appetite control. A review. Physiol. Behav. 95, 271-281 (2008).
32. Maljaars, P. W. J. et al. Effect of ileal fat perfusion on satiety and hormone re-lease in healthy volunteers. Int. J. Obes. 32, 1633-1639 (2008).
33. Maljaars, P. W. J. et al. The effect of lipid droplet size on satiety and peptide secretion is intestinal site-specific. Clin. Nutr. 31, 535-542 (2012).
34. Paschetta, E., Hvalryg, M. & Musso, G. Glucose-dependent insulinotropic pol-ypeptide: from pathophysiology to therapeutic opportunities in obesity-associated disorders. Obes. Rev. Off. J. Int. Assoc. Study Obes. 12, 813-828 (2011).
35. Engelstoft, M. S., Egerod, K. L., Hoist, B. & Schwartz, T. W. A gut feeling for obesity: 7TM sensors on enteroendocrine cells. Cell Metab. 8, 447-449 (2008).
35b. McClendon K S, Riche D M, Uwaifo G I. Orlistat: current status in clinical therapeutics. Expert Opin Drug Saf. November 2009; 8(6):727-44.
35c. Xenical [Internet] at http://www.ema.europa.eu/ema/index.jsp?curl=pages/medicines/human/medicines/000154/human_med_001158.jsp&mid=WC0b01ac058001d124
36. Ellrichmann, M. et al. Orlistat inhibition of intestinal lipase acutely increases appetite and attenuates postprandial glucagon-like peptide-1-(7-36)-amide-1, chole-cys- 37. Enç, F. Y. et al. Orlistat accelerates gastric emptying and attenuates GIP re-lease in healthy subjects. Am. J. Physiol. Gastrointest. Liver Physiol. 296, G482-489 (2009).
38. Feinle-Bisset, C., Patterson, M., Ghatei, M. A., Bloom, S. R. & Horowitz, M. Fat digestion is required for suppression of ghrelin and stimulation of peptide YY and pancreatic polypeptide secretion by intraduodenal lipid. Am. J. Physiol. Endocrinol. Metab. 289, E948-953 (2005).
39. Tai, K., Hammond, A. J., Wishart, J. M., Horowitz, M. & Chapman, I. M. Carbo-hydrate and fat digestion is necessary for maximal suppression of total plasma ghrelin in healthy adults. Appetite 55, 407-412 (2010).
40. Rosak, C. & Mertes. Critical evaluation of the role of acarbose in the treatment of diabetes: patient considerations. Diabetes Metab. Syndr. Obes. Targets Ther. 357 (2012). doi:10.2147/DMSO.S28340
41. Ahr, H. J. et al. Pharmacokinetics of acarbose. Part I: Absorption, concentra-tion in plasma, metabolism and excretion after single administration of [14C]acarbose to rats, dogs and man. Arzneimittelforschung. 39, 1254-1260 (1989).
42. Fischer, S., Hanefeld, M., Spengler, M., Boehme, K. & Temelkova-Kurktschiev, T. European study on dose-response relationship of acarbose as a first-line drug in noninsulin-dependent diabetes mellitus: efficacy and safety of low and high doses. Acta Diabetol. 35, 34-40 (1998).
43. Standl, E. & Schnell, O. Alpha-glucosidase inhibitors 2012—cardiovascular con-siderations and trial evaluation. Diab. Vasc. Dis. Res. 9, 163-169 (2012).
44. Kalra, S. et al. Alpha-glucosidase inhibitor, acarbose, improves glycamic con-trol and reduces body weight in type 2 diabetes: Findings on indian patients from the pooled data analysis. Indian J. Endocrinol. Metab. 17, S307-309 (2013).
45. FASS. at <http://www.fass.se/LIF/startpage>
46. Olszanecka-Glinianowicz, M. et al. Long-term inhibition of intestinal lipase by orlistat improves release of gut hormones increasing satiety in obese women. Pharmacol. Rep. 65, 666-671 (2013).
47. Enç, F. Y. et al. Inhibition of gastric emptying by acarbose is correlated with GLP-1 response and accompanied by CCK release. Am. J. Physiol. Gastrointest. Liver Physiol. 281, G752-763 (2001).
48. Tiss, A., Lengsfeld, H., Carrière, F. & Verger, R. Inhibition of human pancreatic lipase by tetrahydrolipstatin: Further kinetic studies showing its reversibility. J. Mol. Catal. B Enzym. 58, 41-47 (2009).
49. Meyer, J. H., Hlinka, M., Tabrizi, Y., DiMaso, N. & Raybould, H. E. Chemical specificities and intestinal distributions of nutrient-driven satiety. Am. J. Physiol. 275, R1293-1307 (1998).
50. Laube, H. Acarbose. Clin. Drug Investig. 22, 141-156 (2002).
51. Wolever, T. M. et al. Small weight loss on long-term acarbose therapy with no change in dietary pattern or nutrient intake of individuals with non-insulin-dependent diabetes. Int. J. Obes. Relat. Metab. Disord. J. Int. Assoc. Study Obes. 21, 756-763 (1997).
52. O'Dea, K. & Turton, J. Optimum effectiveness of intestinal alpha-glucosidase inhibitors: importance of uniform distribution through a meal. Am. J. Clin. Nutr. 41, 511-516 (1985).
53. Yu, L. X. & Amidon, G. L. A compartmental absorption and transit model for estimating oral drug absorption. Int. J. Pharm. 186, 119-125 (1999).
54. Sjögren, E. et al. In silico predictions of gastrointestinal drug absorption in pharmaceutical product development: Application of the mechanistic absorption mod-el GI-Sim. Eur. J. Pharm. Sci. 49, 679-698 (2013).
55. Olausson, E. A. et al. Small particle size of a solid meal increases gastric emp-tying and late postprandial glycaemic response in diabetic subjects with gastroparesis. Diabetes Res. Clin. Pract. 80, 231-237 (2008).
56. Sjögren, E. et al. In vivo methods for drug absorption—comparative physiolo-gies, model selection, correlations with in vitro methods (IVIVC), and applications for formulation/API/excipient characterization including food effects. Eur. J. Pharm. Sci. Off. J. Eur. Fed. Pharm. Sci. 57, 99-151 (2014).
57. Bønløkke, L. et al. A comparison between direct determination of in vivo dis-solution and the deconvolution technique in humans. Eur. J. Pharm. Sci. Off. J. Eur. Fed. Pharm. Sci. 8, 19-27 (1999).
58. Bønløkke, L., Hovgaard, L., Kristensen, H. G., Knutson, L. & Lennernäs, H. Di-rect estimation of the in vivo dissolution of spironolactone, in two particle size ranges, using the single-pass perfusion technique (Loc-I-Gut) in humans. Eur. J. Pharm. Sci. Off. J. Eur. Fed. Pharm. Sci. 12, 239-250 (2001).
59. Lennernäs, H. & Abrahamsson, B. The use of biopharmaceutic classification of drugs in drug discovery and development: current status and future extension. J. Pharm. Pharmacol. 57, 273-285 (2005).
60. Dickinson, P. A. et al. Clinical relevance of dissolution testing in quality by de-sign. AAPS J. 10, 380-390 (2008).
61. ICH Guidline. at <http://www.ich.org/products/guidelines/quality/article/qualityguidelines.html>
62. Williams, H. D. et al. Toward the establishment of standardized in vitro tests for lipid-based formulations, part 3: understanding supersaturation versus precipitation potential during the in vitro digestion of type I, II, IIIA, IIIB and IV lipid-based for-mulations. Pharm. Res. 30, 3059-3076 (2013).
63. United States Pharmacopoeia General Test Chapter on DISSOLUTION <711>, USP 37. at <http://www.usp.org/sites/default/files/usp_pdf/EN/USPNF/2011-02-25711DISSOLUTION.pdf>
64. FDA Guidance for Industry: Orally Disintegrating Tablets. (2008). at <http://www.fda.gov/downloads/Drugs/GuidanceComplianceRegulatoryInformation/Guidances/ucm070578.pdf>
65. American Pharmacists Association. Handbook of pharmaceutical excipients/edited by Raymond C. Rowe, BPharm, PhD, DSC, FRPharmS, FRSC, CPhys, MInstP, chief scientist, Paul J. Sheskey, BSc, RPh, principal research scientist, the Dow Chemical Company, Midland, Mich., USA, Walter G. Cook, BSc, PhD, research fellow, Materials Science group of Pharmaceutical R&D, Pfizer, Sandwich, Kent, UK, Marian E. Fenton, BSc, MSc, development editor, Royal Pharmaceutical Society of Great Britain, London, UK. (APhA/Pharmaceutical Press, 2012).
66. Mohanachandran, Sindhumol & Kiran. Superdisintegrants: An Overview. In-terational J. Pharm. Sci. Rev. Res. 2011, 105-109
67. Lennernäs, H. Human jejunal effective permeability and its correlation with preclinical drug absorption models. J. Pharm. Pharmacol. 49, 627-638 (1997).

68. Amidon, G. L., Lennernäs, H., Shah, V. P. & Crison, J. R. A theoretical basis for a biopharmaceutic drug classification: the correlation of in vitro drug product dissolution and in vivo bioavailability. Pharm. Res. 12, 413-420 (1995).

69. Tannergren, C., Bergendal, A., Lennernäs, H. & Abrahamsson, B. Toward an increased understanding of the barriers to colonic drug absorption in humans: implications for early controlled release candidate assessment. Mol. Pharm. 6, 60-73 (2009).

70. Geliebter, A. Gastric distension and gastric capacity in relation to food intake in humans. Physiol. Behav. 44, 665-668 (1988).

71. Geliebter, A. & Hashim, S. A. Gastric capacity in normal, obese, and bulimic women. Physiol. Behav. 74, 743-746 (2001).

72. Chial, H. J. et al. A nutrient drink test to assess maximum tolerated volume and postprandial symptoms: effects of gender, body mass index and age in health. Neurogastroenterol. Motil. Off. J. Eur. Gastrointest. Motil. Soc. 14, 249-253 (2002).

73. Goetze, O. et al. The effect of gastric secretion on gastric physiology and emp-tying in the fasted and fed state assessed by magnetic resonance imaging. Neurogas-troenterol. Motil. Off. J. Eur. Gastrointest. Motil. Soc. 21, 725-e42 (2009).

74. Kwiatek, M. A. et al. Effect of meal volume and calorie load on postprandial gastric function and emptying: studies under physiological conditions by combined fi-ber-optic pressure measurement and MRI. Am. J. Physiol. Gastrointest. Liver Physiol. 297, G894-901 (2009).

75. Burton, D. D. et al. Relationship of gastric emptying and volume changes after a solid meal in humans. Am. J. Physiol. Gastrointest. Liver Physiol. 289, G261-266 (2005).

76. Versantvoort, van de Kamp, Rompelberg. Development and applicability of an in vitro digestion model in assessing the bioaccessibility of contaminants from food. (2004).

77. Engelen, L., de Wijk, R. A., Prinz, J. F., van der Bilt, A. & Bosman, F. The relation between saliva flow after different stimulations and the perception of flavor and texture attributes in custard desserts. Physiol. Behav. 78, 165-169 (2003).

78. Gavião, M. B. D., Engelen, L. & van der Bilt, A. Chewing behavior and salivary secretion. Eur. J. Oral Sci. 112, 19-24 (2004).

79. Chang, C. A., McKenna, R. D. & Beck, I. T. Gastric emptying rate of the water and fat phases of a mixed test meal in man. Gut 9, 420-424 (1968).

80. Kunz, P. et al. Effect of ingestion order of the fat component of a solid meal on intragastric fat distribution and gastric emptying assessed by MRI. J. Magn. Reson. Imaging JMRI 21, 383-390 (2005).

81. Keinke, O., Schemann, M. & Ehrlein, H. J. Mechanical factors regulating gastric emptying of viscous nutrient meals in dogs. Q. J. Exp. Physiol. Camb. Engl. 69, 781-795 (1984).

82. Marciani, L. et al. Gastric response to increased meal viscosity assessed by echo-planar magnetic resonance imaging in humans. J. Nutr. 130, 122-127 (2000).

83. Dikeman, C. L., Murphy, M. R. & Fahey, G. C. Dietary fibers affect viscosity of solutions and simulated human gastric and small intestinal digesta. J. Nutr. 136, 913-919 (2006).

84. Mudie, D. M., Amidon, G. L. & Amidon, G. E. Physiological parameters for oral delivery and in vitro testing. Mol. Pharm. 7, 1388-1405 (2010).

85. Abrahamsson, B. et al. A novel in vitro and numerical analysis of shear-induced drug release from extended-release tablets in the fed stomach. Pharm. Res. 22, 1215-1226 (2005).

85b. Khosla, R., and S. S. Davis. 1990. The effect of tablet size on the gastric emptying of nondisintegrating tablets. Int J Pharm 62:R9.

85c. Cassilly D, Kantor S, Knight L C, Maurer A H, Fisher R S, Semler J, Parkman H P. Gastric emptying of a non-digestible solid: assessment with simultaneous SmartPill pH and pressure capsule, antroduodenal manometry, gastric emptying scintigraphy. Neurogastroenterol Motil. 2008 April; 20(4):311-9.

86. Sarna, S. K. Cyclic motor activity; migrating motor complex: 1985. Gastroen-terology 89, 894-913 (1985).

87. Ouyang, A., Sunshine, A. G. & Reynolds, J. C. Caloric content of a meal affects duration but not contractile pattern of duodenal motility in man. Dig. Dis. Sci. 34, 528-536 (1989).

88. Boulby, P., Moore, R., Gowland, P. & Spiller, R. C. Fat delays emptying but increases forward and backward antral flow as assessed by flow-sensitive magnetic resonance imaging. Neurogastroenterol. Motil. Off. J. Eur. Gastrointest. Motil. Soc. 11, 27-36 (1999).

89. Pal, A. et al. Gastric flow and mixing studied using computer simulation. Proc. Biol. Sci. 271, 2587-2594 (2004).

90. Ferrua, M. J., Kong, F. & Singh, R. P. Computational modeling of gastric diges-tion and the role of food material properties. Trends Food Sci. Technol. 22, 480-491 (2011).

91. Pal, A., Brasseur, J. G. & Abrahamsson, B. A stomach road or 'Magenstrasse' for gastric emptying. J. Biomech. 40, 1202-1210 (2007).

92. Marciani, L. et al. Effect of meal viscosity and nutrients on satiety, intragastric dilution, and emptying assessed by MRI. Am. J. Physiol. Gastrointest. Liver Physiol. 280, G1227-1233 (2001).

93. Meyer, J. H., Ohashi, H., Jehn, D. & Thomson, J. B. Size of liver particles emp-tied from the human stomach. Gastroenterology 80, 1489-1496 (1981).

94. Khosla, Davis. The Effect of Tablet Size on the Gastric-Emptying of Nondisintegrating Tablets. Int. J. Pharm. 1990, R9-R11

95. Newton, J. M. Gastric emptying of multi-particulate dosage forms. Int. J. Pharm. 395, 2-8 (2010).

96. Faas, H. et al. Pressure-geometry relationship in the antroduodenal region in humans. Am. J. Physiol. Gastrointest. Liver Physiol. 281, G1214-1220 (2001).

97. Kong, F. & Singh, R. P. Disintegration of solid foods in human stomach. J. Food Sci. 73, R67-80 (2008).

98. Oberle, R. L. et al. The influence of the interdigestive migrating myoelectric complex on the gastric emptying of liquids. Gastroenterology 99, 1275-1282 (1990).

99. Wilson, J. P. Surface area of the small intestine in man. Gut 8, 618-621 (1967).

100. Helander, H. F. & Fändriks, L. Surface area of the digestive tract—revisited. Scand. J. Gastroenterol. 49, 681-689 (2014).

101. Dressman, J. B. et al. Upper gastrointestinal (GI) pH in young, healthy men and women. Pharm. Res. 7, 756-761 (1990).

102. Lindahl, A., Ungell, A. L., Knutson, L. & Lennernäs, H. Characterization of fluids from the stomach and proximal jejunum in men and women. Pharm. Res. 14, 497-502 (1997).
103. Simonian, H. P., Vo, L., Doma, S., Fisher, R. S. & Parkman, H. P. Regional postprandial differences in pH within the stomach and gastroesophageal junction. Dig. Dis. Sci. 50, 2276-2285 (2005).
104. Charman, W. N., Porter, C. J., Mithani, S. & Dressman, J. B. Physiochemical and physiological mechanisms for the effects of food on drug absorption: the role of lipids and pH. J. Pharm. Sci. 86, 269-282 (1997).
105. Vo, L., Simonian, H. P., Doma, S., Fisher, R. S. & Parkman, H. P. The effect of rabeprazole on regional gastric acidity and the postprandial cardia/gastro-oesophageal junction acid layer in normal subjects: a randomized, double-blind, placebo-controlled study. Aliment. Pharmacol. Ther. 21, 1321-1330 (2005).
106. Szurszewski, J. H. A migrating electric complex of canine small intestine. Am. J. Physiol. 217, 1757-1763 (1969).
107. Varum, F. J. O., Merchant, H. A. & Basit, A. W. Oral modified-release formulations in motion: the relationship between gastrointestinal transit and drug absorption. Int. J. Pharm. 395, 26-36 (2010).
108. Weitschies, W., Blume, H. & Mönnikes, H. Magnetic marker monitoring: high resolution real-time tracking of oral solid dosage forms in the gastrointestinal tract. Eur. J. Pharm. Biopharm. Off. J. Arbeitsgemeinschaft Für Pharm. Verfahrenstechnik EV 74, 93-101 (2010).
109. Wilson, C. G. The transit of dosage forms through the colon. Int. J. Pharm. 395, 17-25 (2010).
110. Cassilly, D. et al. Gastric emptying of a non-digestible solid: assessment with simultaneous SmartPill pH and pressure capsule, antroduodenal manometry, gastric emptying scintigraphy. Neurogastroenterol. Motil. Off. J. Eur. Gastrointest. Motil. Soc. 20, 311-319 (2008).
111. Rogers, J., Henry, M. M. & Misiewicz, J. J. Increased segmental activity and intraluminal pressures in the sigmoid colon of patients with the irritable bowel syn-drome. Gut 30, 634-641 (1989).
112. Davis, S. S., Hardy, J. G. & Fara, J. W. Transit of pharmaceutical dosage forms through the small intestine. Gut 27, 886-892 (1986).
113. Schiller, C. et al. Intestinal fluid volumes and transit of dosage forms as as-sessed by magnetic resonance imaging. Aliment. Pharmacol. Ther. 22, 971-979 (2005).
114. Fadda, H. M., McConnell, E. L., Short, M. D. & Basit, A. W. Meal-induced acceleration of tablet transit through the human small intestine. Pharm. Res. 26, 356-360 (2009).
115. Weitschies, W., Kosch, O., Mönnikes, H. & Trahms, L. Magnetic Marker Moni-toring: An application of biomagnetic measurement instrumentation and principles for the determination of the gastrointestinal behavior of magnetically marked solid dos-age forms. Adv. Drug Deliv. Rev. 57, 1210-1222 (2005).
116. Lennernäs, H. Human intestinal permeability. J. Pharm. Sci. 87, 403-410 (1998).
117. Fagerholm, U., Borgström, L., Ahrenstedt, O. & Lennernas, H. The lack of ef-fect of induced net fluid absorption on the in vivo permeability of terbutaline in the human jejunum. J. Drug Target. 3, 191-200 (1995).
118. Winiwarter, S. et al. Correlation of human jejunal permeability (in vivo) of drugs with experimentally and theoretically derived parameters. A multivariate data analysis approach. J. Med. Chem. 41, 4939-4949 (1998).

Specific Embodiments

1. A modified-release composition comprising orlistat and acarbose, comprising:
a) a first part comprising from about 5 to about 70% w/w of the total dose of acarbose,
b) a second part comprising from about 30 to about 95% w/w of the total dose of acarbose,
c) a third part comprising from about 10 to about 90% w/w of the total dose of orlistat, and
d) a fourth part comprising from about 10 to about 80% w/w of the total dose of orlistat, and the total concentration of acarbose and orlistat, respectively, is 100% w/w, and wherein the individual parts are different.

2. A modified-release composition according to item 1, wherein part b) and part c) is combined so that the composition only contains three different parts.

3. A modified-release composition according to item 2, wherein the composition contains three different parts:
a) a first part comprising from about 5 to about 70% w/w of the total dose of acarbose,
b) a second part comprising from about 30 to about 95% w/w of the total dose of acarbose, and from about 10 to about 90% w/w of the total dose of orlistat, and
c) a third part comprising from about 10 to about 80% w/w of the total dose of orlistat, and the total concentration of acarbose and orlistat, respectively, is 100% w/w.

4. A modified-release composition comprising orlistat and acarbose, wherein the composition contains components with different release characteristics for release at different parts along the GI tract:
i) a $DR_{DC}$-$PR_{GASTRIC}$ part that is designed to release acarbose in a delayed, but prolonged manner,
ii) a $DR_{EC}$-$RR_{PROX\ SI}$ part that is designed to release acarbose and orlistat in the proximal small intestine,
iii) a $DR_{DC}$-$PR_{GASTRIC}$ and/or $DR_{EC}$-$PR_{INTESTINAL}$ part that is designed to release orlistat in the proximal part of the small intestine until the end of jejunum.

5. A modified-release composition according to item 4, wherein part i) of the composition is in the form of granules, pellets, minitablets etc. or part i) is incorporated into a two-layer tablet, where part i) is contained in one of the two layers, and the layer containing part i) is provided with a delayed release coating.

6. A modified-release composition according to item 4 or 5, wherein part i) of the composition contains from about 5 to about 70% w/w of the total dose of acarbose.

7. A modified-release composition according to any one of items 4-6, wherein part ii) of the composition is in the form of granules, pellets, minitablets etc. provided with an enteric coating or incorporated into a two-layer tablet, where part ii) is contained in one of the two layers and the layer containing part ii) is provided with an enteric coating.

8. A modified-release composition according to any one of items 4-7, wherein part ii) of the composition contains from about 30 to about 95% w/w of the total amount of acarbose and from 30 to 90% w/w of the total amount of orlistat.

9. A modified-release composition according to any one of items 4-8, wherein part iii) is in the form of granules, pellets, minitablets etc. or it is contained in a two layer tablet, wherein part iii) is contained in one of the two layers.

10. A modified-release composition according to any one of items 4-9, wherein part iii) contains from about 10 to about 70% w/w of the total amount of orlistat.

11. A modified-release composition according to any one of items 4-9 having the characteristics defined in any one of items 1-3.

12. A modified-release composition according to any one of items 1-11 in the form of a multiple-unit tablet, a bi-layer multiple-unit tablet, a coated tablet, a multiple-unit capsule or a multiple-unit oral powder.

13. A modified-release composition according to any of the preceding items comprising:
i) granules containing acarbose $DR_{DC}$-$PR_{GASTRIC}$ (denoted as Granule 1 or G1)
ii) granules containing acarbose and orlistat $DR_{EC}$-$RR_{PROX\ SI}$ (denoted as Granule 2 or G2), and
iii) granules containing orlistat $DR_{DC}$-$PR_{GASTRIC}$ and/or $DR_{EC}$-$PR_{INTESTINAL}$ (denoted as Granule 3 or G3).

14. A modified-release composition as defined in any of the preceding items for use in triggering the gastro-intestinal brake as defined in this application.

15. A method for the treatment or prevention of: overweight and obesity; type 2 diabetes; Elevated blood glucose level (such as impaired glucose tolerance), Polycystic ovarian syndrome; Disorders of lipoprotein metabolism and other lipidemias (such as hyperglyceridemia); Nonalcoholic fatty liver disease (NAFLD); Nonalcoholic steatohepatitis; or metabolic syndrome, the method comprising administering a combination of acarbose and orlistat in a manner as defined herein, or as monotheraphies.

The invention claimed is:

1. A modified-release oral composition comprising orlistat and acarbose, comprising as individually distinct parts with different release patterns:
   (a) a first $DR_{DC}$-$PR_{GASTRIC}$ part (G1) formulated to release acarbose in a delayed and prolonged manner, comprising acarbose and one or more of a hydrophobic polymer, a lipid and a wax, wherein G1 comprises from about 5 to about 70% w/w of the total dose of acarbose present in the composition;
   (b) a second $DR_{EC}$-$RR_{PROX\ SI}$ part (G2) formulated to rapidly release acarbose and orlistat in the proximal small intestine, comprising a core comprising acarbose, orlistat, and surfactant, and an enteric polymer coating surrounding the core, wherein G2 comprises from about 30 to about 95% w/w of the total dose of acarbose present in the composition, and from about 10 to about 90% w/w of the total dose of orlistat present in the composition; and
   (c) a third $DR_{EC}$-$PR_{INTESTINAL}$ part (G3) formulated to release orlistat in the proximal part of the small intestine until the end of jejunum, comprising orlistat and one or more of a surfactant and a water-soluble polymer, wherein G3 comprises from about 10 to about 80% w/w of the total dose of orlistat present in the composition.

2. A modified-release composition according to claim 1, wherein G1 is in the form of granules, pellets, minitablets, or spheres, or is incorporated into a two-layer tablet wherein G1 is contained in one of the two layers.

3. A modified-release composition according to claim 2, wherein G1 is incorporated into a two-layer tablet wherein G1 is contained in one of the two layers, and wherein the layer containing G1 is provided with a delayed release coating.

4. A modified-release composition according to claim 1, wherein G2 is in the form of granules, pellets, minitablets, or spheres, optionally containing an enteric polymer, or is incorporated into a two-layer tablet wherein G2 is contained in one of the two layers and the layer containing G2 is provided with an enteric coating.

5. A modified-release composition according to claim 1, wherein G3 is in the form of granules, pellets, minitablets, or spheres, or is contained in a two layer tablet wherein G3 is contained in one of the two layers.

6. A modified-release composition according to claim 1, wherein G1 comprises acarbose and a hydrophobic polymer, and the hydrophobic polymer is selected from ethylcellulose, acrylates or acrylic acid derivatives, gelatin, coating agents selected from co-polymers based on polymethacrylic acid and methacrylates, ethyl acrylate and methyl acrylate, co-polymers of acrylic and methacrylic acid esters, hydroxypropyl methylcellulose phthalate, cellulose acetate phthalate, polyvinyl acetate phthalate, and mixtures thereof.

7. A modified-release composition according to claim 6, wherein the hydrophobic polymer is ethylcellulose.

8. A modified-release composition according to claim 1, wherein G1 comprises acarbose and a lipid, and the lipid is selected from fatty acids, fatty esters, fatty alcohols, cetyl alcohol, stearyl alcohol, mineral oils, hydrogenated vegetable oils, vegetable oils, acetylated hydrogenated soybean oil glycerides, Castor oil, hydrogenated vegetable oils, and mixtures thereof.

9. A modified-release composition according to claim 1, wherein the hydrophobic polymer, lipid or wax is present in a concentration of from about 10% to about 50% w/w of the total weight of G1.

10. A modified-release composition according to claim 1, wherein G2 comprises an enteric polymer selected from acrylate, acrylic acid polymers, acrylic acid co-polymers, hydroxypropyl methylcellulose phthalate, cellulose acetate phthalate, polyvinyl acetate phthalate, and mixtures thereof.

11. A modified-release composition according to claim 10, wherein the enteric polymer is selected from co-polymers based on polymethacrylic acid and methacrylates, ethyl acrylate and methyl acrylate, co-polymers of acrylic and methacrylic acid esters, and mixtures thereof.

12. A modified-release composition according to claim 10, wherein the enteric polymer is present in a concentration of from about 15 to about 50% w/w of the total weight of G2.

13. A modified-release composition according to claim 1, wherein G2 comprises a surfactant selected from anionic, cationic and non-ionic surfactants, and mixtures thereof.

14. A modified-release composition according to claim 13, wherein the non-ionic surfactant is selected from polysorbate 20, polysorbate 21, polysorbate 40, polysorbate 60, polysorbate 61, polysorbate 65, polysorbate 80, polysorbate 81, polysorbate 85, polysorbate 120, sorbitan monoisostearate, sorbitan monolaurate, sorbitan monopalmitate, sorbitan monostearate, sorbitan monooleate, sorbitan sesquioleate, sorbitan trioleate, glyceryl monooleate and polyvinylalcohol, and mixtures thereof the anionic surfactant is selected from docusate sodium and sodium lauryl sulphate, and mixtures thereof; and the cationic surfactant is selected from benzalkonium chloride, benzethonium chloride and cetrimide, and mixtures thereof.

15. A modified-release composition according to claim 13, wherein the concentration of surfactant(s) in G2 is from about 0.5% to about 30% w/w of the total weight of G2.

16. A modified-release composition according to claim 1, wherein G3 comprises a water-soluble polymer selected from hydroxypropylmethylcellulose, methylcellulose, carboxymethylcellulose and hydroxypropylcellulose, and mixtures thereof.

17. A modified-release composition according to claim 16, wherein the water-soluble polymer is present at a concentration of from about 70 to about 90% w/w of the total weight of G3.

18. A modified-release composition according to claim 1 in the form of a multiple-unit tablet, a bi-layer multiple-unit tablet, a coated tablet, a multiple-unit capsule or a multiple-unit oral powder.

19. A modified-release composition according to claim 1, wherein G1, G2, and G3 are in the form of pellets, granules, or spheres.

20. A modified-release composition according to claim 1 in the form of a multiple-unit tablet, capsule, sachet or powder.

21. A modified-release composition according to claim 1, wherein the modified-release composition rapidly disintegrates into parts G1, G2 and G3 upon mixing with gastric contents.

22. A modified-release composition according to claim 1, wherein G1 releases acarbose after a first delay and G2 releases acarbose and orlistat after a second delay.

23. A modified-release composition according to claim 22, wherein G1 releases acarbose after a first delay, G2 releases acarbose and orlistat after a second delay, and G3 releases orlistat after a third delay.

24. A modified-release composition according to claim 1, wherein (a) 5-70% w/w of the total dose of acarbose is released in a prolonged manner, starting in the stomach and continuing in the duodenum and jejunum;
(b) 30-95% w/w of the total dose of acarbose is rapidly released in the proximal part of the small intestine to provide acarbose efficacy in the duodenum;
(c) 10-90% w/w of the total dose of orlistat is rapidly released in the duodenum and proximal jejunum and to provide orlistat efficacy in the duodenum and proximal jejunum, and
(d) 10-80% w/w of the total dose of orlistat is released in a prolonged manner in the duodenum and jejunum.

25. A method of triggering the gastro-intestinal brake, comprising orally administering a modified-release composition according to claim 1 to a subject in need thereof.

26. A method for treating or reducing the risks of a condition selected from one or more of being overweight, obesity, type 2 diabetes, elevated blood glucose levels, impaired glucose tolerance, polycystic ovarian syndrome, disorders of lipoprotein metabolism, lipidemia, hyperglyceridemia; nonalcoholic fatty liver disease (NAFLD), nonalcoholic steatohepatitis; and metabolic syndrome, comprising administering a modified-release composition according to claim 1 to a subject in need thereof.

27. A cosmetic method for reducing body weight, comprising administering to a subject in need thereof a modified-release composition according to claim 1.

* * * * *